(12) United States Patent
Soliman et al.

(10) Patent No.: US 12,233,115 B2
(45) Date of Patent: Feb. 25, 2025

(54) LONG-ACTING PARATHYROID HORMONE

(71) Applicant: Extend Biosciences, Inc., Newton, MA (US)

(72) Inventors: Tarik Soliman, Cambridge, MA (US); Daniel B. Hall, Easton, MA (US); Rachel Covitz, Allston, MA (US); Garry Musso, Harwich, MA (US); Caroline Hill, Jamaica Plain, MA (US); Ahmet Vakkasoglu, Stoneham, MA (US); Poul Strange, Princeton Junction, NJ (US); Tilmann M. Brotz, Berkeley, CA (US)

(73) Assignee: Extend Biosciences, Inc., Newton, MA (US)

( * ) Notice: Subject to any disclaimer, the term of this patent is extended or adjusted under 35 U.S.C. 154(b) by 0 days.

(21) Appl. No.: 18/368,347

(22) Filed: Sep. 14, 2023

(65) Prior Publication Data
US 2024/0139289 A1   May 2, 2024

Related U.S. Application Data

(60) Provisional application No. 63/464,495, filed on May 5, 2023, provisional application No. 63/412,291, filed on Sep. 30, 2022.

(51) Int. Cl.
*A61K 38/29* (2006.01)
*A61K 47/55* (2017.01)
*A61K 47/60* (2017.01)

(52) U.S. Cl.
CPC ............ *A61K 38/29* (2013.01); *A61K 47/551* (2017.08); *A61K 47/60* (2017.08)

(58) Field of Classification Search
None
See application file for complete search history.

(56) References Cited

U.S. PATENT DOCUMENTS

| | | |
|---|---|---|
| 4,179,337 A | 12/1979 | Davis |
| 4,292,250 A | 9/1981 | DeLuca et al. |
| 4,410,515 A | 10/1983 | Holick et al. |
| 4,456,553 A | 6/1984 | Oshida et al. |
| 4,675,189 A | 6/1987 | Kent et al. |
| 4,816,567 A | 3/1989 | Cabilly et al. |
| 5,108,921 A | 4/1992 | Low et al. |
| 5,116,964 A | 5/1992 | Capon et al. |
| 5,122,614 A | 6/1992 | Zalipsky |
| 5,214,170 A | 5/1993 | Tanabe et al. |
| 5,232,836 A | 8/1993 | Bouillon et al. |
| 5,416,016 A | 5/1995 | Low et al. |
| 5,428,023 A | 6/1995 | Russell-Jones et al. |
| 5,447,851 A | 9/1995 | Beutler et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,569,825 A | 10/1996 | Lonberg et al. |
| 5,574,018 A | 11/1996 | Habberfield et al. |
| 5,605,690 A | 2/1997 | Jacobs et al. |
| 5,625,126 A | 4/1997 | Lonberg et al. |
| 5,629,384 A | 5/1997 | Veronese et al. |
| 5,633,425 A | 5/1997 | Lonberg et al. |
| 5,661,016 A | 8/1997 | Lonberg et al. |
| 5,688,488 A | 11/1997 | Low et al. |
| 5,691,328 A | 11/1997 | Peterson et al. |
| 5,714,142 A | 2/1998 | Blaney et al. |
| 5,739,277 A | 4/1998 | Presta et al. |
| 5,767,254 A | 6/1998 | Polt |
| 5,869,466 A | 2/1999 | Russell-Jones et al. |
| 5,876,969 A | 3/1999 | Fleer et al. |
| 5,919,452 A | 7/1999 | Le et al. |
| 5,932,462 A | 8/1999 | Harris et al. |
| 6,093,701 A | 7/2000 | Wolff et al. |

(Continued)

FOREIGN PATENT DOCUMENTS

| | | |
|---|---|---|
| CA | 2463072 C | 8/2010 |
| CA | 2966207 A1 | 6/2016 |

(Continued)

OTHER PUBLICATIONS

Goodson et al. "Site Directed Pegylation of Recombinant Interleukin-2 At Its Glycosylation Site," Nature Biotechnology, vol. 8, Apr. 1990.
Guo et al. "Prolonged Pharmacokinetic and Pharmacodynamic Actions of a Pegylated Parathyroid Hormone (1-34) Peptide Fragment," Journal of Bone and Mineral Research, vol. 32, No. 1, Jan. 2017.
Krishnan et al. "Repurposing a novel parathyroid hormone (PTH) analog to treat hypoparathyroidism," British Journal of Pharmacology, 2017.
Na et al. "Capillary electrophoretic characterization of PEGylated human parathyroid hormone with matrix-assisted laser desorption/ionization time-of-Xight mass spectrometry," Analytical Biochemistry 331, 2004.
El-Nachef et al. Microwave-Assisted Formation of Peptide-Vitamin Congugates. Eur. J. Org. Chem. 4412-2219, (2012).

(Continued)

*Primary Examiner* — Maury A Audet
(74) *Attorney, Agent, or Firm* — Kaplan IP Law, P.C.; Jonathan M. Kaplan

(57) ABSTRACT

The invention provides a long-acting parathyroid hormone peptide (PTH) that is retained in a subject's blood serum for periods of time that greatly exceed the natural hormone. The long-acting PTH is conjugated to at the carbon 3 position of a non-hormonal vitamin D via a scaffold of discreet length that facilitates its purification, detection, solubility, and efficacy at the PTH receptor (PTHR). The PTH may be conjugated to the non-hormonal vitamin D via a 36 mer poly(ethylene glycol) moiety (PTH-PEG36-VitD). The invention also provides optimized manufacturing methods and formulations. The PTH-PEG36-VitD has a vastly-improved serum half-life and bioavailability when compared to a non-conjugated PTH peptide. PTH-PEG36-VitD also significantly increases serum calcium, reduces urinary calcium, and reduces serum phosphate.

12 Claims, 25 Drawing Sheets

Specification includes a Sequence Listing.

(56) References Cited

U.S. PATENT DOCUMENTS

| | | |
|---|---|---|
| 6,100,294 A | 8/2000 | Reddy |
| 6,103,709 A | 8/2000 | Norman et al. |
| 6,121,312 A | 9/2000 | Reddy |
| 6,329,357 B1 | 12/2001 | Norman et al. |
| 6,342,225 B1 | 1/2002 | Jones et al. |
| 6,395,492 B1 | 5/2002 | Manoharan et al. |
| 6,455,714 B1 | 9/2002 | Holick et al. |
| 6,479,538 B1 | 11/2002 | Reddy |
| 6,516,294 B1 | 2/2003 | Norman |
| 6,660,843 B1 | 12/2003 | Feige et al. |
| 6,713,280 B1 | 3/2004 | Huang et al. |
| 6,756,480 B2 | 6/2004 | Kostenuik et al. |
| 6,787,660 B1 | 9/2004 | Armbruster et al. |
| 6,858,227 B1 | 2/2005 | Lal et al. |
| 6,858,595 B2 | 2/2005 | Hayes |
| 6,887,470 B1 | 5/2005 | Bridon et al. |
| 6,908,963 B2 | 6/2005 | Roberts |
| 6,929,797 B2 | 8/2005 | Mazess et al. |
| 6,989,377 B2 | 1/2006 | Hayes |
| 7,045,318 B2 | 5/2006 | Ballance |
| 7,049,285 B2 | 5/2006 | Park |
| 7,057,012 B1 | 6/2006 | Gardella |
| 7,078,496 B2 | 7/2006 | Roberts |
| 7,141,547 B2 | 11/2006 | Rosen et al. |
| 7,176,278 B2 | 2/2007 | Prior |
| 7,186,797 B2 | 3/2007 | West et al. |
| 7,217,689 B1 | 5/2007 | Elliott et al. |
| 7,244,834 B2 | 7/2007 | Gardella |
| 7,256,253 B2 | 8/2007 | Bridon et al. |
| 7,371,721 B2 | 5/2008 | Henriksen |
| 7,390,509 B2 | 6/2008 | Giordano |
| 7,402,662 B2 | 7/2008 | Athwal |
| 7,511,095 B2 | 3/2009 | Roberts |
| 7,557,183 B2 | 7/2009 | DiMarchi |
| 7,560,123 B2 | 7/2009 | Giordano |
| 7,579,324 B2 | 8/2009 | Burnet et al. |
| 7,601,332 B2 | 10/2009 | Vlahov et al. |
| 7,608,681 B2 | 10/2009 | Dennis et al. |
| 7,741,286 B2 | 6/2010 | Bridon et al. |
| 7,741,453 B2 | 6/2010 | Erickson et al. |
| 7,803,777 B2 | 9/2010 | DeFrees |
| 7,820,179 B2 | 10/2010 | Brown-Augsburger et al. |
| 7,834,088 B2 | 11/2010 | Roberts |
| 7,947,280 B2 | 5/2011 | Ashley et al. |
| 7,982,018 B2 | 7/2011 | Ulich et al. |
| 8,071,678 B2 | 12/2011 | Roberts |
| 8,076,476 B2 | 12/2011 | Reeves et al. |
| 8,101,587 B2 | 1/2012 | Giordano |
| 8,129,348 B2 | 3/2012 | Besman et al. |
| 8,178,495 B2 | 5/2012 | Chilkoti |
| 8,188,064 B2 | 5/2012 | Clagett-Dame |
| 8,188,223 B2 | 5/2012 | Beirnaert et al. |
| 8,252,755 B2 | 8/2012 | Yamada et al. |
| 8,329,876 B2 | 12/2012 | Roberts |
| 8,551,937 B2 | 10/2013 | Wakabayashi et al. |
| 8,609,629 B2 | 12/2013 | Giordano |
| 8,779,109 B2 | 7/2014 | Behrens et al. |
| 8,785,603 B2 | 7/2014 | Sahakian et al. |
| 8,796,443 B2 | 8/2014 | Khvorova et al. |
| 8,968,790 B2 | 3/2015 | Mousa |
| 8,993,248 B2 | 3/2015 | Beckert |
| 9,062,300 B2 | 6/2015 | Gensure et al. |
| 9,173,950 B2 | 11/2015 | Soliman et al. |
| 9,271,519 B2 | 3/2016 | Giordano |
| 9,289,507 B2 | 3/2016 | Soliman et al. |
| 9,585,934 B2 | 3/2017 | Soliman et al. |
| 9,616,109 B2 | 4/2017 | Soliman et al. |
| 9,789,197 B2 | 10/2017 | Soliman et al. |
| 9,863,963 B2 | 1/2018 | Poppe |
| 9,884,124 B2 | 2/2018 | Soliman et al. |
| 9,897,615 B2 | 2/2018 | Martens |
| 10,046,058 B2 | 8/2018 | Rosendahl |
| 10,222,388 B2 | 3/2019 | Soskic et al. |
| 10,406,202 B2 | 9/2019 | Soliman et al. |
| 10,420,819 B2 | 9/2019 | Soliman et al. |
| 10,702,574 B2 | 7/2020 | Soliman et al. |
| 11,116,816 B2 | 9/2021 | Soliman et al. |
| 11,590,207 B2 | 2/2023 | Holten-Andersen et al. |
| 11,918,628 B2 | 3/2024 | Sproge et al. |
| 2001/0007907 A1 | 7/2001 | Reddy |
| 2002/0136731 A1 | 9/2002 | Mazess et al. |
| 2002/0141996 A1 | 10/2002 | Le et al. |
| 2003/0105224 A1 | 6/2003 | Roberts |
| 2003/0113305 A1 | 6/2003 | Osborne et al. |
| 2003/0125309 A1 | 7/2003 | Reddy |
| 2003/0129194 A1 | 7/2003 | Mazess et al. |
| 2003/0171605 A1 | 9/2003 | Reddy |
| 2003/0195171 A1 | 10/2003 | Daifotis |
| 2003/0203359 A1 | 10/2003 | Uhlmann et al. |
| 2004/0132104 A1 | 7/2004 | Sackrison et al. |
| 2004/0186063 A1 | 9/2004 | Gutke et al. |
| 2005/0059129 A1 | 3/2005 | Park |
| 2005/0119242 A1 | 6/2005 | Deluca |
| 2005/0148763 A1 | 7/2005 | Sekimori |
| 2005/0176685 A1 | 8/2005 | Daifotis |
| 2005/0192256 A1 | 9/2005 | Melnick |
| 2005/0260237 A1 | 11/2005 | Byun et al. |
| 2005/0261250 A1 | 11/2005 | Daifotis |
| 2005/0276843 A1 | 12/2005 | Quay |
| 2006/0045880 A1 | 3/2006 | Krieg |
| 2006/0069021 A1 | 3/2006 | Costantino |
| 2006/0153839 A1 | 7/2006 | Mohamed et al. |
| 2006/0199765 A1 | 9/2006 | Gardella |
| 2006/0258630 A1 | 11/2006 | Adorini |
| 2007/0032461 A1 | 2/2007 | Adorini |
| 2007/0249571 A1 | 10/2007 | Tamarkin |
| 2008/0064668 A1 | 3/2008 | Uskokovic |
| 2008/0188548 A1 | 8/2008 | Reddy |
| 2008/0199960 A1 | 8/2008 | Juliano et al. |
| 2008/0242595 A1 | 10/2008 | Doyle |
| 2008/0280859 A1 | 11/2008 | Adorini |
| 2008/0318911 A1 | 12/2008 | Uskokovic |
| 2009/0099140 A1 | 4/2009 | Jankowski |
| 2009/0131360 A1 | 5/2009 | Woolf et al. |
| 2009/0176253 A1 | 7/2009 | Bieniarz et al. |
| 2009/0247544 A1 | 10/2009 | Morgan |
| 2009/0298799 A1 | 12/2009 | Adorini |
| 2009/0298800 A1 | 12/2009 | Uskokovic |
| 2009/0305986 A1 | 12/2009 | Belouski et al. |
| 2009/0324745 A1 | 12/2009 | Giordano |
| 2010/0015046 A1 | 1/2010 | Govindan et al. |
| 2010/0074885 A1 | 3/2010 | Schiff et al. |
| 2010/0098779 A1 | 4/2010 | Balzer |
| 2010/0104626 A1 | 4/2010 | Leamon et al. |
| 2010/0168033 A1 | 7/2010 | Ghigo et al. |
| 2010/0234303 A1 | 9/2010 | Millar et al. |
| 2010/0260836 A1 | 10/2010 | Giordano |
| 2010/0310678 A1 | 12/2010 | Giordano |
| 2010/0323973 A1 | 12/2010 | Leamon et al. |
| 2011/0028394 A1 | 2/2011 | Karim |
| 2011/0166063 A1 | 7/2011 | Bossard et al. |
| 2011/0268793 A9 | 11/2011 | Giordano |
| 2011/0293579 A1 | 12/2011 | Nielsen et al. |
| 2011/0312027 A1 | 12/2011 | Young et al. |
| 2012/0028887 A1 | 2/2012 | Shai et al. |
| 2012/0121726 A1 | 5/2012 | Giordano |
| 2012/0129766 A1 | 5/2012 | Boettcher et al. |
| 2012/0129767 A1 | 5/2012 | Tulipano et al. |
| 2012/0165377 A1 | 6/2012 | Takizawa et al. |
| 2012/0177646 A1 | 7/2012 | Belouski et al. |
| 2013/0085121 A1 | 4/2013 | Wang |
| 2013/0116180 A1 | 5/2013 | Gardella et al. |
| 2013/0129724 A1 | 5/2013 | Boettcher et al. |
| 2013/0143241 A1 | 6/2013 | Martens |
| 2013/0149385 A1 | 6/2013 | Mousa |
| 2013/0164310 A1 | 6/2013 | Annathur et al. |
| 2013/0172251 A1 | 7/2013 | Kangawa et al. |
| 2013/0231277 A1 | 9/2013 | Mohammadi et al. |
| 2013/0261013 A1 | 10/2013 | Baltzer et al. |
| 2013/0295593 A1 | 11/2013 | Beckert |
| 2013/0331316 A1 | 12/2013 | Mohammadi et al. |
| 2014/0050802 A1 | 2/2014 | Balzer |
| 2014/0058063 A1 | 2/2014 | Mahov et al. |
| 2014/0106027 A1 | 4/2014 | Giordano |

(56) References Cited

U.S. PATENT DOCUMENTS

| | | | |
|---|---|---|---|
| 2014/0135260 A1 | 5/2014 | Dong et al. | |
| 2014/0170704 A1 | 6/2014 | Young et al. | |
| 2014/0179560 A1 | 6/2014 | Olson et al. | |
| 2014/0194352 A1 | 7/2014 | Ling et al. | |
| 2014/0200261 A1 | 7/2014 | Hoge et al. | |
| 2014/0213512 A1 | 7/2014 | Ellison et al. | |
| 2014/0256626 A1 | 9/2014 | Santi et al. | |
| 2014/0275489 A1 | 9/2014 | Stevis et al. | |
| 2014/0323396 A1 | 10/2014 | Belouski et al. | |
| 2014/0370616 A1 | 12/2014 | Gupta | |
| 2015/0065420 A1 | 3/2015 | Soliman et al. | |
| 2015/0104469 A1 | 4/2015 | Soliman et al. | |
| 2016/0047825 A1 | 2/2016 | Poppe | |
| 2016/0113993 A1* | 4/2016 | Soliman | A61K 9/0019 530/327 |
| 2016/0114001 A1 | 4/2016 | Soliman et al. | |
| 2016/0114049 A1 | 4/2016 | Soliman et al. | |
| 2016/0144049 A1 | 5/2016 | Soliman et al. | |
| 2016/0151510 A1 | 6/2016 | Rosendahl | |
| 2016/0151511 A1 | 6/2016 | Rosendahl | |
| 2016/0195556 A1 | 7/2016 | Soskic | |
| 2017/0115313 A9 | 4/2017 | Soskic | |
| 2017/0216449 A1 | 8/2017 | Soliman et al. | |
| 2017/0252410 A1 | 9/2017 | Soliman et al. | |
| 2018/0271792 A1 | 9/2018 | Mantripragada | |
| 2018/0311307 A1 | 11/2018 | Soliman et al. | |
| 2018/0318429 A1 | 11/2018 | Rosendahl | |
| 2019/0183966 A1 | 6/2019 | Soliman et al. | |
| 2020/0405820 A1 | 12/2020 | Gardella et al. | |
| 2021/0008153 A1 | 1/2021 | Soliman et al. | |
| 2021/0196801 A1 | 7/2021 | Sproge et al. | |
| 2022/0088149 A1 | 3/2022 | Skands et al. | |
| 2022/0409697 A1 | 12/2022 | Barron et al. | |
| 2023/0218722 A1 | 7/2023 | Sproge et al. | |

FOREIGN PATENT DOCUMENTS

| | | |
|---|---|---|
| CN | 100381177 C | 4/2008 |
| EP | 0312360 B1 | 6/1992 |
| EP | 0486525 B1 | 6/1994 |
| EP | 0804456 B1 | 8/2002 |
| EP | 1477496 A1 | 11/2004 |
| EP | 0981523 B1 | 12/2005 |
| EP | 1151102 B1 | 4/2006 |
| EP | 1434589 B1 | 12/2008 |
| EP | 1931711 B1 | 4/2009 |
| EP | 2085406 A1 | 8/2009 |
| EP | 1601646 B1 | 7/2011 |
| EP | 2372365 A1 | 10/2011 |
| EP | 2423233 A2 | 2/2012 |
| EP | 2288375 B1 | 4/2012 |
| EP | 2481427 A1 | 8/2012 |
| EP | 2530068 A1 | 12/2012 |
| EP | 2316854 B1 | 12/2013 |
| EP | 2695617 A2 | 2/2014 |
| EP | 3030243 B1 | 7/2017 |
| WO | 199110741 A1 | 7/1991 |
| WO | 1992014493 A1 | 9/1992 |
| WO | 1992016221 A1 | 10/1992 |
| WO | 1993007883 A1 | 4/1993 |
| WO | 1993012145 A1 | 6/1993 |
| WO | 1995010302 A1 | 4/1995 |
| WO | 1996033735 A1 | 10/1996 |
| WO | 1996034096 A1 | 10/1996 |
| WO | 1997034637 A2 | 9/1997 |
| WO | 1998024893 A2 | 6/1998 |
| WO | 9916452 A1 | 4/1999 |
| WO | 9967211 | 12/1999 |
| WO | 1999061055 A1 | 12/1999 |
| WO | 0039278 A2 | 7/2000 |
| WO | 2000066090 A1 | 11/2000 |
| WO | 2000074721 A1 | 12/2000 |
| WO | 2000069900 A3 | 2/2001 |
| WO | 2001045746 A3 | 10/2001 |
| WO | 2002062844 A2 | 8/2002 |
| WO | 2002066511 A2 | 8/2002 |
| WO | 2002076489 A1 | 10/2002 |
| WO | 2003011213 A2 | 2/2003 |
| WO | 2002046227 A3 | 4/2003 |
| WO | 2003031581 A2 | 4/2003 |
| WO | 2003025139 A3 | 8/2003 |
| WO | 2003086415 A1 | 10/2003 |
| WO | 2004009124 A2 | 1/2004 |
| WO | 2004011498 A3 | 6/2004 |
| WO | 2004041865 A3 | 7/2004 |
| WO | 2004069159 | 8/2004 |
| WO | 2004080922 A2 | 9/2004 |
| WO | 2004084948 A1 | 10/2004 |
| WO | WO2005027978 A2 | 3/2005 |
| WO | 2005051323 A2 | 6/2005 |
| WO | 2005097158 A1 | 10/2005 |
| WO | WO2005099768 A2 | 10/2005 |
| WO | 2005105071 A1 | 11/2005 |
| WO | 2005117906 A1 | 12/2005 |
| WO | 2006117684 A1 | 11/2006 |
| WO | 2007012188 A1 | 2/2007 |
| WO | 2007035922 A2 | 3/2007 |
| WO | 2007038250 A2 | 4/2007 |
| WO | 2007049941 A1 | 5/2007 |
| WO | 2006116156 A3 | 10/2007 |
| WO | 2007097934 A3 | 11/2007 |
| WO | 2007103455 A3 | 11/2007 |
| WO | 2008036841 A3 | 10/2008 |
| WO | 2008118013 A2 | 10/2008 |
| WO | WO2009095479 A2 | 8/2009 |
| WO | 2009121884 A1 | 10/2009 |
| WO | WO2011012719 A1 | 2/2011 |
| WO | WO2011012721 A1 | 2/2011 |
| WO | WO2011012723 A1 | 2/2011 |
| WO | WO2011042450 A1 | 4/2011 |
| WO | WO2011089215 A1 | 7/2011 |
| WO | WO2011089216 A1 | 7/2011 |
| WO | 2011122948 A1 | 10/2011 |
| WO | 2011146902 A1 | 11/2011 |
| WO | 2011123813 A3 | 12/2011 |
| WO | 2012041451 A1 | 4/2012 |
| WO | 2012129650 A1 | 10/2012 |
| WO | 2012158962 A2 | 11/2012 |
| WO | 2012163563 A1 | 12/2012 |
| WO | WO2011089214 A1 | 2/2013 |
| WO | WO2013024049 A1 | 2/2013 |
| WO | WO2013024051 A1 | 2/2013 |
| WO | WO2013024053 A1 | 2/2013 |
| WO | 2013033230 A1 | 3/2013 |
| WO | 2013044356 A1 | 4/2013 |
| WO | WO2013053856 A1 | 4/2013 |
| WO | 2013044356 A9 | 5/2013 |
| WO | 2013086313 A1 | 6/2013 |
| WO | 2013102149 A1 | 7/2013 |
| WO | 2013163162 A1 | 10/2013 |
| WO | WO2013172967 A1 | 11/2013 |
| WO | 2014041024 A1 | 3/2014 |
| WO | WO2014033540 A2 | 3/2014 |
| WO | WO2014056915 A1 | 4/2014 |
| WO | WO2014056923 A1 | 4/2014 |
| WO | WO2014056926 A1 | 4/2014 |
| WO | 2013040093 A3 | 5/2014 |
| WO | 2014081864 A1 | 5/2014 |
| WO | 2014083427 A2 | 6/2014 |
| WO | WO2014086961 A1 | 6/2014 |
| WO | WO2014173759 A1 | 10/2014 |
| WO | 2015057836 A2 | 4/2015 |
| WO | 2015057836 A3 | 4/2015 |
| WO | WO2015052155 A1 | 4/2015 |
| WO | WO2016020373 A1 | 2/2016 |
| WO | 2016065052 | 4/2016 |
| WO | WO2016065042 * | 4/2016 |
| WO | WO2016073435 A1 | 5/2016 |
| WO | 2016089818 A1 | 6/2016 |
| WO | WO2016110577 A1 | 7/2016 |
| WO | 2017148883 A1 | 9/2017 |
| WO | 2018060312 A1 | 4/2018 |
| WO | WO2018060310 A1 | 4/2018 |

(56) References Cited

FOREIGN PATENT DOCUMENTS

| WO | WO2018060311 A1 | 4/2018 |
| WO | 2018175250 A1 | 9/2018 |
| WO | WO2021077058 * | 4/2021 |
| WO | 2021242756 | 12/2021 |

OTHER PUBLICATIONS

Kostenuik et al. Infrequent Delivery of a Long-Acting PTH-Fc Fusion Protein Has Potent Anabolic Effects on Cortical and Cancellous Bone. Journal of Bone and Mineral Research, vol. 22, No. 10 (2007).

Vallinayagam, Ramakrishnan et al. "Novel Bioconjugates of Aminolevulinic Acid with Vitamins," Organic Letters, vol. 10, No. 20, 4453-4455, 2008.

El Nachef, Claudia, Benzotriazole-mediated Syntheses of Peptides, Peptide Conjugates and Peptidomimetics,A Dissertation Presented to the Graduate School of the University 2011.

Silva et al., "Catabolic and anabolic actions of parathyroid hormone on the skeleton," J. Endocrinol. Invest. 34(10):801-810 (2011).

Speeckaert et al., "Biological and clinical aspects of the vitamin D binding protein (Gc-globulin) and its polymorphism," Clinica Chimica Acta 372:33-42 (2006).

Uy, R. and Wold, F. "Posttranslational Covalent Modification of Proteins," (1977) Science 198:890-6.

Winer et al., "Long-Term Parathyroid Hormone 1-34 Replacement Therapy in Children with Hypoparathyroidism," J. Pediatr. 203:391-9 (2018).

Abe et.al., Synthetic analogues of vitamin D3 with an oxygen atom in the side chain skeleton, FEBS Lett. 226:58-62 (1987).

Addo JK, et al., 2002, "The C19 Position of 25-Hydroxyvitamin D3 Faces Outward in the Vitamin D Sterol-Binding Pocket of Vitamin D-Binding Protein," Bioorganic & Medicinal Chemistry Letters 12: 279-281.

Ahsan, F. et al., 2001, Enhanced Bioavailability of Calcitonin Formulated with Alkylglycosides following Nasal and Ocular Administration in Rats, Pharm Res 18:1742-1746.

Amiram M, et al., 2013, "A Depot-Forming Glucagon-Like Peptide-1 Fusion Protein Reduces Blood Glucose for Five Days with a Single Injection," Journal of Controlled Release 172: 144-151.

Amiram M, et al., 2013, "Injectable Protease-Operated Depots of Glucagon-Like Peptide-1 Provide Extended and Tunable Glucose Control," Proceedings of the National Academy of Sciences, USA 110(8): 2792-2797.

Arnaud J and Constans J, 1993, "Affinity Differences for Vitamin D Metabolites Associated with the Genetic Isoforms of the Human Serum Carrier Protein (DBP)," Human Genetics 92: 183-188.

Arnold, JJ et al., 2004, Correlation of Tetradecylmaltoside Induced Increases in Nasal Peptide Drug Delivery with Morphological Changes in Nasal Epithelial Cells, J Pharm Sci 93: 2205-13.

Arnusch CJ, et al., 2012, "Ultrashort Peptide Bioconjugates Are Exclusively Antifungal Agents and Synergize with Cyclodextrin and Amphotericin B," Antimicrobial Agents and Chemotherapy 56(1) 1-9.

Baggio LL, et al., 2004, "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," Diabetes 53: 2492-2500.

Bailon P, et al., 2001, "Rational Design of a Potent, Long-Lasting Form of Interferon: a 40 kDa Branched Polyethylene Glycol-Conjugated Interferon Alpha-2a for the Treatment of Hepatitis C," Bioconjugate Chemistry 12(2): 195-202.

Bao W, et al., 2013, "Novel Fusion of GLP-1 with a Domain Antibody to Serum Albumin Prolongs Protection against Myocardial Ischemia/Reperfusion Injury in the Rat," Cardiovascular Diabetology 12: 148.

Barrington P, et al., 2011, "A 5-Week Study of the Pharmacokinetics and Pharmacodynamics of LY2189265, a Novel, Long-Acting Glucagon-Like Peptide 1 Analogue, in Patients with Type 2 Diabetes," Diabetes, Obesity, and Metabolism 13:426-433.

Barrington P, et al., 2011, "LY2189265, a Long-Acting Glucagon-Like Peptide 1 Analogue, Showed a Dose-Dependent Effect on Insulin Secretion in Healthy Patients," Diabetes, Obesity, and Metabolism 13:434-438.

Ben-Shabat S, et al., 2005, "Vitamin D3-Based Conjugates for Topical Treatment of Psoriasis: Synthesis, Antiproliferative Activity, and Cutaneous Penetration Studies," Pharmaceutical Research 22(1): 50-57.

Bishop JE, et al., 1994, "Profile of Ligand Specificity of the Vitamin D Binding Protein for 1alpha-25-dihydroxyvitamin D3 and its Analogues," Journal of Bone and Mineral Research 9(8): 1277-1288.

Blouch K, et al., 1997, "Molecular Configuration and Glomerular Size Selectivity in Healthy and Nephrotic Humans," American Journal of Physiology 273 (Renal Physiology 42): F430-F437. (May 20, 1997).

Boerner et al., HUMAN mAb From in Vitro-Primed Lymphocytes, J. Immunol, 147: 86-95 (1991).

Bouillon R, et al., 1980, "Comparative Study of the Affinity of the Serum Vitamin D Binding Protein," Journal of Steroid Biochemistry 13: 1029-1034.

Bouillon R, et al., 1991, "Vitamin D Analogues with Low Affinity for the Vitamin D Binding Protein: Enhanced in Vitro and Decreased in Vivo Activity," Journal of Bone and Mineral Research 6(10): 1051-1057.

Bouman-Theo E, et al., 2008, "A Phase I, Single and Fractionated, Ascending-Dose Study Evaluating the Safety, Pharmacokinetics, Pharmacodynamics, and Immunogenicity of an Erythropoietin Mimetic Antibody Fusion Protein (CNTO 528) in Healthy Male Subjects," Journal of Clinical Pharmacology 48: 1197-1207.

Cai Y, et al., 2013, "Long-Acting Preparations of Exenatide," Drug Design, Development, and Therapy 7: 963-970.

Camacho RC, et al., 2013, "PEGylated FGF21 Rapidly Normalizes Insulin-Stimulated Glucose Utilization in Diet-Induced Insulin Resistant Mice," European Journal of Pharmacology 715: 41-45.

Capon DJ, et al., 1989, "Designing CD4 Immunoadhesions for AIDS Therapy," Nature 337: 525-531.

Carlberg C, 2003, "Molecular Basis for the Selective Activity of Vitamin D Analogues," Journal of Cellular Biochemistry 88: 274-281.

Chae SY, et al., 2009, "Pharmacokinetic and Pharmacodynamic Evaluation ofSite-Specific PEGylated Glucagon-Like Peptide-1 Analogs asFlexible Postprandial-Glucose Controllers," Journal of Pharmaceutical Sciences 98(4): 1556-1567.

Chae SY, et al., 2010, "Biochemical, Pharmaceutical, and Therapeutic Properties of Long-Acting Lithocholic Acid Derivatized Exendin-4 Analogues," Journal of Controlled Release 142: 206-213.

Chae SY, et al., 2010, "The Fatty Acid Conjugated Exendin-4 Analogues for Type 2 Antidiabetic Therapeutics," Journal of Controlled Release 144: 10-16.

Chalasani KB, et al., 2007, "Effective Oral Delivery of Insulin in Animal Models Using Vitamin B12-coated Dextran Nanoparticles," Journal of Controlled Release 122: 141-150.

Chen et al., Selection and Analysis of an Optimized Anti-VEGF Antibody: Crystal Structure of an Affinity-matured Fab, J. Mol. Biol. 293:865-881 (1999).

Chen S, et al., 2010, "Mechanism-Based Tumor-Targeting Drug Delivery System. Validation of Efficient Vitamin Receptor-Mediated Endocytosis and Drug Release," Bioconjugate Chemistry 21: 979-987.

Choi H-I, et al., 2009, "A Novel L-Ascorbic Acid and Peptide Conjugate with Increased Stability and Collagen Biosynthesis," BMB Reports 42(11): 743-746.

Clackson et al., Making antibody fragments using phage display libraries, Nature, 352: 624-628 (1991).

Clardy-James S, et al., 2013, "Synthesis, Characterization, and Pharmacodynamics of Vitamin-B12-Conjugated Glucagon-Like Peptide-1," ChemMedChem 8: 582-586.

(56) References Cited

OTHER PUBLICATIONS

Clark et al. Long-acting Growth Hormones Produced by Conjugation with Polyethylene Glycol*, J. Biol. Chem. 271:21969-21977 (1996).

Cleland JL, et al., 2012, "A Novel Long-Acting Human Growth Hormone Fusion Protein (VRS-317): Enhanced in Vivo Potency and Half-Life," Journal of Pharmaceutical Sciences 101(8): 2744-2754.

Clemens TL, et al., 1983, "A Simple Method for Generation of Antibodies with Specificity for 1,25-Dihydroxyergocalciferol and 1,25-Dihydroxycholecalciferol," Steroids 42(5): 503-509.

Conforti A, et al., 1987, "PEG Superoxide Dismutase Derivatives: Anti-Inflammatory Activity in Carrageenan Pelurisy in Rats," Pharmacological Research Communications 19: 287-294.

Cooke NE and Haddad JG, 1989, "Vitamin D Binding Protein (Gc-Globulin)," Endocrinology Reviews 10: 294-307.

Datta-Mannan A, et al., 2012, "Influence of improved FcRn binding on the subcutaneous bioavailability of monoclonal antibodies in cynomolgus monkeys," MAbs. 4(2):267-73.

de Schepper J, et al., 2011, "Long-Acting PEGylated Human GH in Children with GH Deficiency: A Single-Dose, Dose-Escalation Trial Investigating Safety, Tolerability, Pharmacokinetics and Pharmacodynamics," European Journal of Endocrinology 165(3): 401-409.

de Smidt PC, et al., 1991, "Association of Antisense Oligonucleotides with Lipoproteins Prolongs the Plasma Half-Life and Modifies the Tissue Distribution," Nucleic Acids Research 19(17): 4695-4700.

DeLuca HF, 2008, "Evolution of our Understanding of Vitamin D," Nutrition Reviews 66(suppl. 2): S73-8.

Dennis MS, et al., 2002, "Albumin Binding as a General Strategy for Improving the Pharmacokinetics of Proteins," Journal of Biological Chemistry 277: 35035-35043.

Dennis MS, et al., 2007, "Imaging Tumors with an Albumin-Binding Fab, a Novel Tumor-Targeting Agent," Cancer Research 67: 254-261.

Ding S, et al., 2014, "Multivalent Antiviral XTEN-Peptide Conjugates with Long in Vivo Half-Life and Enhanced Solubility," Bioconjugate Chemistry 25(7): 1351-9.

Doores, K., et al., "Direct deprotected glycosyl-asparagine ligation" Chem. Commun., 1401-1403, 2006.

Elliott S, et al., 2003, "Enhancement of in Vivo Therapeutic Protein Activities through Glycoengineering," Nature Biotechnology 21: 414-421.

Hernandez-Martin, et al. "Synthesis of vitamin D3 analogues with A-ring modifications to directly measure vitamin D levels in biological samples," Bioorganic & Medicinal Chemistry 21, Oct. 2013.

PCT Search Report and Written Opinion for PCT application No. PCT/US2015/056737, mailed on Mar. 31, 2016.

PCT Search Report and Written Opinion for PCT application No. PCT/US2015/056723, mailed on Mar. 31, 2016.

PCT Invitation to Pay Additional Fees for PCT application No. PCT/US2015/056737, mailed on Feb. 3, 2016.

PCT Invitation to Pay Additional Fees for PCT application No. PCT/US2015/056723, mailed on Feb. 3, 2016.

Ray, Rahul et al. "Photoaffinity Labeling of the Rat Plasma Vitamin D Binding Protein with [26,27-3H]-25-Hydroxyvitamin D3 3B-[N-(4-Azido-2-nitrophenyl)glycinate]," Biochemistry, vol. 25, No. 17, 1986.

Roy, Aloka et al. "Aminopropylation of vitamin D hormone (1a,25-dihydroxyvitamin D3), its biological precursors, and other steroidal alcohols: An anchoring moiety for affinity studies of sterols," Steroids 60:530-533, 1995.

Norman, Anthony W. "From vitamin D to hormone D: fundamentals of the vitamin D endocrine system essential for good health," The American Journal of Clinical Nutrition, 88(suppl.), 491S-499S, 2008.

Erben and Musculoskel, "Vitamin D analogs and bone," Neuron Interact. 2(1):59-69 (2001).

Fellouse, "Synthetic antibodies from a four-amino-acid code: A dominant role for tyrosine in antigen recognition," Proc. Natl. Acad. Sci. USA 101(34): 12467-12472 (2004).

Fishburn, "The Pharmacology of PEGylation: Balancing PD with PK to Generate Novel Therapeutics," J. Pharm. Sci. 97:4167-4183 (2008).

Fisher CJ, et al., 1996, "Treatment of Septic Shock with the Tumor Necrosis Factor Receptor: Fc Fusion Protein," The New England Journal of Medicine 334: 1697-1702.

Freeman JN, et al., 2013, "Chronic central ghrelin infusion reduces blood pressure and heart rate despite increasing appetite and promoting weight gain in normotensive and hypertensive rats," Peptides 42: 35-42.

Gabizon A, et al., 2004, "Tumor Cell Targeting of Liposome-Entrapped Drugs with Phospholipid-Anchored Folic Acid-PEG Conjugates," Advanced Drug Delivery Reviews 56: 1177-1192.

Gaich G, et al., 2013, "The Effects of LY2405319, an FGF21 Analog, in Obese Human Subjects with Type 2 Diabetes," Cell Metabolism 18: 333-340.

Garay RP, et al., 2012, "Antibodies against Polyethylene Glycol in Healthy Subjects and in Patients Treated with PEG-Conjugated Agents," Expert Opinion on Drug Delivery 9(11): 1319-1323.

Gong N, et al., 2011, "Site-Specific PEGylation of Exenatide Analogues Markedly Improved Their Glucoregulatory Activity," British Journal of Pharmacology 163: 399-412.

Gourlet, P., et al. (1998), "Interaction of lipophilic VIP derivatives with recombinant VIP rPACAP 1 and VIP rPACAP receptors," Eur J Pharmacol 354: 105-111.

Haddad JG, 1995, "Plasma Vitamin D-Binding Protein (Gc-Globulin): Multiple Tasks," Journal of Steroid Biochemistry and Molecular Biology 53: 579-82.

Haddad JG, et al., 1992, "Identification of the Sterol- and Actin-Binding Domains of Plasma Vitamin D Binding Protein (Gc-Globulin)," Biochemistry 31: 7174-7181.

Haddad JG, et al., 1993, "Human Plasma Transport of Vitamin D After its Endogenous Synthesis," Journal of Clinical Investigation 91: 2552-2555.

Hakimelahi GH, et al., 2001, "Design and Synthesis of a Cephalosporin-Retinoic Acid Prodrug Activated by a Monoclonal Antibody-betaLactamase Conjugate," Bioorganic & Medicinal Chemistry 9: 2139-2147.

Harris JM and Chess RB, 2003, "Effect of PEGylation on Pharmaceuticals," Nature Reviews in Drug Discovery 2: 214-221.

Harris, "Therapeutic Monoclonals," Biochem. Soc. Transactions 23: 1035-1038 (1995).

Harvill ET and Morrison SL, 1995, "An IgG3-IL2 Fusion Protein Activates Complement, Binds Fc(gamma)RI, Generates LAK Activity and Shows Enhanced Binding to the High Affinity IL-2R," Immunotechnology 1: 95-105.

Havelund S, et al., 2004, "The Mechanism of Protraction of Insulin Determir, a Long-Acting Acylated Analog of Human Insulin," Pharmaceutical Research 21(8): 1498-1504.

Herbst RS, 2009, "Safety, Pharmacokinetics, and Antitumor Activity of AMG 386, a Selective Angiopoietin Inhibitor, in Adult Patients with Advanced Solid Tumors," Journal of Clinical Oncology 27: 3557-3565.

Hiura et. al., "Effects of Ghrelin Administration During Chemotherapy With Advanced Esophageal Cancer Patients," Cancer Jan. 26, 2012, http://onlinelibrary.wiley.com/doi/10.1002/cncr.27430/abstract.

Hoffmann E, et al., 2013, "PK Modulation of Haptenylated Peptides via Non-covalent Antibody Complexation," Journal of Controlled Release 171: 48-56.

Holick MF (editor), 2010, "Vitamin D: Physiology, Molecular Biology, and Clinical Applications," Humana Press pp. 0-1155.

Holt LJ, et al., 2008, "Anti-serum Albumin Domain Antibodies for Extending the Life-Time of Short Lived Drugs," Protein Engineering, Design, & Selection 21(5): 283-288.

Hoogenboom et al., "Multi-subunit proteins on the surface of filamentous phage: methodologies for displaying antibody (Fab) heavy and light chains," Nucl. Acids Res., 19: 4133-4137 (1991).

(56) References Cited

OTHER PUBLICATIONS

Huang A, et al., "A Better Anti-Diabetic Recombinant Human Fibroblast Growth Factor 21 (rhFGF21) Modified with Polyethylene Glycol," PLoS ONE 6(6): e20669.
Hurle and Gross, "Protein engineering techniques for antibody humanization," Curr. Op. Biotech. 5:428-433 (1994).
Islam I, et al., 1994, "Evaluation of a Vitamin-Cloaking Strategy for Oligopeptide Therapeutics: Biotinylated HIV1-Protease Inhibitors," Journal of Medicinal Chemistry 37: 293-304.
Itoh N, 2014, "FGF21 as a Hepatokine, Adipokine, and Myokine in Metabolism and Diseases," Frontiers in Endocrinology 5: article 107.
Jain, "PEGylation: An Approach for Drug Delivery. A Review," Crit. Rev. Ther. Drug Carrier Syst. 25:403-447 (2008).
Jakobovits et al., "Analysis of homozygous mutant chimeric mice: Deletion of the immunoglobulin heavy-chain joining region blocks B-cell," Proc. Natl. Acad. Sci USA, 90: 2551 (1993).
Jakobovits et al., "Germ Line Transmission and Expression of a Human-Derived Yeast Artificial Chromosome," Nature 362: 255-258 (1993).
Jevsevar S, et al., 2010, "PEGylation of Therapeutic Proteins," Biotechnology Journal 5: 113-128.
Jia ZQ, et al., 2012, "Cardiovascular Effects of a PEGylated Apelin," Peptides 38: 181-188.
Jones et al., Replacing the Complementarity-determining Regions in a Human Antibody with those from a Mouse, Nature 321 :522-525 (1986).
Katre NV, et al., 1987, "Chemical Modification of Recombinant Interleukin 2 by Polyethylene Glycol Increases its Potency in the Murine Meth A Sarcoma Model," Proceedings of the National Academy of Sciences, USA 84: 1487-1491.
Kaul, R. and Balaram, P. (1999), "Stereochemical Control of Peptide Folding," Bioorg Med Chem 7: 105-117.
Kaya T, et al., 2009, "Covalent Labeling of Nuclear Vitamin D Receptor with Affinity Labeling Reagents Containing a Cross-linking Probe at Three Different Positions of the Parent Ligand: Structural and Biochemical Implications," Bioorganic Chemistry 37: 57-63.
Kharitonenkov A and Adams AC, 2014, "Inventing New Medicines: The FGF21 Story," Molecular Metabolism 3: 221-229.
Kharitonenkov and Shanafelt, Curr. Opin. Investig. Drugs 10:359-364 (2009), Abstract Only.
Kharitonenkov et al., "FGF-21 as a novel metabolic regulator," J. Clin. Invest. 115:1627-1635 (2005).
Kim KH and Lee M-S, 2014, "FGF21 as a Stress Hormone: The Roles of FGF21 in Stress Adaptation and the Treatment of Metabolic Diseases," Diabetes & Metabolism Journal 38: 245-251.
Kliewer and Mangelsdorf, "Fibroblast growth factor 21: from pharmacology to physiology1-4," Am. J. Clin. Nutr. 91:254S-257S (2010).
Knight DM, et al., 1993,"Construction and Initial Characterization of a Mouse-Human Chimeric Anti-TNF Antibody," Molecular Immunology 30(16): 1443-1453.
Knutson et al., Biochem Pharmacol 53: 829 (1997).
Kobayashi N, et al., 1992, "Production and Specificity of Antisera Raised against 25-Hydroxyvitamin D3-[C-3]-Bovine Serum Albumin Conjugates," Steroids 57: 488-493.
Kobayashi N, et al., 1994, "Production of a Group-Specific Antibody to 1alpha, 25-dihydroxyvitamin D and its Derivatives Having the 1alpha, 3beta-dihydroxylated A-Ring Structure," Steroids 59: 404-411.
Kobayashi N, et al., 1994, "Specificity of the Polyclonal Antibodies Raised against a Novel 25-Hydroxyvitamin D3-Bovine Serum Albumin Conjugate Linked through the C11alpha Position," Journal of Steroid Biochemistry & Molecular Biology 48: 567-572.
Kohler et al, "Continuous cultures of fused cells secreting antibody of predefined specificity," Nature, 256: 495 (1975).
Kong J-H, et al., 2010, "Long-Acting Hyaluronate-Exendin 4 Conjugate for the Treatment of Type 2 Diabetes," Biomaterials 31: 4121-4128.

Kontermann R (editor), 2012, "Therapeutic Proteins: Strategies to Modulate Their Plasma Half-lives," Wiley-Blackwell, pp. 0-339.
Kozbor, "A Human Hybrid Myeloma for Production of Human Monoclonal Antibodies," J. Immunol, 133: 3001 (1984).
Kutner A, et al., 1986, "Photoactivable Analogues for Labeling 25-Hydroxyvitamin D3 Serum Binding Protein and for 1,25-Dihydroxyvitamin D3 Intenstinal Receptor Protein," Bioorganic Chemistry 14: 134-147.
Langenheim JF and Chen WY, 2009, "Improving the Pharmacokinetics/Pharmacodynamics of Prolactin, GH, and Their Antagonists by Fusion to a Synthetic Albumin-Binding Peptide," Journal of Endocrinology 203:375-387.
Leamon CP and Low PS, 2001, "Folate-Mediated Targeting: From Diagnostics to Drug and Gene Delivery," Drug Discovery Today 6(1): 44-51.
Leamon CP and Reddy JA, 2004, "Folate-Targeted Chemotherapy," Advanced Drug Delivery Reviews 56: 1127-1141.
Lee et al., "Bivalent antibody phage display mimics natural immunoglobulin," J. Immunol. Methods 284(1-2): 119-132 (2004).
Lee et al., "High-affinity Human Antibodies from Phage-displayed Synthetic Fab Libraries with a Single," J. Mol. Biol. 340(5): 1073-1093 (2004).
Leyssens C, et al., 2014, "The Future of Vitamin D Analogues," Frontiers in Physiology 5: Article 122.
Liang S, et al., 2013, "Structural Basis for Treating Tumor Necrosis Factor alpha (TNFalpha)-associated Diseases with the Therapeutic Antibody Infliximab," Journal of Biological Chemistry 288: 13799-13807.
Liebner R, et al., 2014, "Protein HESylation for Half-Life Extension: Synthesis, Characterization and Pharmacokinetics of HESylated Anakinra," European Journal of Pharmaceutics and Biopharmaceutics 87: 378-385.
Link RP, et al., 1987, "Photoaffinity Labeling of Serum Vitamin D Binding Protein by 3-Deoxy-3-azido-25-hydroxyvitamin D3," Biochemistry 26: 3957-3964.
Lips P, 2006, "Vitamin D Physiology," Progress in Biophysics and Molecular Biology 92: 4-8.
Lonberg 2008, "Fully human antibodies from transgenic mouse and phage display platforms" Curr Opin Immunol. Aug. 2008;20(4):450-9.
Lonberg and Huszar, Intern. Rev. Immunol. 13: 65-93 (1995).
Lonberg et al.,"Antigen-specific human antibodies from mice comprising four distinct genetic modifications," Nature 368: 856-859 (1994).
Lu Y, et al., 2004, "Folate Receptor-Targeted Immunotherapy of Cancer: Mechanism and Therapeutic Potential," Advanced Drug Delivery Reviews 56: 1161-1176.
Makrides SC, et al., 1996, "Extended in Vivo Half-Life of Human Soluble Complement Receptor Type 1 Fused to a Serum Albumin-Binding Receptor," Journal of Pharmacology and Experimental Therapeutics 277(1): 534-542.
Marks et al., "By-passing Immunization Human Antibodies from V-gene Libraries Displayed on Phage," J. Mol. Biol, 222: 581-597 (1991).
Marks et al., "By-Passing Immunization: Building High Affinity Human Antibodies by Chain Shuffling," Bio. Technology 10: 779-783 (1992).
McIntyre et al., "Effects of new analogues of vitamin D on bone cells: Implications for treatment of uremic bone disease," Kidney Int. 55: 500 (1999).
McLeod et al., "The Vitamin D-binding Protein, &-Fetoprotein, Albumin Multigene Family: Detection of Transcripts in Multiple Tissues," J Biol Chem. 264(2):1260-7 (1989).
Mero A, et al., 2013, "Conjugation of Hyaluronan to Proteins," Carbohydrate Polymers 92: 2163-2170.
Misbah S, et al., 2009, "Subcutaneous immunoglobulin: opportunities and outlook," Clinical and Experimental Immunology 158(Suppl 1): 51-59.
Morrison, "Success in Specification," Nature 368: 812-813 (1994).
Mu J, et al, 2012, "FGF21 Analogs of Sustained Action Enabled by Orthogonal Biosynthesis Demonstrate Enhanced Antidiabetic Pharmacology in Rodents," Diabetes 61:505-512.

(56) References Cited

OTHER PUBLICATIONS

Müller DN, et al., 2011, "Vitamin D Review," Journal of the Renin-Angiotensin-Aldosterone System 12: 125-8.
Nanocs PEG Products located at: http://www.nanocs.com/PEG/VTPEG.htm.
Neary NM, et al., 2004, "Ghrelin Increases Energy Intake in Cancer Patients with Impaired Appetite: Acute, Randomized, Placebo-Controlled Trial," The Journal of Clinical Endocrinology & Metabolism 89(6): 2832-2836.
Nestor, J.J., Jr. (2007) Comprehensive Medicinal Chemistry II 2: 573-601.
Neuberger, "Generating high-avidity human Mabs in mice," Nature Biotechnol. 14: 826 (1996).
Norman AW, et al., 2001, "Ligands for the Vitamin D Endocrine System: Different Shapes Function as Agonists and Antagonists for Genomic and Rapid Response Receptors or as a Ligand for the Plasma Vitamin D Binding Protein," Journal of Steroid Biochemistry and Molecular Biology 76: 49-59.
Notice of Allowance dated Jun. 23, 2009, for U.S. Appl. No. 10/765,336.
Ono Y, 2014, "Multifunctional and Potent Roles of the 3-Hydroxypropoxy Group Provide Eldecalcitol's Benefit in Osteoporosis Treatment," Journal of Steroid Biochemistry & Molecular Biology 139: 88-97.
Park S, et al., 2014, "A Novel Delivery Platform for Therapeutic Peptides," Biochemical and Biophysical Research Communications 450(1): 13-18.
Payne RJ, et al., 2004, "Synthesis and Protein Conjugation Studies of Vitamin K Analogues," Bioorganic & Medicinal Chemistry 12: 5785-5791.
Peleg S and Posner GH, 2003, "Vitamin D Analogs as Modulators of Vitamin D Receptor Action," Current Topics in Medicinal Chemistry 3(14): 1555-72.
Petrus AK, et al., 2009, "Exploring the Implications of Vitamin B12 Conjugation to Insulin on Insulin Receptor Binding," ChemMedChem 4: 421-426.
Pfutzner, A and Forst, T, 2005, "Pulmonary insulin delivery by means of the Technosphere™ drug carrier mechanism," Expert Opin Drug Deliv 2:1097-1106.
Presta, "Antibody Engineering," Current Opinion in Biotechnology, 3:394-398 (1992).
Punj V, et al., 2004, "Effect of Vitamin D Analogue (1alpha Hydroxy D5) Immunoconjugated to Her-2 Antibody on Breast Cancer," International Journal of Cancer 108: 922-929.
Rattan, S.I., et al. (1992), "Protein Synthesis, Post translational Modifications, and Aging," Ann N Y Acad Sci 663:48-62.
Ray R, et al., 1986, "Photoaffinity Labeling of the Rat Plasma Vitamin D Binding Protein with [26,27-3H]-25-Hydroxyvitamin D3 3beta-[N-(4-azido-2-nitrophenyl)glycinate]," Biochemistry 25(17): 4729-4733.
Reddy JA, et al., 2007, "Folate Receptor-Specific Antitumor Activity of EC131, a Folate-Maytansinoid Conjugate," Cancer Research 67: 6376-6382.
Revelle et al., "Synthesis and Biological Activity of 3beta-Fluorovitamin D3,: Comparison of the Biological Activity of 3beta-Fluorovitamin D3, and 3-Deoxyvitamin D3," J. Steroid Biochem. 22:469-474 (1985).
Riechmann et al., "Reshaping human antibodies for therapy," Nature 332:323-329 (1988).
Rosenstock J, et al., 2009, "Potential of Albiglutide, a Long-Acting GLP-1 Receptor Agonist, in Type 2 Diabetes," Diabetes Care 32(10): 1880-1886.
Salmaso S, et al., 2009, "Targeting Glioma Cells in Vitro with Ascorbate-Conjugated Pharmaceutical Nanocarriers," Bioconjugate Chemistry 20: 2348-2355.
Sasson K, et al., 2010, "Engineering Prolonged Acting Prodrugs Employing an Albumin-Binding Probe that Undergoes Slow Hydrolysis at Physiological Conditions," Journal of Controlled Release 142: 214-220.

Schlapschy M, et al., 2013," PASylation: A Biological Alternative to PEGylation for Extending the Plasma Half-Life of Pharmaceutically Active Proteins," Protein Engineering, Design & Selection 26: 489-501.
Arrighi et al. Bone Healing Induced by local devlivery of an engineered parathyroid hormone prodrug. Biomaterials, Elsevier Science Publishers BV, Barking, GB, vol. 30, No. 9, pp. 1763-1771, 2009.
Filpula et al. Releasable PEGylation of proteins with customized linkers. Advanced Drug Delivery Reviews, vol. 60, pp. 29-49, 2008.
Levine, Paul M et al. Intrinsic bioconjugation for site-specific protein PEGylation at N-terminal serine. Chem. Commun., vol. 50, 6909, 2014.
Rejnmark et al. PTH replacement therapy of hypoparathyroidism. Osteoporos Int. 24:1529-1536, 2013.
PCT International Search Report and Written Opinion dated Jul. 25, 2017 for PCT/EP2017/054550, filed on Feb. 28, 2017.
PCT International Search Report and Written Opinion dated Nov. 29, 2017 for PCT/EP2017/074594, filed on Sep. 28, 2017.
Higashi, Tatsuya, Enzyme-linked immunosorbent assay for plasma 24,25-dihydroxyvitamin D3, Analytica Chimica Acta 365 (1998) 151-158.
Kobayashi, Norihiro, Specificity of Polyclonal Antibodies Raised against a Novel 24,25-Dihydroxyvitamin D3-Bovine Serum Albumin Conjugant Linked through the C-11alpha or C-3 Position, J. Steroid Biochem. Molec. Biol. vol. 62, No. 1, pp. 79-87, 1997.
Lee et al. N-Terminal Site-Specific Mono-PEGylation of Epidermal Growth Factor, Pharmaceutical Research, vol. 20, No. 5, May 2003.
Okazaki et al., "Prolonged signaling at the parathyroid hormone receptor by peptide ligands targeted to a specific receptor conformation", Proc. Natl. Acad. Sci. U S A. 105(43):16525-30 (2008).
Ponnapakkam et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice" Calcif. Tissue Int. 91(3): 196-203 (2012).
Stratford et al., "Pharmacokinetics in Rats of a Long-Acting Human Parathyroid Hormone-Collagen Binding Domain Peptide Construct", J. Pharm. Sci. 103:768-775 (2014).
Yewle et al., "Bifunctional bisphosphonates for delivering PTH (1-34) to bone mineral with enhanced bioactivity", Biomaterials 34: 3141-3149 (2013).
Leone-Bay et al. "Oral delivery of Biologically active parathyroid hormone,"Pharm Res. Jul. 2001; 18(7):964-70.
Mayo clinic (https://www.mayoclinic.org/diseases-conditions/hypoparathyroidism/diagnosis-treatment/drc-20355381accessed Mar. 9, 2023).
Bone Health and Osteoporosis Foundation (https://www.bonehealthandosteoporosis.org/patients/treatment/medicationadherence/ teriparatide-parathyroid-hormone-pth-1 -34-forteo/> accessed Mar. 9, 2023).
Protein S deficiency (https://my.clevelandclinic.org/health/diseases/21877-protein-s-deficiency.
Deplanque et al. "Phase II trial of the antiangiogenic agent IM862 in metastatic renal cell carcinoma," British Journal of Cancer, (2004) 91, 1645-1650.
Skander et al. "Chemical optimization of artificial metalloenzymes based on the biotin-avidin technology: (S)-selective and solvent-tolerant hydrogenation catalysts via the introduction of chiral amino acid spacers,"Chem Commun, 2005, 4815-4817.
Lamacchia et al. "Changes in wheat kernel proteins induced by microwave treatment," Food Chem. Apr. 15, 2016;197 (Pt A): 634-40.
de Pomerai et al. "Microwave radiation can alter protein conformation without bulk heating," FEBS Letters 543 (2003) 93-97.
Holten-Andersen et al., "Design and Preclinical Development of TransCon PTH, an Investigational Sustained-Release PTH Replacement Therapy for Hypoparathyroidism," J. Bone Miner. Res. 34(11):2075-2086 (2019).
Shimizu et al., Pharmacodynamic actions of a long-acting PTH analog (LA-PTH) in thyroparathyroidectomized (TPTX) rats and normal monkeys, J. Bone Miner. Res. 31(7):1405-12 (2016).

(56) References Cited

OTHER PUBLICATIONS

Noda et al., "Optimization of PTH/PTHrP Hybrid Peptides to Derive a Long-Acting PTH Analog (LA-PTH)," JBMR Plus 4(7):e10367 (2020).
Tamura et al., "Identification of an orally active small-molecule PTHR1 agonist for the treatment of hypoparathyroidism," Nat. Commun. 7:13384 (2016).
Fujiwara et al. "Racemization-Free Synthesis of C-Terminal Cysteine-Peptide Using 2-Chlorotrityl Resin," Chem. Pharm. Bull. 42(3) 724-726 (1994).
Bellido et al., "Proteasomal Degradation of Runx2 Shortens Parathyroid Hormone-induced Anti-apoptotic Signaling in Osteoblasts," J. Biol. Chem. 278(50): 50259-50272 (2003).
Bilezikian et al., "Hypoparathyroidism in the Adult: Epidemiology, Diagnosis, Pathophysiology, Target-Organ Involvement, Treatment, and Challenges for Future Research," J. Bone Miner. Res. 26(10): 2317-2337 (2011).
Cipriani et al., "Vertebral Fracture Assessment in Postmenopausal Women With Postsurgical Hypoparathyroidism," J. Clin. Endocrinol. Metab. 106(5): 1303-1311 (2021).
Gozes, I. and Furman, S. "VIP and Drug Design," Curr Pharm Des 9: 483-494, (2003).
Kim et al., "Intermittent Parathyroid Hormone Administration Converts Quiescent Lining Cells to Active Osteoblasts," J. Bone Miner. Res. 27(10): 2075-2084 (2012).
Neer et al., "Effect of Parathyroid Hormone (1-34) On Fractures and Bone Mineral Density in Postmenopausal Women With Osteoporosis," N. Engl. J. Med., 344(19): 1434-1441 (2001).
Rubin et al., "Dynamic and Structural Properties of the Skeleton in Hypoparathyroidism," J. Bone Miner. Res. 23(12): 2018-2024 (2008).
Rubin, "Recent advances in understanding and managing hypoparathyroidism [version 1; peer review: 3 approved]," F1000Research. 9(Faculty Rev): 766 (2020).
Siggelkow et al., "Burden of illness in not adequately controlled chronic hypoparathyroidism: Findings from a 13-country patient and caregiver survey," Clin. Endocrinol. 92(2):159-168 (2020).
Tay et al., "Optimal dosing and delivery of parathyroid hormone and its analogues for osteoporosis and hypoparathyroidism—translating the pharmacology," Br. J. Clin. Pharmacol. 84: 252-267 (2018).
Underbjerg et al., "Cardiovascular and Renal Complications to Postsurgical Hypoparathyroidism: A Danish Nationwide Controlled Historic Follow-Up Study," J. Bone Miner. Res. 28(11): 2277-2285 (2013).
Winer et al., "A Randomized, Cross-Over Trial of Once-Daily Versus Twice-Daily Parathyroid Hormone 1-34 in Treatment of Hypoparathyroidism," J. Clin. Endocrinol. Metab. 83(10): 3480-3486 (1998).
Aggarwal et al., "Neuropsychological dysfunction in idiopathic hypoparathyroidism and its relationship with intracranial calcification and serum total calcium," Eur. J. Endocrin. 168: 895-903 (2013).
Aloia et al., "Reference Range for Serum Parathyroid Hormone," Endocr. Pract. 12(2): 137-144 (2006).
Hadker et al., "Understanding the Burden of Illness Associated with Hypoparathyroidism Reported Among Patients in the Paradox Study," Endocr. Pract. 20(7): 671-679 (2014).
Kousteni and Bilezikian, "Cellular Actions of Parathyroid Hormone," Principles of Bone Biology, 3rd Edition, Academic Press Inc., 639-656 (2008).
Mosekilde et al., "The Anabolic Effects of Human Parathyroid Hormone (hPTH) on Rat Vertebral Body Mass Are also Reflected in the Quality of Bone, Assessed by Biomechanical Testing: A Comparison Study between hPTH-(I-34) and hPTH-(I-84)*," Endocrinology 129: 421-428, (1991).
Papapoulos et al., "Clearance of Exogenous Parathyroid Hormone in Normal and Uraemic Man," Clinical Endocrinology 7: 211-225 (1977).
Rejnmark et al., "Therapy of Hypoparathyroidism by Replacement with Parathyroid Hormone," Scientifica (Cairo) 2014:765629 (2014).
Schwieter et al., "Single-dose subcutaneous administration of recombinant human parathyroid hormone [rhPTH ( I-84)] in healthy postmenopausal volunteers," Clin. Pharmacol. Ther. 61: 360-76 (1997).
Shoback et al., "Presentation of Hypoparathyroidism: Etiologies and Clinical Features," J Clin Endocrinol Metab. 101(6): 2300-12 (2016).
Shoback, "Hypoparathyroidism," N. Engl. J. Med. 359: 391-403 (2008).
Sikjaer et al., "PTH(1-84) Replacement Therapy in Hypoparathyroidism: A Randomized Controlled Trial on Pharmacokinetic and Dynamic Effects After 6 Months of Treatment," J. Bone Miner. Res. 28(10): 2232-43 (2013).
Barman, Panchall et al. "Strategic Approaches to Improvise Peptide Drugs as Next Generation Therapeutics," International Journal of Peptide Research and Therapeutics, 29:61, (2023).
Tay, Donovan et al. "Optimal dosing and delivery of parathyroid hormone and its analogues for osteoporosis and hypoparathyroidism translating the pharmacology," Br J Clin Pharmacol, 8 (2018), pp. 252-267.
Nestor Jr. "The Medicinal Chemistry of Peptides," Current Medicinal Chemistry, 16, 4399-4418, (2009).
Sikjaer, et al. "PTH Treatment in Hypoparathyroidism," Current Drug Safety, 6, 89-99, (2011).
Scifinder, Maleimide Side, Nov. 6, 2012.
Scifinder, Minimal Vitamin D side, Nov. 6, 2012.
Scifinder, Vitamin D side, Nov. 6, 2012.
Seifter, S. and Englard, S. (1990), "Analysis for Protein Modifications and Nonprotein Cofactors," Methods Enzymol 182: 626-646.
Sidhu et al., "Phage-displayed Antibody Libraries of Synthetic Heavy Chain Complementarity Determining Regions," J. Mol. Biol. 338(2): 299-310 (2004).
Slatopolsky et al., "A New Analog of Calcitriol, 19-Nor-1,25-(OH), D, , Suppresses Parathyroid Hormone Secretion in Uremic Rats in the Absence of Hypercalcemia," Am J. Kidney Dis. 26: 852 (1995).
So et al., "A Novel Gemini Vitamin D Analog Represses the Expression of a Stem Cell Marker CD44 in Breast Cancer," Mol Pharmacol. 79(3):360-7 (2011).
Stamatov SD and Gronowitz S, 1990, "Glyceroamidothiophosphates of Cholecalciferol (Vitamin D3)," Lipids 25: 149-151.
Steddon et al. "Vitamin D analogues: how do they differ and what is their clinical role," Nephrol. Dial. Transplant. 16(10): 1965-1967 (2001).
Sun C, et al., 2013, "Bifunctional PEGylated Exenatide-Amylinomimetic Hybrids to Treat Metabolic Disorders: An Example of Long-Acting Dual Hormonal Therapeutics," Journal of Medicinal Chemistry 56: 9328-9341.
Swamy N, et al., 1995, "Affinity Purification of Human Plasma Vitamin D-Binding Protein," Protein Expression and Purification 6: 185-188.
Swamy N, et al., 1997, "Roles of Structure and Orientation of Ligands and Ligand Mimics inside the Ligand-Binding Pocket of the Vitamin D-Binding Protein," Biochemistry 36: 7432-7436.
Swamy N, et al., 2000, "Probing the Vitamin D Sterol Binding Pocket of Human Vitamin D Binding Protein with Bromoacetate Affinity Labeling Reagents Containing the Affinity Probe at C-3, C-6, C-11, and C-19 Positions of Parent Vitamin D Sterols," Archives of Biochemistry and Biophysics 373(2): 471-478.
Teegarden et al.,"Determination of the Affinity of Vitamin D Metabolites to Serum Vitamin D Binding Protein Using AssayEmploying Lipid-Coated Polystyrene Beads," Anal. Biochemistry 199(2):293-299 (1991).
Touraine P, et al., 2009, "Lipoatrophy in GH Deficient Patients Treated with a Long-Acting PEGylated GH," European Journal of Endocrinology 161(4): 533-40.
Trussel S, et al., 2009, "New Strategy for the Extension of the Serum Half-Life of Antibody Fragments," Bioconjugate Chemistry 20: 2286-2292.
Vaswani and Hamilton, Ann. Allergy, Asthma & Immunol. 1:105-115 (1998).
Verboven C, et al., 2002, "A Structural Basis for the Unique Binding Features of the Human Vitamin D-Binding Protein," Nature Structural Biology 9: 131-6.

(56) References Cited

OTHER PUBLICATIONS

Vestergaard ET, et al., "Constant intravenous infusion in healthy men: clinical pharmacokinetics and metabolic effects," Am J Physiol Endocrinol Metab 292:E1829-E1836.
Mahov IR, et al., 2006, "Design and Regioselective Synthesis of a New Generation of Targeted Chemotherapeutics. Part 1: EC145, a Folic Acid Conjugate of Desacetylvinblastine Monohydrazide," Bioorganic & Medicinal Chemistry Letters 16: 5093-5096.
Wang X-F, et al., 2007, "A Peptide Conjugate of Vitamin E Succinate Targets Breast Cancer Cells with High ErbB2 Expression," Cancer Research 67: 3337-3344.
Wootton AM, 2005, "Improving the Measurement of 25-Hydroxyvitamin D," Clinical Biochemist Reviews 26: 33-6.
Wu B and Sun Y-N, 2014, "Pharmacokinetics of Peptide-Fc Fusion Proteins," Journal of Pharmaceutical Sciences 103: 53-64.
Xu J et al., 2009. "Acute glucose-lowering and insulin-sensitizing action of FGF21 in insulin-resistant mouse models—association with liver and adipose tissue effects," Am J Physiol Endocrinol Metab 297: E1105-E1114.
Xu P., et al., 2014, Long-acting hypoglycemic effects of PEGylated FGF21 and insulin glargine in mice with type 1 diabetes, Journal of Diabetes and Its Complications, in press, http://dx.doi.org/10.1016/j.jdiacomp.2014.10.001.
Zeidler J, et al., 2012, "Biologic TNF inhibiting agents for treatment of inflammatory rheumatic diseases: dosing patterns and related costs in Switzerland from a payers perspective" Health Economics Review 2:20.
Zhang J, et al., 2010, "Identification of Two Distinct Cell Binding Sequences in the Vitamin D Binding Protein," Biochimica et Biophysica Acta 1803: 623-629.
Zhang Q, et al., 2010, "Synthesis of C-11 Linked Active Ester Derivatives of Vitamin D3 and Their Conjugations to 42-Residue Helix-Loop-Helix Peptides," Tetrahedron 66: 4577-4586.
Zhang, L. and Bulaj, G. (2012). "Converting Peptides into Drug Leads by Lipidation," Curr Med Chem 19: 1602-1618.
Zhao J, et al., 2013, "Targeted Co-delivery of Docetaxel and siPlk1 by Herceptin-conjugated Vitamin E TPGS Based Immunomicelles," Biomaterials 34: 3411-3421.
Zhou K, et al., 2009, "Studies of Poly(ethylene glycol) Modification of HM-3 Polypeptides," Bioconjugate Chemistry 20: 932-936.
Gozes, "Potential clinical applications of vasoactive intestinal peptide: a selected update," Best Practice & Research Clinical Endocrinology & Metabolism vol. 18, No. 4, pp. 623-640, 2004.
American Peptide Company, "The case for PEG conjugation", 2008.
Drug Lib.com, "Vitamin D2", copyright, 2006-2015.
Kojima et al. "Ghrelin: From Gene to Physiological Function", 2010, p. 185-205.
Akamizu, et al. Pharmacokinetics, safety, and endocrine and appetite effects of ghrelin administration in young healthy subjects. European Journal of Endocrinology, 150:447-455 (2004).
Bertrand, et al. Apelin and Energy Metabolism. Frontiers in Physiology 6:115 (2015).
Castan-Laurell, et al. Apelin, Diabetes, and Obesity. Endocrine 40(1):1-9 (2011).
Fishwild et al. High-Avidity Human IgGk Monoclonal Antibodies from a Novel Strain of Minilocus Transgenic Mice. Nature Biotechnology 14:845-851 (1996).
Frolik, et al. Anabolic and Catabolic Bone Effects of Human Parathyroid Hormone (1-34) are Predicted by Duration of Hormone Exposure. Bone 33: 372-379 (2003).
Presta, et al. Humanization of an Anti-Vascular Endothelial Growth Factor Monoclonal Antibody for the Therapy of Solid Tumors and Other Disorders. Cancer Research 57:4593-4599 (1997).
Satterwhite, et al. Pharmacokinetics of Teriparatide (rhPTH[1-34]) and Calcium Pharmacodynamics in Postmenopausal Women with Osteoporosis. Calcif Tissue Int. 87:485-492 (2010).
Winer K.K., et al. Synthetic Human Parathyroid Hormone 1-34 Replacement Therapy: A Randomized Crossover Trial Comparing Pump Versus Injections in the Treatment of Chronic Hypoparathyroidism. J. Clin. Endocrinal. Metab. 97(2): 391-399 (2012).
PCT Search Report and Written Opinion dated Jun. 5, 2013, from PCT App. No. PCT/US13/31788, filed on Mar. 14, 2013.
Zhao et al. Potential use of cholecalciferol polyethylene glycol succinate as a novel pharmaceutical additive. Journal of Biomedical Materials Research Part A, 84A(4): 954-964, 2007.
Hall et al. "D-VITylation: Harnessing the biology of vitamin D to improve the pharmacokinetic properties of peptides and small proteins," International Journal of Pharmaceutics 624 (2022) and published supplemental (2022).
Kerr et al. "EXT418, a novel long-acting ghrelin, mitigates Lewis lung carcinoma induced cachexia in mice," Journal of Cachexia, Sarcopenia and Muscle (2023).
Dean et al. "Role of Amino Acid Side Chains in Region 17-31 of Parathyroid Hormone (PTH) in Binding to the PTH Receptor," J.Biol. Chem. 281:32485-32495 (2006).
Karpf et al. "A Randomized Double-Blind Placebo-Controlled First-In-Human Phase 1 Trial of TransCon PTH in Healthy Adults," Journal of Bone and Mineral Research, vol. 35, No. 8, Aug. 2020, pp. 1430-1440 (2020).
Khan et al. "PaTH Forward: A Randomized, Double-Blind, Placebo-Controlled Phase 2 Trial of TransCon PTH in Adult Hypoparathyroidism," The Journal of Clinical Endocrinology & Metabolism, 2022, vol. 107, No. 1, e372-e385 (2022).
Khan et al. "Efficacy and Safety of Parathyroid Hormone Replacement With TransCon PTH in Hypoparathyroidism: 26-Week Results From the Phase 3 PaTHway Trial," Journal of Bone and Mineral Research, vol. 38, No. 1, Jan. 2023, pp. 14-25 (2023).
PCT Invitation to Pay Additional Fees dated Jan. 26, 2024 issued in PCT/US2023/032727.

\* cited by examiner

EXT608

LONG-ACTING PARATHYROID HORMONE

CROSS REFERENCE TO RELATED APPLICATIONS

This invention was made with Government support under Grant Nos. R43DK107231 and R44DK107231 awarded by the National Institute of Health. The Government has certain rights in this invention.

SEQUENCE LISTING

The instant application contains a Sequence Listing which has been submitted electronically in XML format and is hereby incorporated by reference in its entirety. Said XML copy, created on Oct. 3, 2023, is named XTND012US1_SL.xml and is 13,900 bytes in size.

FIELD OF THE INVENTION

The invention provides a long-acting parathyroid hormone peptide (PTH) that is retained in a subject's blood serum for periods of time that greatly exceed the natural hormone. The long-acting PTH is conjugated to the carbon 3 position of a non-hormonal vitamin D via a scaffold of discreet length that facilitates its purification, detection, solubility, and efficacy at the PTH receptor (PTHR). In some embodiments, the PTH may be conjugated to the non-hormonal vitamin D via a 36-mer poly(ethylene glycol) moiety (PTH-PEG36-VitD). In other embodiments, the non-hormonal vitamin D lacks a hydroxyl group at the Carbon 1 position. In other embodiments, optimized manufacturing methods and formulations are provided. The PTH-PEG36-VitD has a vastly-improved serum half-life and bioavailability when compared to a non-conjugated PTH peptide. In animal models, PTH-PEG36-VitD also significantly increases serum calcium, reduces urinary calcium, and reduces serum phosphate.

BACKGROUND OF THE INVENTION

The invention provides improved PTH-vitamin D conjugates for use in pharmacological compositions to treat conditions such as hypoparathyroidism and related conditions. Vitamin D plays a role in calcium, phosphate, and bone homeostasis. Vitamin D is a group of fat-soluble secosteroids. Several forms (vitamers) of vitamin D exist. The two major forms are vitamin $D_2$ or ergocalciferol, and vitamin $D_3$ or cholecalciferol. Vitamin D without a subscript refers to vitamin $D_2$, $D_3$ or other forms known in the art. In humans, vitamin D can be ingested as cholecalciferol (vitamin $D_3$) or ergocalciferol (vitamin $D_2$). The major source of vitamin D for most humans is sunlight. Once vitamin D is made in the skin or ingested, it needs to be activated by a series of hydroxylation steps, first to 25-hydroxyvitamin D ($25(OH)D_3$) in the liver and then to 1,25-dihydroxyvitamin $D_3$ ($1\alpha,25(OH)2D_3$) in the kidney. $1\alpha,25(OH)2D_3$ is the active "hormonal" form of vitamin D because it binds to the vitamin D receptor (VDR). $25(OH)D_3$ is a "non-hormonal" form of vitamin D and is the major circulating form in the human body. It binds the vitamin D Binding Protein (DBP or VDBP). It is only converted to the hormonal form as needed. An example of a non-hormonal vitamin D form is one that lacks a $1\alpha$-hydroxyl group.

Parathyroid hormone (PTH), parathormone or parathyrin, is secreted by the chief cells of the parathyroid glands. It is a polypeptide containing 84 amino acids (SEQ ID NO:2). It is typically present in serum at a concentration of 10-65 pg/mL The N-terminal 34 amino acids, however, retain full biological activity on the G protein-coupled receptor parathyroid hormone receptor 1 (PTH1R) that is primarily expressed in the kidneys and bone (Mosekilde et al., *Endocrinology* 129: 421-428, (1991)). (Tay et al., *Principles of Bone Biology* (Academic Press, 4th Edition, Bilzekian et al editors), Chapter 69, 1633-1642, 2020); (Mosekilde et al., *Endocrinology* 129: 421-428 (1991)). The foregoing are incorporated by reference in their entirety.

PTH plays a role in mineral homeostasis through at least three mechanisms: (1) PTH stimulates renal conversion of 25-hydroxyvitamin D to 1,25-dihydroxyvitamin D, which in turn increases intestinal calcium and phosphate absorption, (2). PTH enhances calcium reabsorption at the distal convoluted tubule and collecting ducts of the kidney, and (3) PTH increases serum calcium through bone resorption mediated by osteocytes/osteoblasts. This releases calcium as well as magnesium and phosphate into circulation (Shoback, N. *Engl. J. Med.* 359: 391-403 (2008)). PTH also regulates serum phosphate levels through bone resorption, vitamin D mediated intestinal absorption, and renal phosphate excretion (Bilezikian et al., *J. Bone Miner. Res.* 26(10): 2317-2337 (2011); Sikjaer, Rejnmark and Mosekilde, *Curr. Drug Saf* 6(2):89-99 (2011)). The foregoing are incorporated by reference in their entirety.

While bone resorption and intestinal absorption of phosphate result in increased serum phosphate, increased renal excretion removes phosphate from serum at a higher rate resulting in an overall net decrease in serum phosphate due to PTH (Shoback, N. *Engl. J. Med.* 359: 391-403 (2008)). PTH, however, has a very short serum half-life in humans of approximately 5 minutes with intravenous injection (Papapoulos et al., *Clinical Endocrinology* 7: 211-225 (1977)). The apparent half-life after subcutaneous injection is longer (1.5-2.5 h) due to slow absorption into circulation (Schweiter et al., *Clin. Pharmacol. Ther.* 61: 360-76 (1997); Rejnmark et al., *Scientifica* (Cairo) 2014:765629 (2014); Sikjaer et al., *J. Bone Miner. Res.* 28(10): 2232-2243 (2013)). This, however, is too short for use as an effective therapeutic hormone replacement. The foregoing are incorporated by reference in their entirety.

Hypoparathyroidism is a low level of PTH in the blood that is most commonly due to damage to or removal of parathyroid glands during thyroid surgery, immune system-related damage, inheritance, or other rare causes. It can lead to low levels of calcium in the blood, often causing cramping and twitching of muscles or tetany (involuntary muscle contraction), and several other symptoms. Calcium replacement or vitamin D can ameliorate the symptoms but can increase the risk of kidney stones and chronic kidney disease. See, e.g. Winer K K, et. al. *J. Clin. Endocrinol. Metab.* 97(2): 391-399 (2012), incorporated by reference in its entirety.

Hypoparathyroidism can occur when an individual is born without the parathyroid gland (typically due to a chromosomal deletion), the gland has been damaged or removed during a surgical procedure (e.g. thyroidectomy due to thyroid cancer or goiter), or when the organ is damaged due to an autoimmune response, iron accumulation, magnesium deficiency, or other idiopathic or genetic causes (Bilezikian et al., *J. Bone Miner. Res.* 26 (10): 2317-37 (2011); Rubin *F1000Research.* 9(Faculty Rev): 766 (2020)). A lack of PTH leads to low serum calcium (hypocalcemia), high serum phosphate (hyperphosphatemia), high urinary calcium (hypercalciuria) due to decreased renal reabsorption, and increased bone density, characterized by increased cortical and trabecular bone density (Shoback et al, *J Clin Endocrinol Metab.* 101(6): 2300-12 (2016)). If left untreated, hypoparathyroidism affects virtually every organ system in the body. These physiological changes (hypocalcemia, hypercalciuria, hyperphosphatemia and the near absence of PTH) alone or in combination with each other, will cause neuromuscular symptoms (persistent muscle cramps, paresthesia, tetany, seizures, cardiac arrhythmias), ischemic heart disease, kidney stones and nephrocalcinosis, and increased risk of vertebral fractures despite the increased bone mineral density measurements (Underbjerg et al., *J. Bone Miner. Res.* 28(11): 2277-2285 (2013); Cipriani et al., *J. Clin. Endocrinol. Metab.* 106(5): 1303-1311 (2021)). Additionally, hypoparathyroidism patients suffer from emotional and cognitive disorders such as anxiety, depression, memory problems, and general "brain fog" which have been attributed to lack of PTH (Aggarwal et al., *Eur. J. Endocrinol.* 168: 895-903 (2013)). Importantly, patients with improperly controlled hypoparathyroidism report a significantly reduced quality of life, with 75% of patients reporting that their disease affects their ability to work, and 63% of patients reporting negative effects on their family relationships (Siggelkow et al., *Clin. Endocrinol.* 92(2):159-168 (2020)). The foregoing are incorporated by reference in their entirety.

PTH can have a net anabolic or catabolic action on bone based on the duration of PTH exposure, which is regulated by differential stimulation of osteoblasts and osteoclasts (Frolick et al., *Bone* 33: 372-379 (2003)). Intermittent PTH exposure has an anabolic effect and is the basis of Forteo® (PTH1-34), the treatment for increasing bone mineral density (BMD) in osteoporosis patients (Neer et al., *N. Engl. J. Med.,* 344(19): 1434-1441 (2001)). PTH acutely increases bone deposition (primarily trabecular bone) without resorption leading to increased bone mineral density via preferential stimulation of osteoblasts and osteoblast precursor cells which express PTH1R, but without activating osteoclasts, which do not express the receptor (Silva et al., *J. Endocrinol. Invest.* 34(10): 801-810 (2011); Kousteni and Bilezikian, *Principles of Bone Biology,* 3rd Edition, *Academic Press Inc.,* 639-656 (2008)). This direct stimulation of osteoblasts and precursor cells reduces osteoblast apoptosis and increases osteoblastogenesis leading to increased osteoblast numbers and activity (Kim et al., *J. Bone Miner. Res.* 27(10): 2075-2084 (2012); Bellido et al., *J. Biol. Chem.* 278(50): 50259-50272 (2003)). The foregoing are incorporated by reference in their entirety.

Hypoparathyroidism patients have low physiological PTH exposure and present with low bone turnover due to reduced acute and direct osteoblast activity through PTH1R stimulation and reduced osteoclast activation via osteoblast and osteocyte mediated expression of RANKL (Rubin et al., *J. Bone Miner. Res.* 23(12): 2018-2024 (2008)). This reduction bone remodeling results in higher BMD in hypoparathyroidism patients (Bilezikian et al., *J. Bone Miner. Res.* 26(10): 2317-2337 (2011)). Continuous PTH exposure (via an insulin-style pump, a multiple daily dosing regimen or a long-acting PTH) that more closely resembles physiological exposure would result in normalization of bone turnover and lowering of BMD in hypoparathyroidism patients (Winer et al., *J. Pediatr.* 203:391-9 (2018)). The foregoing are incorporated by reference in their entirety.

PTH replacement therapy leads to normocalcemia in patients (Winer et al., *J. Clin. Endocrinol. Metab.* 83(10): 3480-3486 (1998)). However, exogenously administered PTH is rapidly cleared from the body, therefore it is difficult to provide hypoparathyroidism patients with physiological PTH concentrations, which need to remain within a narrow concentration window to avoid either hypocalcemia or hypercalcemia (Tay et al., *Br. J. Clin. Pharmacol.* 84: 252-267 (2018)). In fact, only subcutaneous pump delivery, compared to once- or twice-daily injections, provided the closest approach to the physiological replacement of PTH (Winer et al., *J. Clin. Endocrinol. Metab.* 97(2): 391-399 (2012)). This is because the plasma half-life of PTH in humans is less than 15 minutes when given intravenously, or an estimated 2-3 hours when given subcutaneously due to slower absorption kinetics (Papapoulos et al., *Clin. Endocrinol.* 7: 211-225 (1977); Sikjaer et al., *J. Bone Miner. Res.* 28(10): 2232-43 (2013)). The foregoing are incorporated by reference in their entirety.

The current standard of care for hypoparathyroidism consists of calcium and active vitamin D supplementation. Patients are left to manage their symptoms themselves throughout the day with some patients taking up to 10 pills a day. On average, symptoms last 13 h+/−9 h per day, with more severe disease impacting patient's life even more (Hadker et al., *Endocr. Pract.* 20(7): 671-679 (2014), incorporated by reference in its entirety). Although supplementation aims to control the symptoms of hypocalcemia, it worsens the nephrological situation, fails to improve the bone structure, and does not help the emotional and cognitive disorders. The ideal therapy for hypoparathyroidism would mimic endogenous levels of PTH, which remain flat throughout the day, in order to reverse hypocalcemia, hypercalciuria, and hyperphosphatemia.

Non-hormonal vitamin D forms have a greatly reduced affinity for VDR and a greatly increased affinity for DBP. DBP is the principal transporter of vitamin D metabolites. Its concentration in the plasma is 6-7 μM and has been detected in all fluid compartments. DBP concentrations exceed the physiological vitamin D metabolite concentrations. DBP is important for the translocation of vitamin D from the skin into circulation, and across cell membranes into the cytoplasm where vitamin D is activated into the hormonal form. The affinity of non-hormonal Vitamin D for DBP is significantly higher than the affinity of the hormonal form. In contrast, the affinity of the hormonal form to VDR is significantly higher than the non-hormonal form.

Vitamin D and vitamin D analogs have been approved for the treatment of osteoporosis and secondary hyperparathyroidism. Vitamin D has also been shown to inhibit proliferation and induce differentiation in normal as well as cancer cells. The level of vitamin D required for this activity causes severe toxicity in the form of hypercalcemia. Analogs of vitamin D have been approved for the treatment of psoriasis and others are currently being tested for cancer treatment. Many of the analogs discovered to have a reduced calcemic effect contain side-chain modifications. These modifications do not greatly affect VDR binding, and thus, in cell-based proliferation assays, show equal or even increased efficacy. It has been shown, however, that many of these modifications reduce binding to DBP and thereby reduce the half-life in the bloodstream.

The vitamin D forms that bind with higher affinity to DBP or VDR are known. (See Haddad, J. G., *J. Steroid Biochem. Molec. Biol.* Vol. 53, No. 1-6:579-582 (1995); Norman et al., *J. Steroid Biochem. & Mol. Biol.* 76:49-59, 51 (2001).) Norman teaches the difference between hormonal and non-hormonal forms of vitamin D. Norman first explains the basis for this teaching: "Vitamin D and all its metabolites . . . are, in comparison to other steroid hormones, unusually conformationally flexible . . . ." This results in "a wide array of molecular shapes that are available for binding to receptors involved with the 1α,25(OH)$_2$D$_3$-mediated biological responses . . . as well as for binding to DBP . . . ." (Norman at 50.) This conformational flexibility is demonstrated in Norman at FIG. 2. The vitamin D conformations that select for DBP (non-hormonal) or VDR (hormonal) are laid out in Norman at Table 1. The binding affinities of a large number of vitamin D metabolites for DBP or VDR are provided in Norman at Table 2 and FIG. 6. Norman further states at p. 51: "The preferred ligand for DBP is 25(OH)D$_3$, while the preferred ligand of the VDR$_{nuc}$ is 1α,25(OH)$_2$D$_3$. Thus, 25(OH)D$_3$ binds 668-fold more tightly to DBP than 1α,25(OH)$_2$D$_3$. In contrast, 1α,25(OH)$_2$D$_3$ binds 668-fold more tightly to the VDR$_{nuc}$ than 25(OH)D$_3$." The foregoing are incorporated by reference in their entirety.

The addition of poly(ethylene glycol) or (PEG) is a known method of increasing the half-life of some compounds by reducing kidney clearance, reducing aggregation, and diminishing potentially unwanted immune recognition (Jain, *Crit. Rev. Ther. Drug Carrier Syst.* 25:403-447 (2008)). The PEG is typically used at a considerably large size (20-40 kDa) to maximize the half-life in circulation. This can be accomplished by using either a single large PEG or multiple smaller PEGs attached to the compound. (Clark et al. *J. Biol. Chem.* 271:21969-21977 (1996); Fishburn, J. Pharm. Sci. 97:4167-4183 (2008)). The foregoing are incorporated by reference in their entirety.

SUMMARY OF THE INVENTION

The invention provides a long-acting parathyroid hormone peptide (PTH) that is retained in a subject's blood serum for periods of time that greatly exceed the natural hormone. The long-acting PTH is conjugated to the carbon 3 position of a non-hormonal vitamin D via a scaffold of discreet length that facilitates its purification, detection, solubility, and efficacy at the PTH receptor (PTHR).

Thus, the invention provides a pharmaceutical composition, comprising parathyroid hormone peptides (PTH) each conjugated via scaffolds to non-hormonal vitamin D moieties (PTH Conjugates) and a pharmaceutical excipient, wherein the PTH conjugates are of about a uniform size as measured by mass spectrometry, wherein the PTH conjugates have a solubility of at least about 0.550 mM in phosphate buffered saline (PBS) when measured at an absorbance of 280 nm using an extinction coefficient of 18,600 M$^{-1}$ cm$^{-1}$. In some embodiments, the PTH conjugates comprise a scaffold that is a 36 subunit poly(ethylene glycol) scaffold (PTH-PEG36-VitD).

In some embodiments of the invention, the PTH-PEG36-VitD comprises the structure:
H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Cys(succinimido-propionylamino-PEG36-propionyl-aminopropyl-25-hydroxy-Vitamin D)-OH (SEQ ID NO: 6);
or
H-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Cys(succinimido-propionylamino-PEG36-propionyl-aminopropyl-25-hydroxy-Vitamin D)-NH2 (SEQ ID NO: 7).

In some embodiments of the invention, the PTH conjugates have about the same activity on the PTH receptor (PTHR) as an equivalent unconjugated PTH peptide.

In some embodiments of the invention, the PTH conjugates are isolated as a carbonate salt. In other embodiments, the PTH conjugates are isolated as an acetate salt. In some embodiments of the invention, the PTH conjugates have a solubility of at least about 9.67 mM in PBS when measured at an absorbance of 280 nm using an extinction coefficient of 18,600 M$^{-1}$ cm$^{-1}$. In other embodiments, the pharmaceutical composition is formulated at a pH of about 4.0 to about 5.5. In preferred embodiments, the pharmaceutical composition is formulated at a pH of about 5.5. In other embodiments, the pharmaceutical composition is formulated with mannitol. In other embodiments, the pharmaceutical composition is formulated with polysorbate 80 (PS80).

In some embodiments of the invention, the PTH-PEG36-VitD is formulated as an acetate salt, wherein the pharmaceutical composition is formulated at a pH of about 5.5, and wherein the pharmaceutical composition comprises mannitol and PS80. In preferred embodiments, the PTH-PEG36-Vit D is formulated at a concentration of 0.4 mg/ml in about 10 mM sodium acetate buffer, pH about 5.5, about 4.5% mannitol, and about 0.25% Polysorbate 80.

In some embodiments, the PTH-PEG36-VitD is formulated as an acetate salt at a concentration of about 1, 2, 3, 4, 5, 6, 7, 8, 9, 10, 11, 12, 13, 14, 15 mM or more. In other embodiments, the PTH-PEG36-VitD is formulated at a pH of about 3.5-3.9, 4.0-4.5, 4.6-5.0, 5.1-5.5, or 5.6-6.0. In other embodiments, the PTH-PEG36-VitD is formulated with mannitol at a concentration of between about 2.5% and 5%, and more preferably between about 3.0-4.5%. In other embodiments, the PTH-PEG36-VitD is formulated with PS80 at a concentration of about 0%, 0.1%, 0.2%, 0.25%, 0.5%, 1.0%, 1.5%, 2.0%, 2.5%, or 3.0%. In other embodiments, the PTH-PEG36-VitD is formulated with PS80 at a concentration of between about 0% and 0.25%.

In some embodiments of the invention, the PTH conjugates are formulated with methionine at a concentration of between about 0 and 40 mM. In other embodiments, the PTH conjugates are formulated with methionine at a concentration of about 0, 5, 10, 20, or 40 mM. In preferred embodiments, the PTH conjugates are formulated with methionine at a concentration of about 40 mM.

In some embodiments of the invention, the pharmaceutical composition is formulated for subcutaneous delivery, intramuscular delivery, intravenous delivery, controlled release delivery, transdermal delivery, parenteral delivery, or by implanted reservoir. In preferred embodiments, the pharmaceutical composition is formulated for subcutaneous delivery.

In some embodiments of the invention, the PTH conjugates have a serum half-life of 7 to 15 hours in rats. In other embodiments, the PTH conjugates have a subcutaneous bioavailability of at least about 10-13% in rats. In other embodiments, the PTH conjugates have a serum half-life of about 24 to 32 hours in cynomolgus monkeys. In other embodiments, the PTH conjugates have a subcutaneous bioavailability of about 45-54% in cynomolgus monkeys.

In some embodiments of the invention, a dose of about 6 µg/kg of the PTH conjugate, given every day, increases the serum calcium levels in TPTx rats by an average of at least about 17% over the 0 dose level when measured during the 24 hours after the injection. In other embodiments, a dose of about 60 µg/kg of the PTH conjugate, given every day, increases the serum calcium levels in TPTx rats by an average of at least about 37% over the 0 dose level when measured during the 24 hours after the injection. In other embodiments, a dose of about 2 µg/kg of the PTH conjugate, given every other day, increases the serum calcium levels in cynomolgus monkeys by at least about 0.9 mg/dl over the 0 dose level when measured at 12 hours after the day 5 injection. In other embodiments, a dose of about 100 µg/kg of the PTH conjugate, given every other day, increases the serum calcium levels in cynomolgus monkeys by at least about 6.1 mg/dl over the 0 dose level when measured at 12 hours after the day 5 injection. In other embodiments, a dose of about 10 µg/kg of the PTH conjugates reduce the ratio of urinary to serum calcium levels in cynomolgus monkeys to equal to or lower than about 1.8. In other embodiments a dose of about 100 µg/kg of the PTH conjugates reduce the ratio of urinary to serum calcium levels in cynomolgus monkeys to equal to or lower than about 1.2.

In some embodiments of the invention, the PTH conjugates cause at least about a 14% decrease in serum phosphate levels in TPTx rats after about 12 days when about 6 µg/kg of the PTH conjugates are administered subcutaneously daily. In other embodiments, the PTH conjugates cause at least about a 39% decrease in serum phosphate levels in TPTx rats after about 12 days when about 60 µg/kg of the PTH conjugates are administered subcutaneously daily. In other embodiments, the PTH conjugates cause at least about a 1.0 mg/dl decrease in serum phosphate levels in cynomolgus monkeys after about 21 days when about 7.0 pg/kg of the PTH conjugates are administered subcutaneously every other day. In other embodiments, the PTH conjugates cause at least about a 1.8 mg/dl decrease in serum phosphate levels in cynomolgus monkeys after about 11 days when about 20 µg/kg of the PTH conjugates are administered subcutaneously every other day.

In some embodiments of the invention, the PTH conjugates bind to the vitamin D binding protein (VDBP) with a dissociation constant of about 5.2 µM.

The invention provides a method of treating a subject suffering from a condition selected from the list comprising hypoparathyroidism, hypocalcemia, hyperphosphatemia, hypercalciuria, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, thrombocytopenia, polyglandular autoimmune syndrome type 1, DiGeorge syndrome, CHARGE syndrome, Kenny-Caffey type 1, Kenny-Caffey type 2, hereditary deafness and renal dysplasia (HDR), autosomal dominant hypocalcemia type 1 (ADH1), autosomal dominant hypocalcemia type 2 (ADH2), and ADH1 with Bartter's type 5, comprising the step of administering the pharmaceutical composition of the invention to the subject. In some embodiments, the administration step is accomplished via a subcutaneous delivery, intramuscular delivery, intravenous delivery, controlled release delivery, transdermal delivery, parenteral delivery, or by implanted reservoir. In preferred embodiments, the administration is via a subcutaneous route. In other embodiments, the pharmaceutical composition is administered at a dose of about 2, 7, 10, or 20 µg/kg of the subject's body weight.

In some embodiments of the invention, the dose is administered about daily. In other embodiments, the dose is administered about every other day.

The invention provides the pharmaceutical compositions of the invention for use in treating hypoparathyroidism, hypocalcemia, hyperphosphatemia, hypercalciuria, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, thrombocytopenia, polyglandular autoimmune syndrome type 1, DiGeorge syndrome, CHARGE syndrome, Kenny-Caffey type 1, Kenny-Caffey type 2, hereditary deafness and renal dysplasia (HDR), autosomal dominant hypocalcemia type 1 (ADH1), autosomal dominant hypocalcemia type 2 (ADH2), or ADH1 with Bartter's type 5. In other embodiments, the invention provides a medicament comprising the pharmaceutical compositions of the invention.

The invention provides method of treating a subject suffering from a condition selected from the group comprising hypoparathyroidism, hypocalcemia, hyperphosphatemia, hypercalciuria, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, thrombocytopenia, polyglandular autoimmune syndrome type 1, DiGeorge syndrome, CHARGE syndrome, Kenny-Caffey type 1, Kenny-Caffey type 2, hereditary deafness and renal dysplasia (HDR), autosomal dominant hypocalcemia type 1 (ADH1), autosomal dominant hypocalcemia type 2 (ADH2), and ADH1 with Bartter's type 5, comprising administering to the subject a pharmaceutical composition comprising a plurality of parathyroid hormone (PTH) peptides each conjugated via a scaffold to a non-hormonal vitamin D (PTH Conjugate) and a pharmaceutical excipient, wherein each PTH peptide within the plurality is conjugated to a scaffold of about a uniform size as measured by mass spectrometry, wherein the method comprises the step of administering repeated doses of the pharmaceutical composition subcutaneously, and wherein the repeated doses results in a maximal to minimal concentration ratio of the PTH conjugates in serum samples from the subject (Cmax/Cmin ratio) of equal to or less than about 8.0.

In some embodiments, the Cmax/Cmin ratio is equal to or less than about 5.37. In preferred embodiments, the Cmax/Cmin ratio is equal to or less than about 4.59. In more preferred embodiments, the Cmax/Cmin ratio is equal to or less than about 3.36. In more preferred embodiments, the Cmax/Cmin ratio is equal to or less than about 2.38. In more preferred embodiments, the Cmax/Cmin ratio is equal to or less than about 1.83. In most preferred embodiments, the Cmax/Cmin ratio is equal to or less than about 1.79.

In some embodiments of the invention, the PTH conjugates have a serum half-life of 7 to 15 hours. In other embodiments, the PTH conjugates have a subcutaneous bioavailability of at least about 10-13%. In other embodiments, the PTH conjugates have a serum half-life of about 24 to 32 hours. In other embodiments, the PTH conjugates have a subcutaneous bioavailability of about 45-54%.

In some embodiments, a dose of about 2.0 pg/kg of the PTH conjugate, given every other day, increases the serum calcium levels by at least about 0.9 mg/dl over the 0 dose level when measured at 12 hours after the day 5 injection. In other embodiments, a dose of about 100 µg/kg of the PTH conjugate, given every other day, increases the serum calcium levels by at least about 6.1 mg/dl over the 0 dose level when measured at 12 hours after the day 5 injection.

In some embodiments, a dose of about 10 μg/kg of the PTH conjugates reduce the ratio of urinary to serum calcium levels to equal to or lower than about 1.8. In other embodiments, a dose of about 100 μg/kg of the PTH conjugates reduce the ratio of urinary to serum calcium levels to equal to or lower than about 1.2.

In some embodiments of the invention, the PTH conjugates cause at least about a 14% decrease in serum phosphate levels after about 12 days when about 6 μg/kg of the PTH conjugate is administered subcutaneously daily. In other embodiments, the PTH conjugates cause at least about a 39% decrease in serum phosphate levels after about 12 days when about 60 μg/kg of the PTH conjugate is administered subcutaneously daily.

The invention provides a kit, comprising the pharmaceutical compositions of the invention and instructions for its use for treating a condition in a patient. In some embodiments, the condition is hypoparathyroidism.

In some embodiments of the invention, the PTH-PEG36-VitD comprises the structure (SEQ ID NO: 6):

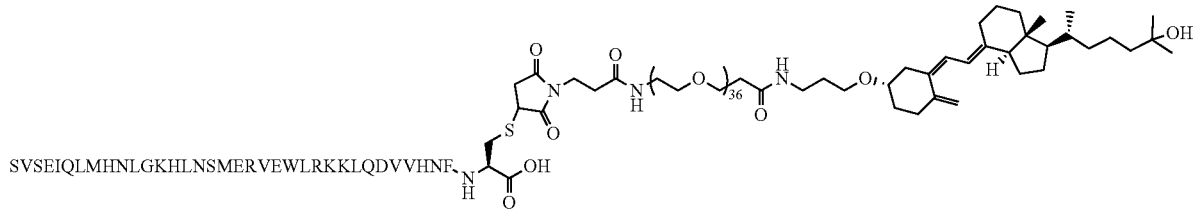

In other embodiments of the invention, the PTH-PEG36-VitD comprises the structure (SEQ ID NO: 7):

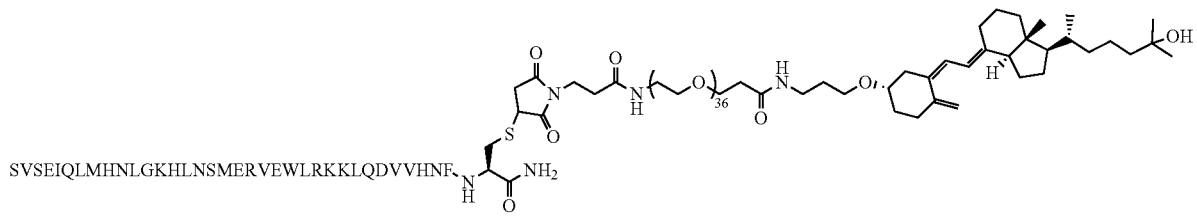

The invention provides a method of manufacturing the pharmaceutical compositions the invention, comprising conjugating the PTH peptides, the scaffolds, and the non-hormonal vitamin D moieties to form the PTH conjugates, wherein the conjugating step occurs at a pH of less than about 7.4. In some embodiments, the PTH peptide comprises the amino acid sequence of SEQ ID NO:3. In other embodiments, the conjugating step occurs at a pH of about 6.0. In other embodiments, the method further comprises a purification step for the conjugates at a pH of less than about 8.0. In preferred embodiments, the purification step is at a pH of about 5.5.

The invention provides a pharmaceutical carrier comprising a formula I:

$$B\text{-}(L)^a\text{-}S\text{-}(M)^b\text{-}C \qquad \text{I}$$

wherein:
B is a targeting group that is a vitamin D that is not hydroxylated at the carbon 1 position, conjugated at the carbon 3 position to (L)a;
S is a scaffold moiety, comprising poly(ethylene glycol) consisting of 36 repeating ethylene glycol units;
C is a maleimide group;
$(L)^a$ is a linker comprising $(CH_2)_3NHC(O)CH_2$; and
$(M)^b$ is a linker comprising $HNC(O)(CH_2)_2$.

In some embodiments of the invention, the pharmaceutical carrier described above comprises a compound having formula VI:

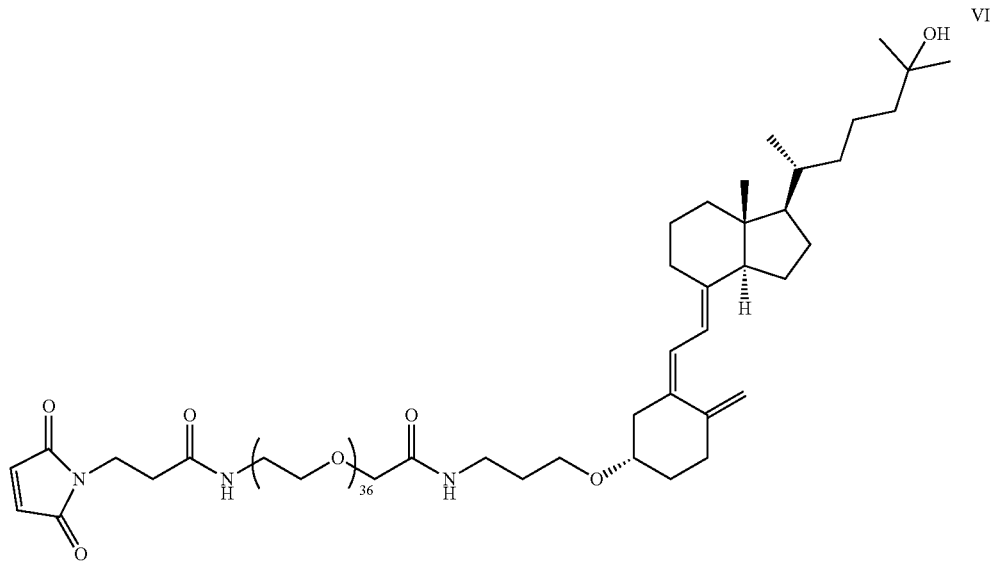

The invention provides a method of manufacturing a pharmaceutical composition comprising a parathyroid peptide (PTH) and the pharmaceutical carrier described above, comprising the steps of:
1) Purifying the compound having formula VI;
2) conjugating the compound having formula VI to the PTH;

In some embodiments, the purified compound having formula VI is not removed from a purification solvent prior to the conjugation step. In other embodiments, the purification step is accomplished by high pressure liquid chromatography (HPLC). In other embodiments, the conjugates are isolated as a carbonate salt. In other embodiments, the conjugates are isolated as an acetate salt.

In some embodiments of the invention described above, the PTH comprises the amino acid sequence of SEQ ID NO:3.

The invention provides a method of treating a human suffering from a condition selected from the group comprising hypoparathyroidism, hypocalcemia, hyperphosphatemia, hypercalciuria, osteoporosis, fracture repair, osteomalacia, osteomalacia and osteoporosis in patients with hypophosphatasia, steroid-induced osteoporosis, male osteoporosis, arthritis, osteoarthritis, osteogenesis imperfect, fibrous dysplasia, rheumatoid arthritis, Paget's disease, humoral hypercalcemia associated with malignancy, osteopenia, periodontal disease, bone fracture, alopecia, chemotherapy-induced alopecia, thrombocytopenia, polyglandular autoimmune syndrome type 1, DiGeorge syndrome, CHARGE syndrome, Kenny-Caffey type 1, Kenny-Caffey type 2, hereditary deafness and renal dysplasia (HDR), autosomal dominant hypocalcemia type 1 (ADH1), autosomal dominant hypocalcemia type 2 (ADH2), and ADH1 with Bartter's type 5, comprising the step of administering a pharmaceutical composition as described herein to the human. In some embodiments, the pharmaceutical composition is EXT608. In a preferred embodiment, the condition is hypoparathyroidism.

In some embodiments, the administration step is accomplished via a subcutaneous delivery, intramuscular delivery, intravenous delivery, controlled release delivery, transdermal delivery, parenteral delivery, or by implanted reservoir. In a preferred embodiment, the administration is via a subcutaneous route.

In some embodiments, the pharmaceutical composition is administered at a dose of about 2, 7, 10, or 20 µg/kg of the subject's body weight. In other embodiments, the dose is about 36, 108, or 324 µg. In other embodiments, the dose is administered about daily, about every other day, about every three days, about every four days, about every four days, about every five days, about every six days, about every seven days, about every eight days, or about every nine days.

In some embodiments, the dose results in a Cmax of between about 0.49 and 5.0 ng/ml. In a preferred embodiment, the dose results in a Cmax of about 5.0 ng/ml.

In some embodiments, the dose results in a Tmax of between about 3.3 and 5.3 hours. In a preferred embodiment, the dose results in a Tmax of about 2.7 hours.

In some embodiments, the dose results in an AUC of between about 5.9 and 118 (ng/ml)*h. In preferred embodiments, the dose results in an AUC of about 118 (ng/ml)*h.

In some embodiments, the dose results in a Tlast of between about 24 and 168 hours. In preferred embodiments, the dose results in a Tlast of about 168 hours. In a preferred embodiment, the dose results in a Cmax of about 5.0 ng/ml, a Tmax of about 2.7 hours, an AUC of about 118 (ng/ml)*h, and a Tlast of about 168 hours.

In some embodiments, the dose is about 324 µg SC and results in a $T_{1/2}$ of about 90 hours. In other embodiments, the dose is about 324 µg SC and results in an $AUC_{inf}$ of about 151 (ng/ml)*h. In other embodiments, the dose is about 324 µg SC and results in a clearance divided by bioavailability (CL/F) of about 2.2 L/h. In other embodiments, the dose is about 324 µg SC and results in an apparent volume of distribution during the terminal phase divided by bioavailability (Vz/F) of about 280 L. In other embodiments, the dose is about 324 µg SC and results in a mean retention time (MRT) of about 105 hours. In preferred embodiments, the dose is about 324 µg SC and results in a $T_{1/2}$ of about 90 hours, an $AUC_{inf}$ of about 151 (ng/ml)*h, a CL/F of about 2.2 L/h, aVz/F of about 280 L, and an MRT of about 105 hours.

In some embodiments of the invention, the pharmaceutical composition raises serum calcium levels for about 24 hours after administration. In other embodiments, the pharmaceutical composition reduces the level of endogenous PTH(1-84). In other embodiments, the pharmaceutical composition does not cause a significant increase in urinary calcium when measured at about 36 hours post-administration (data not shown).

The invention provides pharmaceutical compositions as disclosed herein, wherein the PTH conjugates are formulated with methionine at a concentration of between about 0 and 40 mM. In some embodiments, the PTH conjugates are formulated with methionine at a concentration of about 0, 5, 10, 20, or 40 mM. In preferred embodiments, the PTH conjugates are formulated with methionine at a concentration of about 40 mM.

The invention provides pharmaceutical compositions as disclosed herein, wherein after 308 hours of shaking the pharmaceutical composition, the PTH conjugates show a precipitation out of solution of about 0.411 or less optical density (OD) when measured at a wavelength of 600 nm. In some embodiments, after 308 hours of shaking the pharmaceutical composition, the PTH conjugates show a precipitation out of solution of about 0.242 or less optical density (OD) when measured at a wavelength of 600 nm. In preferred embodiments, after 308 hours of shaking the pharmaceutical composition, the PTH conjugates show a precipitation out of solution of about 0.015 or less optical density (OD) when measured at a wavelength of 600 nm.

The invention provides pharmaceutical compositions as disclosed herein, wherein the PTH conjugate purity decreases by about 7.7% or less after 69 hours of incubation at 4° C. In some embodiments, the PTH conjugate purity decreases by about 14.9% or less after 13 days of incubation at room temperature.

Error bars indicate the standard deviation (n=5). p-values vs the 0 µg/kg group (Vehicle) were calculated using the Student t-test (*<0.05, #<0.01).

Figure 21:
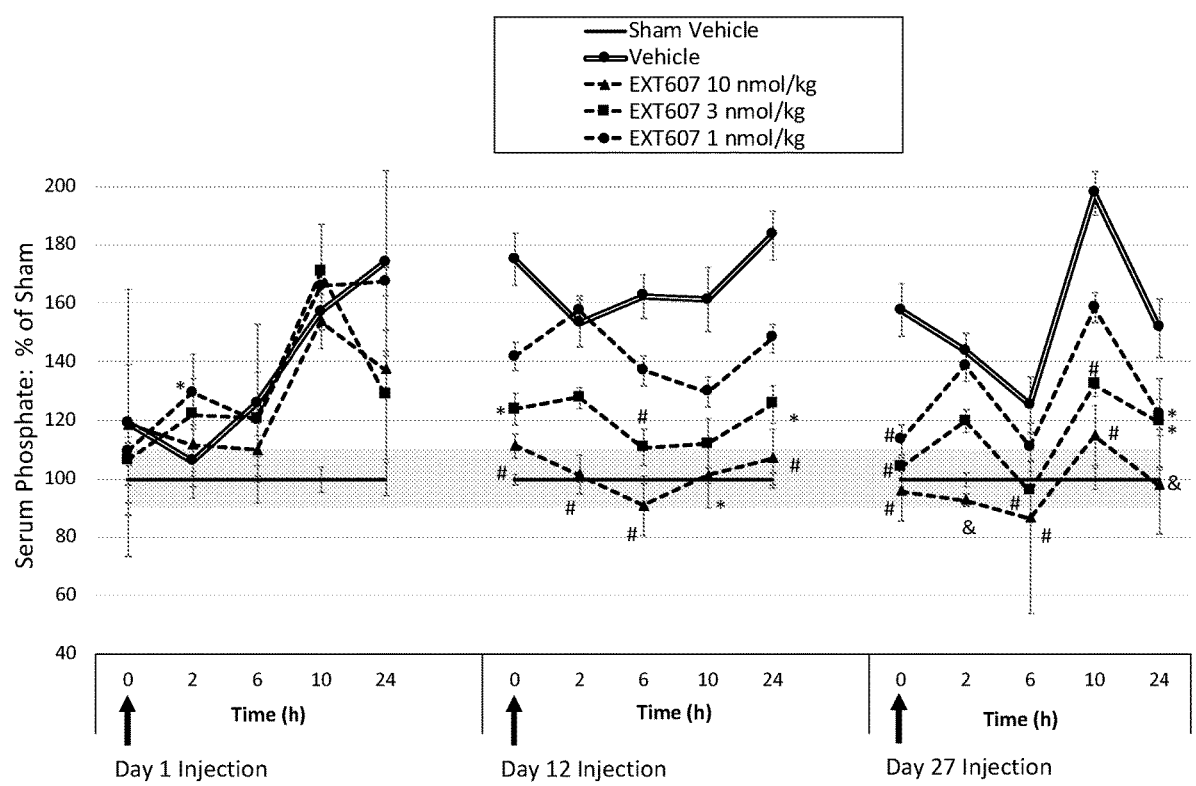

FIG. 21: Serum phosphate levels in TPTx rats on Days 1, 12 and 27 after daily subcutaneous dosing of EXT607 at 0 (Vehicle), 1, 3, or 10 nmol/kg. Serum phosphate values were normalized against the group which underwent a sham surgery and received vehicle (Sham Vehicle). Error bars indicate the standard deviation (n=5). p-values vs the 0 µg/kg group (Vehicle) were calculated using the Student t-test (*<0.05, #<0.01, &<0.001).

Figure 22:
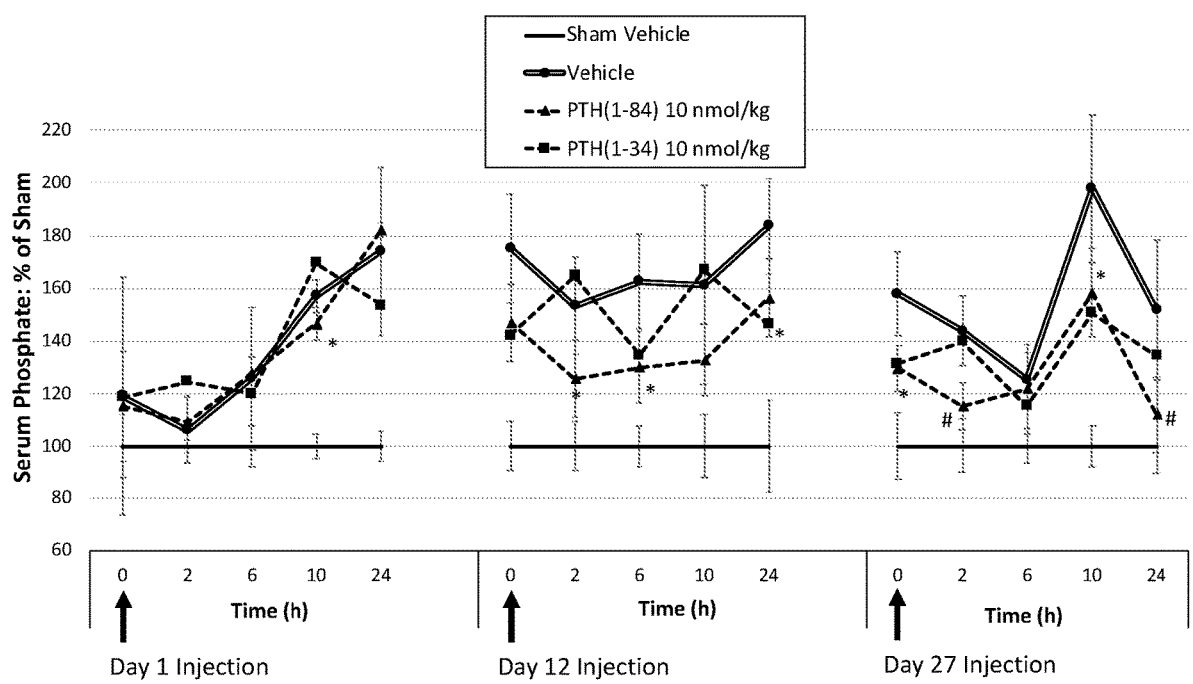

FIG. 22: Serum phosphate levels in TPTx rats on Days 1, 12 and 27 after daily subcutaneous dosing of PTH(1-34) and PTH(1-84) at 10 nmol/kg as compared to the Vehicle and Sham Vehicle control groups from FIG. 21. Serum phosphate values were normalized against the Sham Vehicle group. Error bars indicate the standard deviation (n=5). p-values vs the 0 µg/kg group (Vehicle) were calculated using the Student t-test (*<0.05, #<0.01).

Figure 23A:
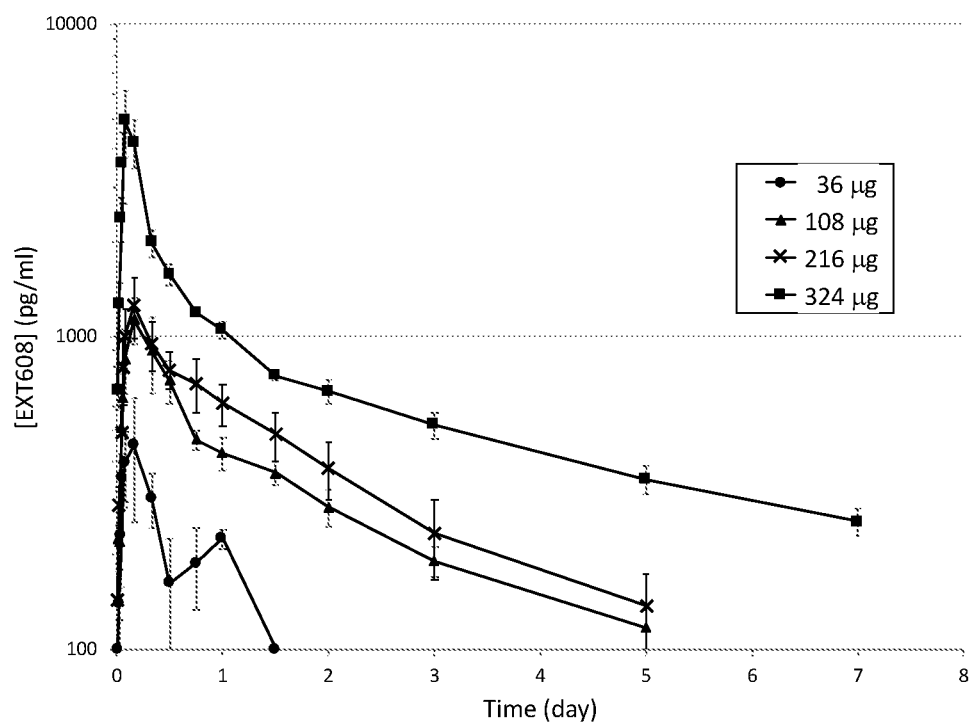

FIG. 23A: Pharmacokinetics of a single subcutaneous dose of EXT608 show vastly-improved serum half-life in humans. Error bars indicate the standard error of the mean (n=3).

Figure 23B:
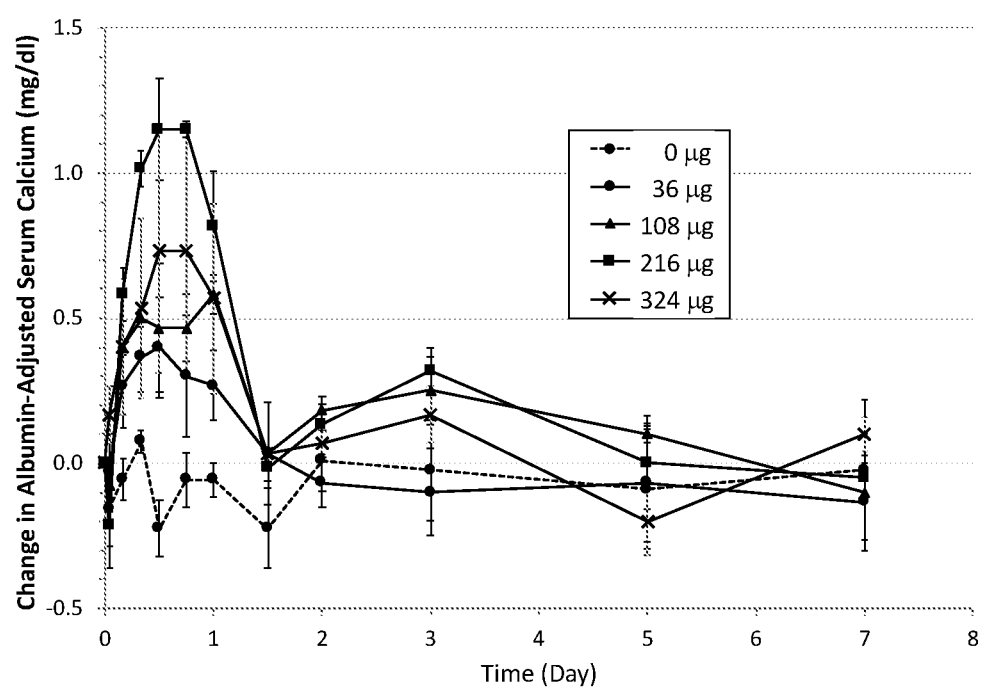

FIG. 23B: Changes in albumin-adjusted serum calcium levels in healthy human participants after a single subcutaneous dose of EXT608 at 0, 36, 108, 216, or 324 µg. Baseline values of serum calcium were calculated for each individual by averaging the −24 h and −1 h measurements. Error bars indicate the standard error of the mean (n=3).

Figure 23C:
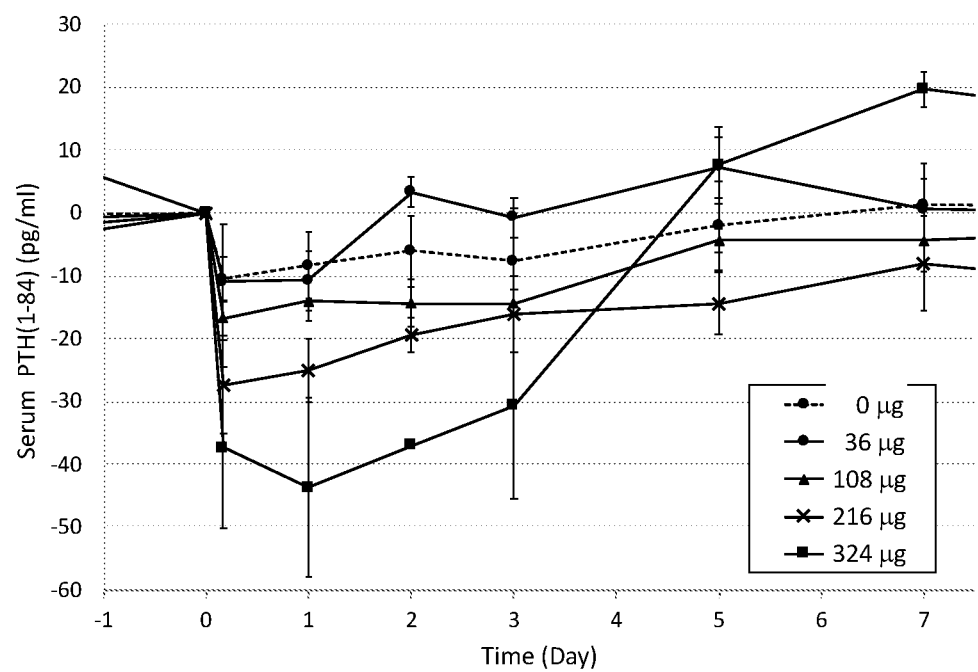

FIG. 23C: Changes in serum endogenous PTH(1-84) levels in healthy human participants after a single subcutaneous dose of EXT608 at 0, 36, 108, 216, or 324 µg. For each individual, the −1 h measurement was used as the baseline value. Error bars indicate the standard error of the mean (n=3).

DETAILED DESCRIPTION OF THE INVENTION

The invention provides a long-acting parathyroid hormone peptides (PTH) that are retained in a subject's blood serum for periods of time that greatly exceed the natural hormone. They are intended to replace endogenous PTH that is missing in patients with hypoparathyroidism and related conditions. The long-acting PTH is conjugated to the carbon 3 position of a non-hormonal vitamin D via a scaffold of discreet length that facilitates its purification, detection, solubility, and efficacy at the PTH receptor (PTHR). The PTH is conjugated to the non-hormonal vitamin D via a 36-mer poly(ethylene glycol) moiety (PTH-PEG36-VitD). The invention also provides optimized manufacturing methods and formulations. The PTH-PEG36-VitD has a vastly-improved serum half-life and bioavailability when compared to a non-conjugated PTH peptide. PTH-PEG36-VitD also significantly increases serum calcium, reduces urinary calcium, and reduces serum phosphate.

The invention provides carrier-drug conjugates comprising targeting groups that are non-hormonal vitamin D, vitamin D analogs, or vitamin D metabolites. Examples include vitamin D-based molecules that are not hydroxylated at the carbon 1 (C1) position. The carriers are linked to therapeutic compounds at the carbon 3 (C3) position. While not wishing to be bound by theory, it is believed that the hormonal forms of vitamin D are not appropriate for the carriers described herein because they can be toxic due to the induction of hypercalcemia. Also, because the hormonal forms bind the vitamin D receptor in cells, they may improperly target the carrier-drug conjugates to undesired cells or tissues. In contrast, non-hormonal vitamin D forms bind the Vitamin D Binding Protein (DBP or VDBP) and remain in circulation longer.

In some embodiments, the invention provides EXT607 and EXT608 (described below). They are useful for long-acting PTH replacement therapies and for the manufacture of pharmaceutical compositions. PTH is a naturally occurring hormone produced by the parathyroid gland, typically present in serum at a concentration of 10-65 pg/mL (Aloia et al., *Endocr. Pract.* 12(2): 137-144 (2006)). Hypoparathyroidism, a rare disease characterized by PTH deficiency, can occur when an individual is born without the parathyroid gland (typically due to a chromosomal deletion). It can also result from the gland being damaged during a surgical procedure (e.g. thyroidectomy), when the organ is damaged due to an autoimmune response, iron accumulation, magnesium deficiency, or other idiopathic causes (Bilezikian et al., *J. Bone Miner. Res.* 26(10): 2317-2337 (2011)). A lack of PTH leads to hypocalcemia, hypercalciuria and hyperphosphatemia, which if left untreated causes persistent muscle cramps, paresthesia, seizures, and irregular heart rhythms (Shoback, *N. Engl. J. Med.* 359: 391-403 (2008)). Additionally, hypoparathyroidism patients suffer from cognitive disorders such as anxiety, depression, memory problems and general "brain fog" (Aggarwal et al., Eur. J. Endocrin. 168: 895-903 (2013)).

EXT607 and EXT608 were designed to extend the serum half-life of PTH and achieve a pharmacokinetic profile that more closely resembles physiological PTH levels. Vitamin D conjugation was used to modify PTH to create EXT607 and EXT608. A version of 25-hydroxycholecalciferol [25 (OH)-vitamin D] is attached to the C-terminus of PTH(1-34) via a small molecular weight poly(ethylene glycol) (PEG) spacer moiety (<2 kDa). The version of 25(OH)-vitamin D that is used is a non-active, "storage" form of vitamin D that has no activity at the vitamin D receptor (VDR); therefore, the vitamin D that is conjugated to the peptide is unlikely to interfere with normal vitamin D metabolism pathways (Lips, *Prog. Biophy. Mol. Biol.* 92: 4-8 (2006)). Because the modification is very small (<2.4 kDa), it does not affect the potency of PTH(1-34) as would be expected for a peptide with a larger modification such as 20 kDa PEG. EXT607/EXT608 displays protracted pharmacokinetics after subcutaneous dosing with a terminal half-life of 8-15 hr in rats and 24-32 hr in NHP.

In some embodiments, EXT607 and EXT608 are held in circulation via interaction with VDBP for an extended period of time. The half-life of EXT607 and EXT608 compared to PTH(1-34) is significantly improved. The half-life of PTH(1-34) in rats increases from 11 min to 8-15 hours following vitamin D conjugation, and in NHP, the half-life is 24-32 hours.

The carrier molecules are attached to PTH using chemistries described herein, described in WO2013172967, and WO2016065042, incorporated herein by reference in their entirety, or that are otherwise known in the art. The carriers improve the potency, absorption, bioavailability, circulating half-life or pharmacokinetic properties of the therapeutic compounds. In certain embodiments, the carriers further comprise what will be described herein as a "scaffold" that acts, among other things, as a non-releasable "spacer" between the targeting group and the therapeutic compound. In other embodiments, the carriers lack a scaffold.

The carriers are designed to be suitable for use in humans and animals. The carriers serve the purpose of improving the pharmacokinetic properties of a biological or chemical entity that is coupled, conjugated, or fused to the carrier. This occurs through the interaction of the targeting group with DBP. DBP can actively transport molecules quickly and effectively from the site of administration to the circulating plasma, thereby reducing exposure of the drug to degradative enzymes. The carriers, by binding to DBP, also improve the circulating half-life of the drug. This increases the potency and therapeutic efficacy of the drug by preventing kidney filtration and other elimination processes.

In describing and claiming one or more embodiments of the present invention, the following terminology will be used in accordance with the definitions described below.

The term "absorption" is the movement of a drug into the bloodstream. A drug needs to be introduced via some route of administration (e.g. oral, topical or dermal, subcutaneous, intramuscular, or intravenous) or in a specific dosage form such as a tablet, patch, capsule or liquid.

An "antagonist" refers to a molecule capable of neutralizing, blocking, inhibiting, abrogating, reducing or interfering with the activities of a particular or specified protein, including its binding to one or more receptors in the case of a ligand, or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of proteins, hormones, or other bioactive molecules. Antagonists may be fusion proteins, receptor molecules, antisense molecules, aptamers, ribozymes, or derivatives that bind specifically to the proteins, hormones, or other bioactive molecules and thereby sequester its binding to its target.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules that generally lack antigen specificity. Polypeptides of the latter kind are, for example, produced at low levels by the lymph system and at increased levels by myelomas.

"Aptamers" are nucleic acid-based compounds that have been selected to bind a specific target. An example of an aptamer-based therapeutic compound can be found in WO07/035922, incorporated by reference herein in its entirety.

The term "bioavailability" refers to the fraction of an administered dose of unchanged drug that reaches the systemic circulation, one of the principal pharmacokinetic properties of drugs. When a medication is administered intravenously, its bioavailability is 100%. When a medication is administered via other routes (such as orally), its bioavailability generally decreases (due to incomplete absorption and first-pass metabolism) or may vary from patient to patient. Bioavailability is an important parameter in pharmacokinetics that is considered when calculating dosages for non-intravenous routes of administration.

"Carriers" are compounds that can be conjugated to, fused to, coupled to or formulated with therapeutic compounds to improve the absorption, half-life, bioavailability, pharmacokinetic or pharmacodynamic properties of the drugs. They comprise a targeting group, a coupling group, and optionally, a scaffold moiety. In some embodiments, carriers may carry a therapeutic compound from the site of subcutaneous injection into circulation as well as carry the therapeutic compound in circulation for an extended period of time.

An "effective amount" refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

"Half-life" is a scientific term known in the art that refers to the amount of time that elapses when half of the quantity of a test molecule is no longer detected. An in vivo half-life refers to the time elapsed when half of the test molecule is no longer detectable in circulating serum or tissues of a human or animal.

A "hormone" is a biological or chemical messenger that communicates between one cell (or group of cells) to another cell. As described herein, hormones for use in the invention may be peptides, steroids, pheromones, interleukins, lymphokines, cytokines, or members of other hormone classes known in the art.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a preferred embodiment, homologous or derivative sequences share at least an 80 or 85 percent sequence identity. In a more preferred embodiment, homologous or derivative sequences share at least an 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers (1995), incorporated by reference herein in its entirety.

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Morpholinos" are synthetic molecules that are non-natural variants of natural nucleic acids that utilize a phosphorodiamidate linkage, described in U.S. Pat. No. 8,076,476, incorporated by reference herein in its entirety.

"Nucleic acids" are any of a group of macromolecules, either DNA, RNA, or variants thereof, that carry genetic information that may direct cellular functions. Nucleic acids may have enzyme-like activity (for instance ribozymes) or may be used to inhibit gene expression in a subject (for instance RNAi). The nucleic acids used in the inventions described herein may be single-stranded, double-stranded, linear or circular. The inventions further incorporate the use of nucleic acid variants including, but not limited to, aptamers, PNA, Morpholino, or other non-natural variants of nucleic acids. By way of example, nucleic acids useful for the invention are described in U.S. Pat. No. 8,076,476, incorporated by reference herein in its entirety.

"Patient response" or "response" can be assessed using any endpoint indicating a benefit to the patient, including, without limitation, (1) inhibition, to some extent, of disease progression, including stabilization, slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

As used herein, the term "peptide" is any peptide comprising two or more amino acids. The term peptide includes short peptides (e.g., peptides comprising between 2-14 amino acids), medium length peptides (15-50) or long chain peptides (e.g., polypeptides or proteins). The terms peptide, medium length peptide and protein may be used interchangeably herein. As used herein, the term "peptide" is interpreted to mean a polymer composed of amino acid residues, related naturally occurring structural variants, and synthetic non-naturally occurring analogs thereof linked via peptide bonds, related naturally-occurring structural variants, and synthetic non-naturally occurring analogs thereof. Synthetic peptides can be synthesized, for example, using an automated peptide synthesizer. Peptides can also be synthesized by other means such as by cells, bacteria, yeast or other living organisms. Peptides may contain amino acids other than the 20 gene-encoded amino acids. Peptides include those modified either by natural processes, such as processing and other post-translational modifications, but also by chemical modification techniques. Such modifications are well described in basic texts and in more detailed monographs, and are well-known to those of skill in the art. Modifications occur anywhere in a peptide, including the peptide backbone, the amino acid side chains, and the amino or carboxyl termini.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

The term "pharmacokinetics" is defined as the time course of the absorption, distribution, metabolism, and excretion of a therapeutic compound. Improved "pharmacokinetic properties" are defined as: improving one or more of the pharmacokinetic properties as desired for a particular therapeutic compound. Examples include but are not limited to: reducing elimination through metabolism or secretion, increasing drug absorption, increasing half-life, and/or increasing bioavailability.

"PNA" refers to peptide nucleic acids with a chemical structure similar to DNA or RNA. Peptide bonds are used to link the nucleotides or nucleosides together.

"Scaffolds" are molecules to which other molecules can be covalently or non-covalently attached or formulated. The scaffolds of the invention may act as "spacers" between the targeting group and the drug. Spacers are molecular entities that provide physical distance between the two distinct molecular entities. Scaffolds may also contain a reactive "linker" or may have beneficial therapeutic properties in addition to the drug. Linkers are the sites of attachment from one molecular entity to another. Thus, the scaffolds of the invention may be, for example, PEG, serum albumin, thioredoxin, an immunoglobulin, a modifying group that contains a reactive linker, a water-soluble polymer, or a therapeutic compound. The scaffolds and linkers of the invention are stable (i.e. non-releasable). Non-releasable linkers have more stable chemical bonds than releasable linkers to allow the attached molecular entities to remain attached in vivo. In certain embodiments, however, they may be "releasable" under specific conditions. Releasable linkers have inherent instability and allow for the release of the attached molecules under certain conditions over time.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µl/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

The "therapeutic compounds" typically refer to small molecules, chemical entities, nucleic acids, nucleic acid derivatives, peptides, peptide derivatives, naturally-occurring proteins, non-naturally-occurring proteins, glycoproteins, and steroids that are administered to subjects to treat diseases or dysfunctions or to otherwise affect the health of individuals. The term "therapeutic compound" as used herein has essentially the same meaning as the terms "drug" or "therapeutic agent." The therapeutic compounds of the present invention are PTH proteins and derivatives.

As used herein, "treatment" refers to clinical intervention in an attempt to alter the natural course of the individual or cell being treated and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "vitamin" is a recognized term in the art and is defined as a fat-soluble or water-soluble organic substance essential in minute amounts for normal growth and activity of the body and is obtained naturally from plant and animal foods or supplements.

"Vitamin D" is a group of fat-soluble secosteroids. Several forms (vitamers) of vitamin D exist. The two major forms are vitamin $D_2$ or ergocalciferol, and vitamin $D_3$ or cholecalciferol. Vitamin D without a subscript refers to vitamin $D_2$, $D_3$ or other forms known in the art. In humans, vitamin D can be ingested as cholecalciferol (vitamin $D_3$) or ergocalciferol (vitamin $D_2$). Additionally, humans can synthesize it from cholesterol when sun exposure is adequate. Cholecalciferol may be modified in the liver or in vitro to 25-hydroxycholecalciferol ("25-hydroxy Vitamin D"). In the kidney or in vitro, 25-hydroxy vitamin D can be modified into the distinct hormonal form of 1, 25-hydroxy vitamin D.

"Vitamin D binding protein," "DBP," or "VDBP" is a naturally circulating serum protein found in all mammals that, among other activities, can bind to and transport vitamin D and its analogs to sites in the liver and kidney where the vitamin is modified to its active form, and it retains vitamin D in its various forms in circulation for, on average, 30 days in humans. A DBP protein sequence is disclosed in SEQ ID NO:4 and an exemplary nucleic acid sequence encoding the DBP protein sequence is disclosed in SEQ ID NO:5. DBP has multiple naturally-occurring isoforms. Exemplary isoforms are available in the public sequence databases (e.g. Accession Nos. NM_001204306.1, NM_001204307.1, NM_000583.3, BC036003.1, M12654.1, X03178.1, AK223458, P_001191235.1, NP_000574.2, AAA61704.1, AAD13872.1, NP_001191236.1, AAA19662.2, 154269, P02774.1, EAX05645.1, AAH57228.1, AAA52173.1, AAB29423.1, AAD14249.1, AAD14250.1, and BAD97178.1).

The invention contemplates non-hormonal vitamin D conjugates that bind DBP or functional DBP variants and homologs that contain conservative or non-conservative amino acid substitutions that substantially retain DBP activity. DBP binding molecules or functional DBP variants may be identified using known techniques and characterized using known methods (Bouillon et al., J Bone Miner Res. 6(10):1051-7 (1991), Teegarden et. al., Anal. Biochemistry 199(2):293-299 (1991), McLeod et al, J Biol Chem. 264(2): 1260-7 (1989), Revelle et al., J. Steroid Biochem. 22:469-474 (1985)). The foregoing references are incorporated by reference herein in their entirety.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like.

The invention provides effective routes for administration of proteins, peptides, other biologics, nucleic acids, and small molecule drugs. The invention further provides effective routes of drug administration via transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir modes.

In addition, the inventions described herein provide compositions and methods for maintaining target binding activity, i.e. pharmacodynamics (PD), for therapeutic compounds. It further provides compositions and methods for improving the pharmacokinetic (PK) profiles of therapeutic compounds as described herein. The invention further provides compositions and methods for improved drug absorption profiles as compared to the drug absorption profiles for the drugs using the same routes of administration or different routes of administration but without the inventions described herein. The invention further provides compositions and methods for improved drug bioavailability profiles as compared to the drug bioavailability profiles for the drugs using the same routes of administration or different routes of administration but without the carriers described herein. The invention further provides compositions and methods for improved drug half-life profiles as compared to the drug half-life profiles for the drugs using the same routes of administration or different routes of administration but without the inventions described herein.

The invention also provides alternative routes of drug administration that are more cost-effective or favorable to the patients when compared to the drugs without the inventions described herein.

The non-hormonal vitamin D carriers disclosed herein may improve the absorption, half-life, bioavailability, or pharmacokinetic properties of the linked PTH. While not wishing to be bound by theory, the carriers have the properties of binding to the body's natural DBP. DBP may transport the carrier-drug complex from the site of administration to the circulating serum. The vitamin D-DBP interaction may retain the therapeutic compounds in circulation for an extended period of time. This can prevent its excretion from the body and increase the exposure of the therapeutic compound in the body to achieve a longer lasting therapeutic effect. Additionally, a smaller dose of drug may be required when conjugated the carrier when compared to the unmodified form.

The therapeutic compound carrier conjugates of the invention typically have about 1, 2, 3, 4, 5, 6, 7, 8, 9, or 10 targeting groups individually attached to a therapeutic compound. The structure of each of the targeting groups attached to the therapeutic compound may be the same or different. In preferred embodiments, one or more targeting groups are stably or non-releasably attached to the therapeutic compound at the N-terminus, C-terminus, or other portion of a therapeutic protein. For example, a therapeutic compound carrier conjugate may comprise a targeting group attached to the N-terminus and additionally a targeting group attached to a lysine residue. In another embodiment, a therapeutic compound carrier conjugate has a targeting group attached to a therapeutic protein via a modification such as a sugar residue as part of a glycosylation site, or on an acylation site of a peptide or attached to a phosphorylation site or other natural or non-natural modifications that are familiar to one skilled in the art. Also contemplated are attachment sites using a combination of sites mentioned above. One preferred embodiment of the present invention comprises a targeting group that is attached to the therapeutic compound at one specific site on a therapeutic compound. In another preferred embodiment, the attachment site on a protein may be a cysteine, lysine, the N-terminus or C-terminus.

In another embodiment, the scaffold is a pharmaceutically acceptable carrier. In preferred embodiments, the scaffold is poly(ethylene glycol), polylysine, polyethyleneimine, poly(propyleneglycol), a peptide, serum albumin, thioredoxin, an immunoglobulin, an amino acid, a nucleic acid, a glycan, a modifying group that contain a reactive linker, a water-soluble polymer, a small carbon chain linker, or an additional therapeutic moiety.

The scaffolds of the invention are discrete in length to facilitate manufacture, solubility, detection, and pharmaceutical efficacy. In one embodiment, soluble scaffold moieties have some detectable degree of solubility in aqueous or non-aqueous solutions. Methods to detect and/or quantify water solubility are well known in the art. Exemplary water-soluble polymers include peptides, saccharides, poly(ethers), poly(amines), poly(carboxylic acids) and the like.

Peptides can have mixed sequences or be composed of a single amino acid, e.g., poly(lysine). An exemplary polysaccharide is poly(sialic acid). An exemplary poly(ether) is poly(ethylene glycol), e.g. m-PEG. Poly(ethyleneimine) is an exemplary polyamine, and poly(acrylic) acid is a representative poly(carboxylic acid). The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched.

Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), polylysine, polyethyleneimine, poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of about 100 Da to about 100,000 Da.

In other embodiments, the scaffold moiety may be a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic compound. In one embodiment, the scaffold moieties are non-toxic to humans and animals. In another embodiment, the scaffolds are endogenous serum proteins. In another embodiment, the scaffold moieties are water-soluble polymers. In another embodiment, the scaffolds are non-naturally-occurring polymers. In another embodiment, the scaffolds are naturally-occurring moieties that are modified by covalent attachment to additional moieties (e.g., PEG, poly(propylene glycol), poly(aspartate), biomolecules, therapeutic moieties, or diagnostic moieties). The scaffolds and linkers of the invention are stable (i.e. non-releasable). In certain embodiments, however, they may be "releasable" under specific conditions.

The conjugation of hydrophilic polymers, such as PEG, is known in the art. In its most common form, PEG is a linear polymer terminated at each end with hydroxyl groups: HO—CH2CH2O—(CH2CH2O)x-CH2CH2-OH where x typically ranges from about 3 to about 4000. In a preferred embodiment, the PEG has a molecular weight distribution that is essentially homodisperse. In another preferred embodiment, the PEG is a linear polymer. In another preferred embodiment the PEG is a branched polymer.

Many end-functionalized or branched derivatives and various sizes are known in the art and commercially available. By way of example, conjugation of the PEG or poly(ethylene oxide) (also known as PEO) may be carried out using the compositions and methods described herein and in U.S. Pat. No. 7,803,777 (Defrees et al.) and U.S. Pat. No. 4,179,337 (Davis et al.), each of which are incorporated by reference herein in their entirety.

In some embodiments, the therapeutic compounds are paired with smaller scaffold moieties or larger scaffold moieties. It is contemplated that the therapeutic compounds could be paired with a scaffold moiety of 1 Da to 10 kDa. In some embodiments, a scaffold that is approximately equal to the molecular weight of a small therapeutic compound results in an efficacious carrier-drug conjugate. Improvements in efficacy may be obtained by empirically adjusting the scaffold size further. Without wishing to be bound by theory, the pharmacokinetic properties and efficacy of the conjugates may be enhanced when a scaffold (in combination with linkers as needed) is big enough to ablate potential steric hindrance of the drug by DBP binding and vice versa. Thus, a therapeutic compound is conjugated so that its active region is exposed and available for functional activity and the carrier is able to bind DBP. Additional embodiments provide non-releasable attachments that extend the circulation of therapeutics. In some small peptide embodiments such as PTH, the scaffold may be selected to be approximately equal to the molecular weight of the therapeutic.

In preferred embodiments, the conjugation of the therapeutic compound retains a portion of, or substantially all of, its activity following the conjugation. The active region of given therapeutic may be known in the art or determined empirically. In other embodiments, the conjugate is therapeutically active while remaining linked to the carrier. This embodiment may maximize the time in circulation and as well as its efficacy.

The scaffolds of the present invention, for example, could have a molecular weight of 100 Daltons (Da.), 500 Da., 1000 Da., 2000 Da., 5000 Da., 10,000 Da., 15,000 Da., 20,000 Da., 30,000 Da., 40,000 Da. or 60,000 Da. In one embodiment of the invention, “small” scaffolds may be between about 100 Da. and 20,000 Da. In another embodiment, “large” scaffolds may be greater than about 20,000 Da. to about 200,000 Da. In preferred embodiments, the scaffold moiety is between about 100 Da. and 200,000 Da. In more preferred embodiments, the scaffold is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 20.00 Da. and 200,000 Da., 100,000 and 200,000 Da., 5000 Da. and 100,000 Da., 10,000 Da. and 80,000 Da., 20,000 Da. and 60,000 Da., or 20,000 Da. and 40,000 Da. The size of the scaffolds may be varied to maximize absorption, bioavailability, circulating half-life, or efficacy of the conjugated therapeutic compound.

Another component of the carrier molecule preferably comprises a coupling group that is used to covalently attach the drug to the scaffold or the carrier. The coupling groups of the invention include an amine-reactive group, a thiol-reactive group, a maleimide group, a thiol group, an aldehyde group, an N-hydroxysuccinimide (NHS)-ester group, a haloacetyl group, an iodoacetyl group, a bromoacetyl groups, a Succinimidyl-4-(N-maleimidomethyl)cyclohexane-1-carboxylate (SMCC) group, a sulfo SMCC group, a carbodiimide group and bifunctional cross-linkers such as NHS-maleimido, combinations thereof, or other coupling groups familiar to persons skilled in the art. The coupling groups of the invention can promote thiol linkages, amide linkages, oxime linkages, hydrazone linkages, thiazolidinone linkages or utilize cycloaddition reactions also called click chemistry to couple the carrier to a therapeutic compound. In another embodiment, the composition preferably includes a combination of one or more therapeutic compounds attached to the coupling group of the scaffold molecule. The linkers of the invention may be between about 40 and 100 Daltons. In preferred embodiments, the linkers may be between about 40-50, 50-60, 60-70, 70-80, 80-90, or 90-100 Daltons. The linkers may also be varied to affect the stability or releasability of the link between the carrier and the therapeutic compound.

NHS groups are known to those skilled in the art as being useful for coupling to native peptides and proteins without having to engineer in a site of attachment. NHS groups allow attachment to most proteins and peptides that contain amino acids with amine groups such as a lysine residue. Utilization of NHS groups allows for flexibility in the site of carrier conjugation as protein structure and reaction time can influence the attachment site and number of carrier molecules conjugated to the therapeutic compound. By way of example, controlling the molar ratio of NHS-carrier to therapeutic compound, one skilled in the art can have some control over the number of carrier molecules attached to the therapeutic compound thus allowing for more than one carrier to be conjugated to a given therapeutic compound, if desired.

Conjugation of the carrier to a therapeutic compound is achieved by mixing a solution of the molecules together in a specific molar ratio using compatible solutions, buffers or solvents. For example, a molar ratio of about 1:1, 2:1, 4:1, 5:1, 10:1, 20:1, 25:1, 50:1, 100:1, 1000:1, or about 1:2, 1:4, 1:5, 1:10, 1:20 1:25, 1:50, 1:100 or 1:1000 of carrier to therapeutic compound could be used. By varying the ratio, this could result in different numbers of individual carriers attached to the therapeutic compound, or could help to select a specific site of attachment. Attachment of the carriers is also pH, buffer, salt and temperature dependent and varying these parameters among other parameters can influence the site of attachment, the number of carriers attached, and the speed of the reaction. For example, by selecting a pH for the reaction at or below pH 6 could help selectively conjugate an aldehyde version of the carrier to the N-terminus of the therapeutic protein or peptide.

Additionally, in order to retain substantially the same activity of the therapeutic compounds, conjugation to the carriers will be at a site on the molecules that do not interfere with therapeutic function. For proteins, it may require conjugation to the amino terminus, the carboxy terminus, or to an internal reactive amino acid. For nucleic acids, it may require conjugation to the 5' end, the 3' end, or an internal nucleotide, nucleoside, or a derivative thereof. In one embodiment, the carrier is conjugated to a nucleotide or nucleoside prior to incorporation into a polynucleotide molecule.

The invention provides a pharmaceutical carrier comprising a formula I:

$$B\text{-}(L)^a\text{-}S\text{-}(M)^b\text{-}C \qquad \text{I}$$

Wherein:

B is a targeting group that is a non-hormonal vitamin D, analog, or metabolite thereof conjugated to $(L)^a$;

S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, polylactic acid, a water-soluble polymer, a small carbon chain linker, or an additional therapeutic moiety;

C is an amine-reactive group, a thiol-reactive group, a maleimide group, a thiol group, a disulfide group, an aldehyde group, an NHS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-maleimido or combinations thereof;

$(L)^a$ and $(M)^b$ are linkers independently selected from $-(CH_2)_n-$, $-C(O)NH-$, $-HNC(O)-$, $-C(O)$ O—, —OC(O)—, —O—, —S—S—, —S—, —S(O)—, —S(O)$_2$— and —NH—;
a is an integer from 0-4; and
b is an integer from 0-4; and
n is an integer from 0-3.

In preferred embodiments, the present invention provides carriers that include those of formula I:

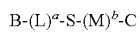   I

Wherein:
B is a targeting group selected from vitamin D, a vitamin D analog, a vitamin D-related metabolite, an analog of a vitamin D related-metabolite, or a small carbon-based molecule that binds DBP;
S is a scaffold moiety, comprising poly(ethylene glycol), polylysine, poly(propyleneglycol), a peptide, serum albumin, an amino acid, a nucleic acid, a glycan, polylactic acid, a water-soluble polymer, or a small carbon chain linker; C is a maleimide group, a thiol group, a disulfide group, an aldehyde group, an NHS-ester group, an iodoacetyl group, or a bromoacetyl group;
(L)$^a$ and (M)$^b$ are linkers independently selected from —(CH$_2$)$_n$—, —C(O)NH—, —HNC(O)—, —C(O)O—, —OC(O)—, —O—, —S—S—, —S—, —S(O)—, —S(O)$_2$— and —NH—;
a is an integer from 0-4; and
b is an integer from 0-4; and
n is an integer from 0-3.

In more preferred embodiments, the present invention provides carriers that include those of formula I:

B-(L)$^a$-S-(M)$^b$-C   I

Wherein:
B is a targeting group selected from vitamin D, a vitamin D analog, or a vitamin D-related metabolite;
S is a scaffold moiety, comprising poly(ethylene glycol), polylysine or poly(propyleneglycol);
C is a maleimide group, a disulfide group, an aldehyde group, an NHS-ester group or an iodoacetyl group;
(L)$^a$ and (M)$^b$ are linkers independently selected from —(CH$_2$)$_n$—, —C(O)NH—, —HNC(O)—, —C(O)O—, —OC(O)—, —O—, —S—S—, —S—, —S(O)—, —S(O)$_2$— and —NH—;
a is an integer from 0-4; and
b is an integer from 0-4; and
n is an integer from 0-3.

In some preferred embodiments, the present invention provides carriers that include those of formulas IIa, IIb, and IIc:

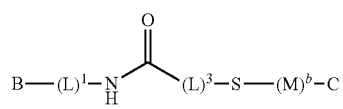   IIa

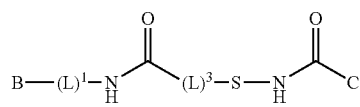   IIb

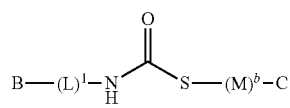   IIc

Wherein:
B is a targeting group selected from vitamin D, a vitamin D analog, or a vitamin D-related metabolite;
S is a scaffold moiety, comprising poly(ethylene glycol), or poly(propyleneglycol); and
C is a maleimide group, a disulfide group, an aldehyde group, an NHS-ester group or an iodoacetyl group;
L$^1$ is —(CH$_2$)$_n$—;
L$^3$ is —(CH$_2$)$_o$—;
(M)$^b$ are linkers independently selected from —(CH$_2$)$_n$—, —C(O)NH—, —HNC(O)—, —C(O)O—, —OC(O)—, —O—, —S—S—, —S—, —S(O)—, —S(O)$_2$— and —NH—;
b is an integer from 0-4; and
n is 3; and
is 1.

In WO13/172967, which is incorporated herein by reference, conjugation at the Carbon 25 (C25) position of 25-hydroxy-vitamin D$_3$ is exemplified. In WO2016/065042, conjugation at the Carbon 3 (C3) position of 25-hydroxy-vitamin D$_3$ is exemplified.

In certain most preferred embodiments of formula IIa, B is represented by formula III, S is poly(ethylene glycol) and (M)$^b$-C is represented by formula IVa.

   IVa

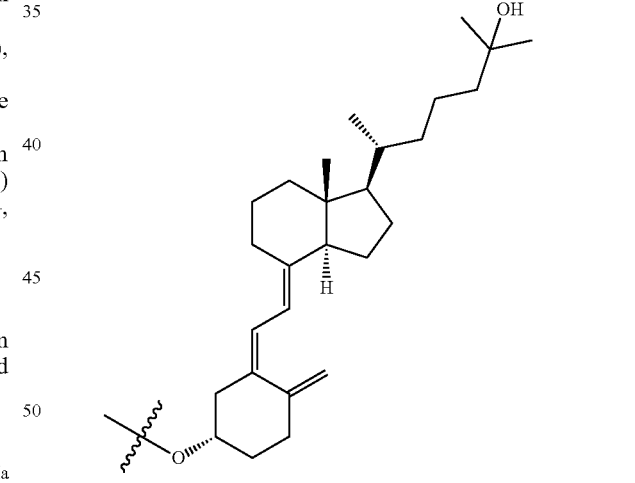   III

In certain most preferred embodiments of formula IIb, B is represented by formula III, S is poly(ethylene glycol) and (M)$^b$-C is represented by formula IVb.

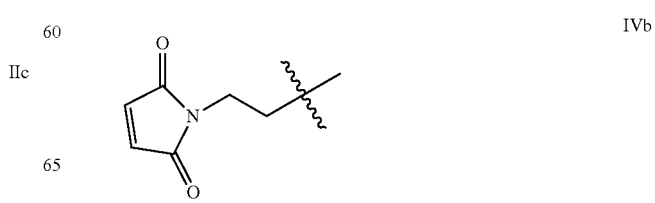   IVb

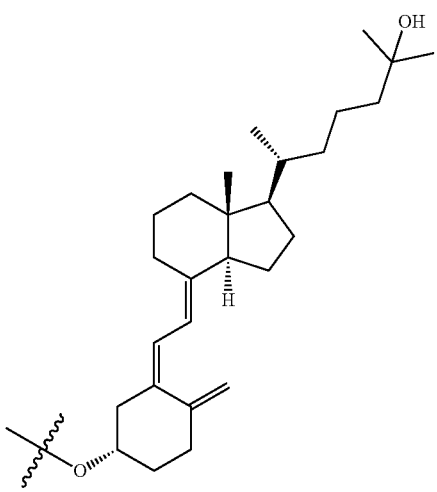

III

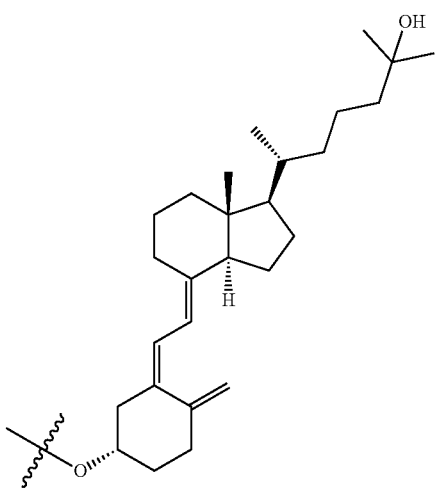

III

In certain most preferred embodiments of formula IIc, B is represented by formula III, S is poly(ethylene glycol) and $(M)^b$-C is represented by formula IVc.

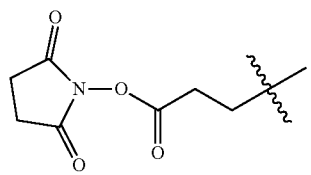

IVc

In certain most preferred embodiment, S is between about 100 Da. and 200,000 Da. In other most preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 5000 Da. and 100,000 Da., 10,000 Da. and 80,000 Da., 20,000 Da. and 60,000 Da., or 20,000 Da. and 40,000 Da.

In a specific embodiment, the present invention provides a carrier represented by formula V.

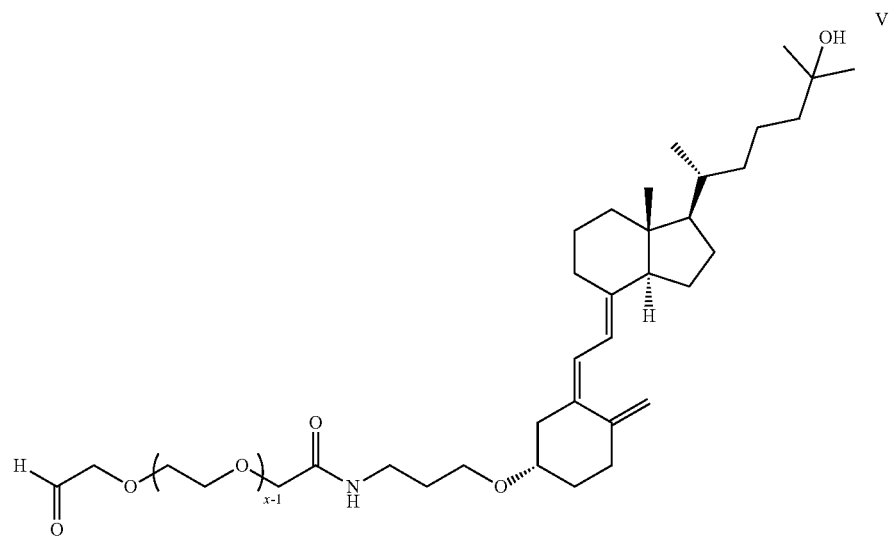

V

In formula V, x−1 refers to the fact that upon conjugation of PEG with x number of polymers in this reaction, the end PEG monomer is converted to an aldehyde so the final formulation is x−1. In another specific embodiment, the present invention provides a carrier represented by formula VI.

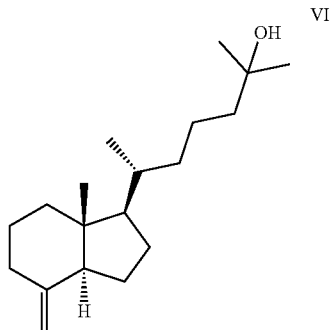

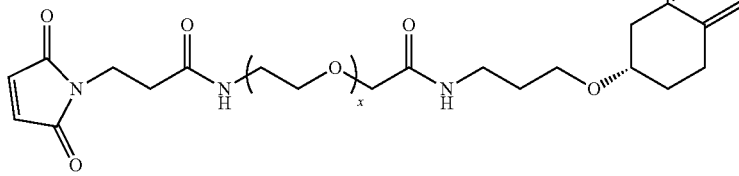

In formula VI, x refers to the number of repeating ethylene glycol units. In another specific embodiment, the present invention provides a carrier represented by formula VII.

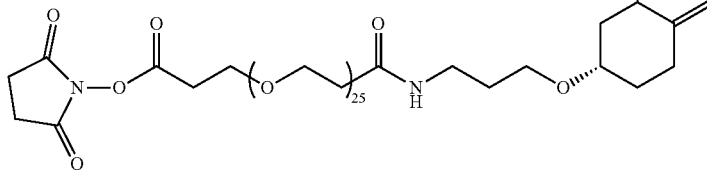

In certain embodiments, the present invention provides a method for producing a carrier of formula I:

B-(L)$^a$-S-(M)$^b$-C    I comprising the step of reacting a compound of formula Ia:

B-L$^1$-NH$_2$    Ia with a compound of formula Ib:

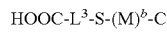

HOOC-L$^3$-S-(M)$^b$-C    Ib in the presence of an amide coupling agent,
wherein B, S, C and L$^1$, L$^3$, and (M)$^b$ are defined as above and L$^2$ is —C(O)NH—.

One skilled in the art will recognize that a compound of formula Ia can be used either as a free base or as a suitable salt form. Suitable salt forms include, but are not limited to trifluoroacetic acid (TFA), hydrochloric acid (HCl), hydrobromic acid (HBr), methanesulfonic acid (MsOH), (trifluoromethanesulfonic acid) TfOH, and acetic acid (AcOH).

Any suitable amide coupling agent may be used to form a compound of formula I. Suitable amide coupling agents include, but are not limited to 2-chloromethylpyridinium iodide, [benzotriazol-1-yl-oxy-tris-(dimethylamino)phosphonium hexa-fluorophosphate] (BOP), benzotriazol-1-yloxytripyrrolidinophosphonium hexafluorophosphate (PyBOP), 2-(1H-benzotriazol-1-yl)-1,1,3,3-tetramethyluronium hexafluorophosphate (HBTU), 1-[bis(dimethylamino)methylene]-1H-1,2,3-triazolo[4,5-b]pyridinium 3-oxid hexafluorophosphate (HATU), N,N'-dicyclohexylcarbodiimide (DCC), 1-ethyl-3-(3-dimethylaminopropyl)carbodiimide (EDCI), 2-(1H-benzotriazole-1-yl)-1,1,3,3-tetramethylaminium tetrafluoroborate (TBTU) and propanephosphonic acid anhydride (T3P). In certain embodiments, the amide coupling agent is used alone. In certain embodiments, the amide coupling agent is used with a co-reagent such as 1-hydroxybenzotriazole (HOBT) or N,N-dimethylpyridin-4-amine (DMAP). In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

One skilled in the art will recognize that any suitable leaving group may be coupled with the carboxylic acid of formula Ib in the presence of a suitable coupling agent to form an active ester of formula Ic:

$$HOOC-L^3-S-(M)^b-C \longrightarrow$$
Ib
$$ROOC-L^3-S-(M)^b-C$$
Ic wherein R is a suitable leaving group including, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCI, TBTU and T3P. In some embodiments, the present invention provides a method for producing a carrier of formula I:

$$B\text{-}(L)^a\text{-}S\text{-}(M)^b\text{-}C \qquad I$$

comprising the step of reacting a compound of formula Ia:

$$B\text{-}L^1\text{-}NH_2 \qquad Ia$$

with a compound of formula Ic:

$$ROOC\text{-}L^3\text{-}S\text{-}(M)^b\text{-}C \qquad Ic$$

wherein B, S, C, R and $L^1$, $L^3$, and $(M)^b$ are defined as above and $L^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

In certain other embodiments, the present invention provides a method for producing a carrier of formula IIa:

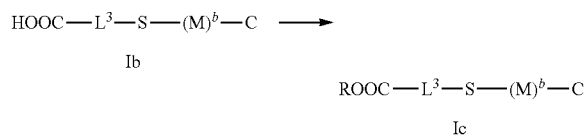

IIa comprising the steps of reacting a compound of formula Ia:

$$B\text{-}L^1\text{-}NH_2 \qquad Ia$$

with a compound of formula Id:

$$HOOC\text{-}L^3\text{-}S\text{-}(M)^b\text{-}CH_2OH \qquad Id$$

in the presence of an amide coupling agent forming a compound of formula Ie; and

Ie

Oxidation of the primary alcohol of formula Ie to an aldehyde of formula IIa;

IIa wherein B, S, $L^1$, $L^3$, $(M)^b$, b, n and o are defined as above and $L^2$ is —C(O)NH— and C is an aldehyde group.

Any suitable oxidizing agent may be used to form a compound of formula IIa. Suitable oxidizing agents include, but are not limited to, the Collins reagent, pyridinium dichromate (PDC), pyridinium chlorochromate (PCC), oxalyl chloride/DMSO (Swern oxidation), SO$_3$-pyridine/DMSO (Parikh-Doehring oxidation), Dess-Martin periodinane, tetrapropylammonium perruthenate/N-methylmorpholine N-oxide (TPAP/NMO), and 2,2,6,6-tetramethylpiperidin-1-yl)oxyl/sodium hypochlorite (TEMPO/NaOCl).

One skilled in the art will recognize that a compound of formula Ia can be used either as a free base or as a suitable salt form. Suitable salt forms include, but are not limited to TFA, HCl, HBr, MsOH, TfOH and AcOH.

Any suitable amide coupling agent may be used to form a compound of formula Ie. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In certain embodiments, any suitable leaving group can be coupled with a carboxylic acid of formula Id in the presence of a suitable coupling reagent to form an active ester of formula If:

$$HOOC-L^3-S-(M)^b-CH_2OH \longrightarrow$$
Id

-continued

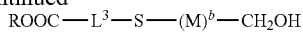
If wherein R is a suitable leaving group including, but are not limited to imidazole, HOBT, 2,3,5,6-tetrafluorophenol (TFP), NHS, and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, the present invention provides a method for producing a carrier of formula Ie:

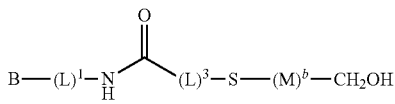
Ie comprising the step of reacting a compound of formula Ia;

Ia with a compound of formula If; and

ROOC-L³-S-(M)$^b$-CH$_2$OH    If

Oxidation of the primary alcohol of formula Ie to an aldehyde of formula IIa;

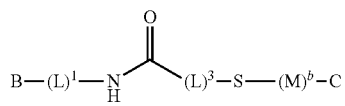
IIa wherein B, S, C, R and L$^1$, L$^3$, and (M)$^b$ are defined as above and L$^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

In certain embodiments, the amide coupling is performed with a base such as triethylamine or diisopropylethylamine. One skilled in the art will recognize that bases other than triethylamine or diisopropylethylamine may be used.

Any suitable oxidizing agent may be used to form a compound of formula IIa. Suitable oxidizing agents include, but are not limited to, the Collins reagent, PDC, PCC, oxalyl chloride/DMSO (Swern oxidation), SO$_3$-pyridine/DMSO (Parikh-Doehring oxidation), Dess-Martin periodinane, TPAP/NMO, and TEMPO/NaOCl.

In certain other embodiments, the present invention provides a method for producing a carrier of formula IIc:

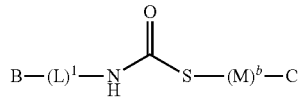
IIc comprising the steps of reacting a compound of formula Ia:

B-L$^1$-NH$_2$    Ia with a compound of formula Ig:

ROOC—S-(M)$^b$-COOH    Ig forming a compound of formula Ih; and

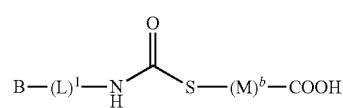
Ih

Converting a carboxylic acid of formula Ih to an active ester of formula IIc;

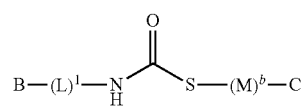
IIc wherein B, S, C, R, L$^1$, (M)$^b$, b, n and o are defined as above and L$^2$ is —C(O)NH—.

One skilled in the art will recognize that a compound of formula Ia can be used either as a free base or as a suitable salt form. Suitable salt forms include, but are not limited to TFA, HCl, HBr, MsOH, TfOH and AcOH.

Any suitable leaving group can be coupled with a carboxylic acid of formula Ih in the presence of a suitable coupling reagent to form an active ester of formula IIc. Suitable leaving groups include, but are not limited to imidazole, HOBT, 2,3,5,6-tetrafluorophenol (TFP), NHS and 4-nitrophenol. Suitable coupling reagents include, but are not limited to 2-chloromethylpyridinium iodide, BOP, PyBOP, HBTU, HATU, DCC, EDCI, TBTU and T3P.

In some embodiments, an active ester of formula IIc is formed from a carboxylic acid of formula Ih using a combination of a suitable leaving group and a coupling reagent.

In some embodiments, an active ester of formula IIc is formed from a carboxylic acid of formula Ih using a single reagent that produces a leaving group and also effects a coupling reaction. Such reagents include, but are not limited to 1,1'-carbonyldiimidazole, N,N'-disuccinimidyl carbonate, 4-nitrophenyl trifluoroacetate and HBTU. In some embodiments, the single reagent is used alone. In other embodiments, the single reagent is used with an acyl transfer catalyst. Such acyl transfer catalysts include, but are not limited to DMAP and pyridine. One skilled in the art will recognize that additional acyl transfer catalysts may be used.

In a specific embodiment, the present invention provides a method for producing a carrier represented by formula V:
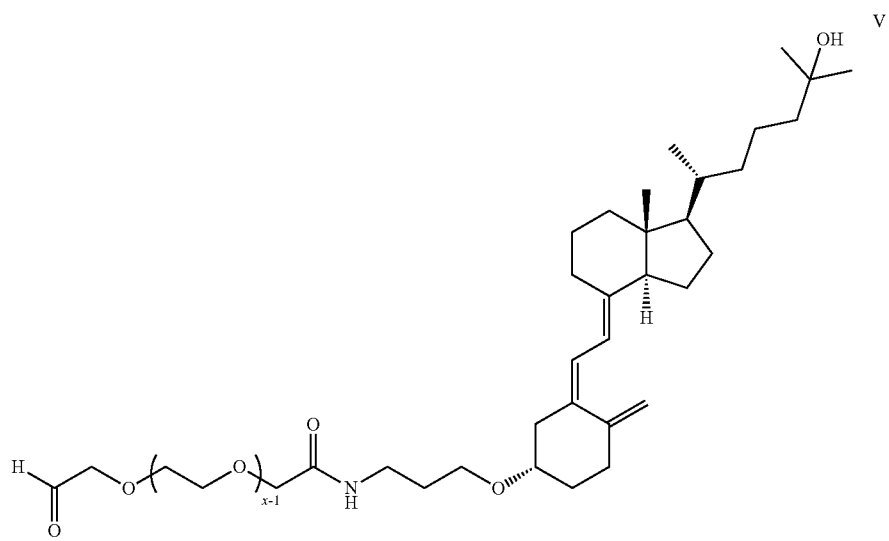
comprising the step of reacting a compound of formula Va:
with a compound of formula Vb:
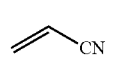
to form a compound of formula Vc;
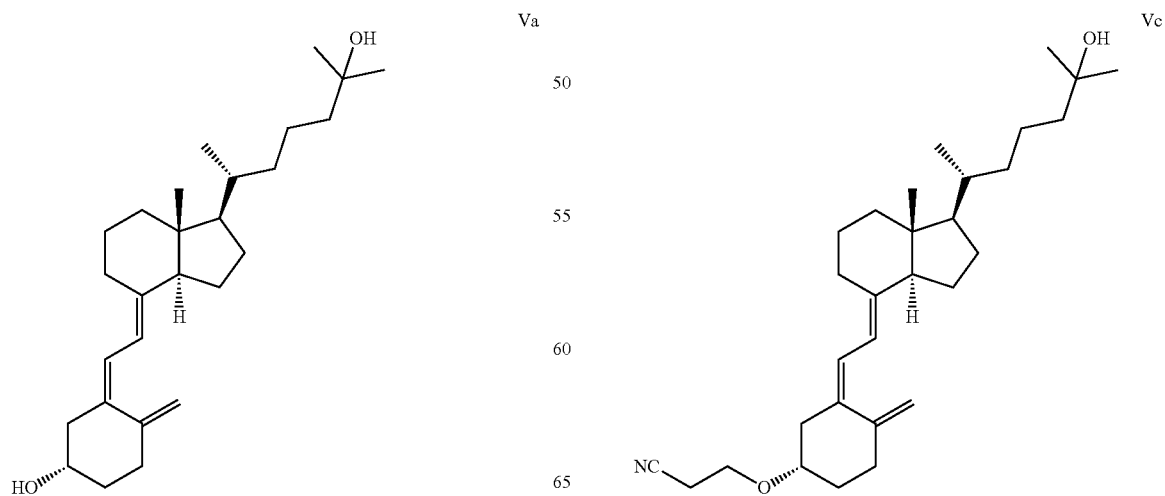

Reduction of the nitrile group to form the amine of formula Vd;
Reaction of the compound of formula Vd with a compound of formula Ve;
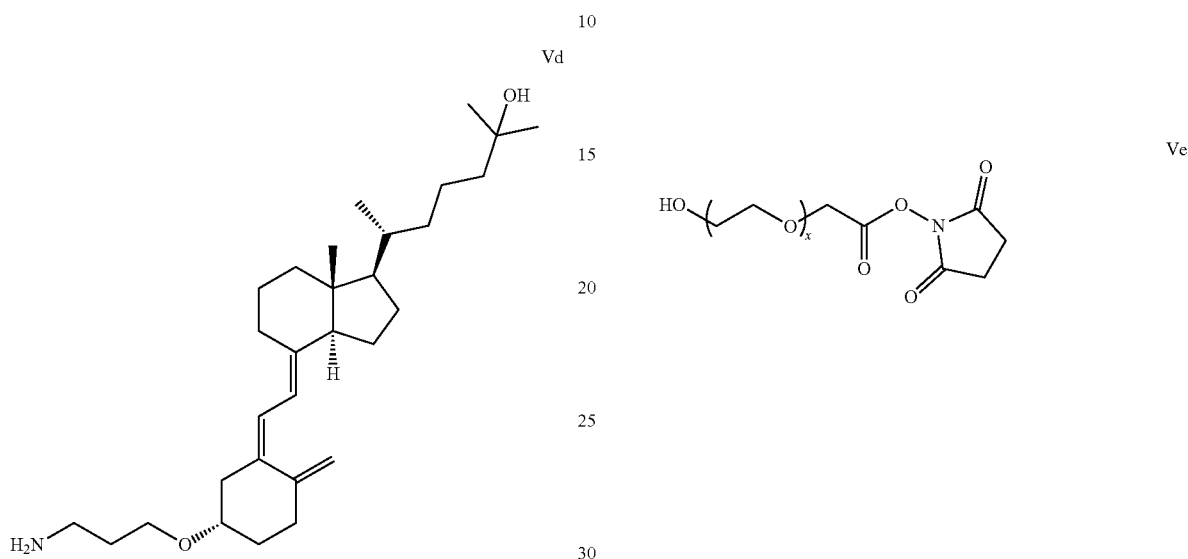
To form a compound of the formula Vf
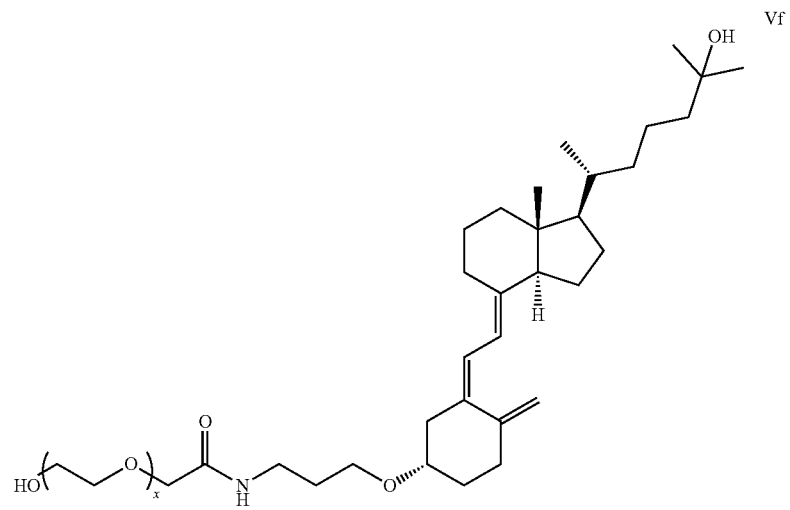

Oxidation of the primary alcohol of formula Vf to form the aldehyde of formula V.

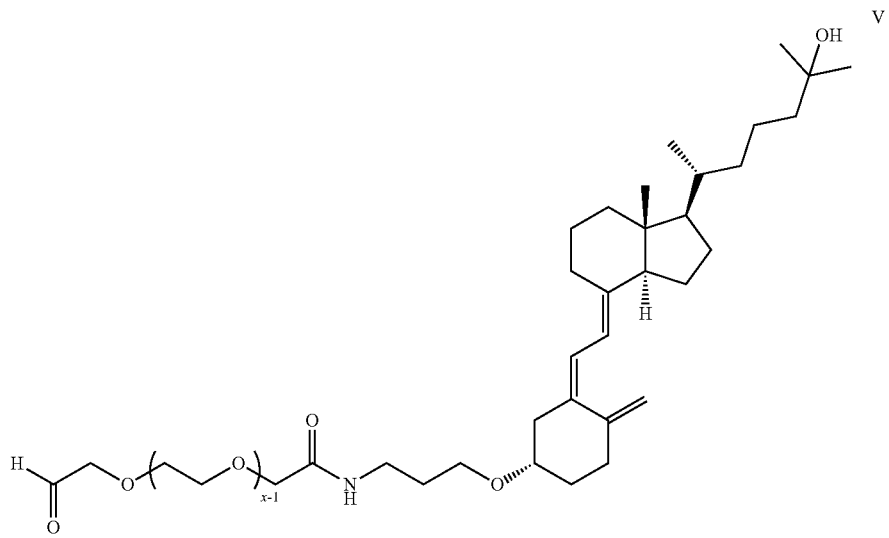

Here, x refers to the number of repeating ethylene glycol units and x−1 refers to the fact that upon conjugation of PEG with x number of polymers in this reaction, the end PEG monomer is converted to an aldehyde so the final formulation is x−1. In some embodiments, the reaction of a compound of formula Vb with a compound of formula Va is promoted by addition of Triton B. One skilled in the art will recognize that other reagents may be used to promote nucleophilic addition to acrylonitrile.

In some embodiments, reduction of the nitrile of formula Vc to the amine of formula Vd is performed using $AlCl_3$/lithium aluminium hydride (LAH). One skilled in the art will recognize that other reduction reagents may be used including sodium, $H_2$/Pd, $H_2$/Raney nickel, and diborane.

One skilled in the art will recognize that a compound of formula Vd can be used either as a free base or as a suitable salt form. Suitable salt forms include, but are not limited to TFA, HCl, HBr, MsOH, TfOH and AcOH.

In certain embodiments, a base such as triethylamine or diisopropylethylamine is used to promote coupling of the NHS-ester of formula Ve with the amine of formula Vd. One skilled in the art will recognize that bases other than triethylamine or diisopropylethylamine may be used.

Any suitable oxidizing agent may be used to form a compound of formula V. Suitable oxidizing agents include, but are not limited to, the Collins reagent, PDC, PCC, oxalyl chloride/DMSO (Swern oxidation), $SO_3$-pyridine/DMSO (Parikh-Doehring oxidation), Dess-Martin periodinane, TPAP/NMO, and TEMPO/NaOCl.

In another specific embodiment, the present invention provides a method for producing a carrier represented by formula VI:

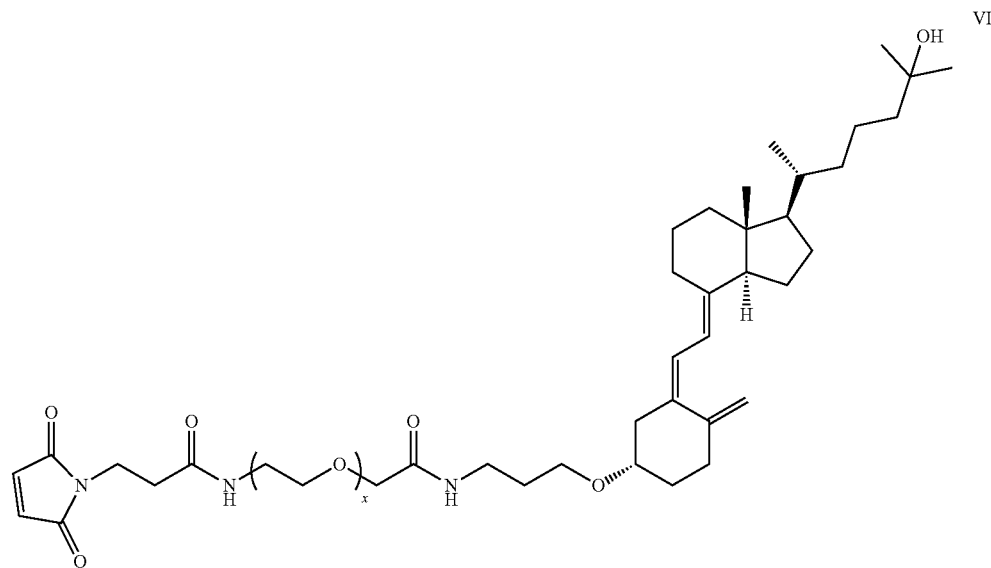

comprising the steps of reacting a compound of formula Vd:

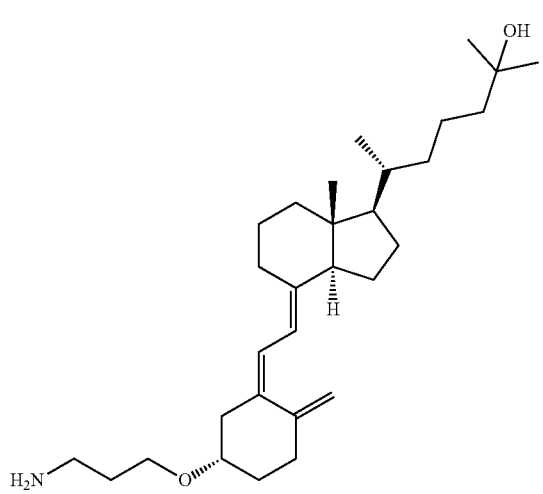

in the presence of an amide coupling agent with a compound of formula VIa:

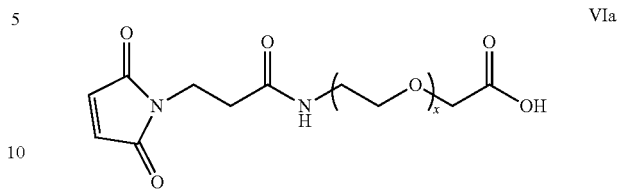

Here, x refers to the number of repeating ethylene glycol units. One skilled in the art will recognize that a compound of formula Vd can be used either as a free base or as a suitable salt form. Suitable salt forms include, but are not limited to TFA, HCl, HBr, MsOH, TfOH and AcOH.

In a preferred embodiment of formulae VI, Vd, VIa, x=36.

Any suitable amide coupling agent may be used to form a compound of formula VI. Suitable amide coupling agents include, but are not limited to 2-chloromethylpyridinium iodide, BOP, PyBOP, HBTU, HATU, DCC, EDCI, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In another specific embodiment, the present invention provides a method for producing a carrier represented by formula VII:

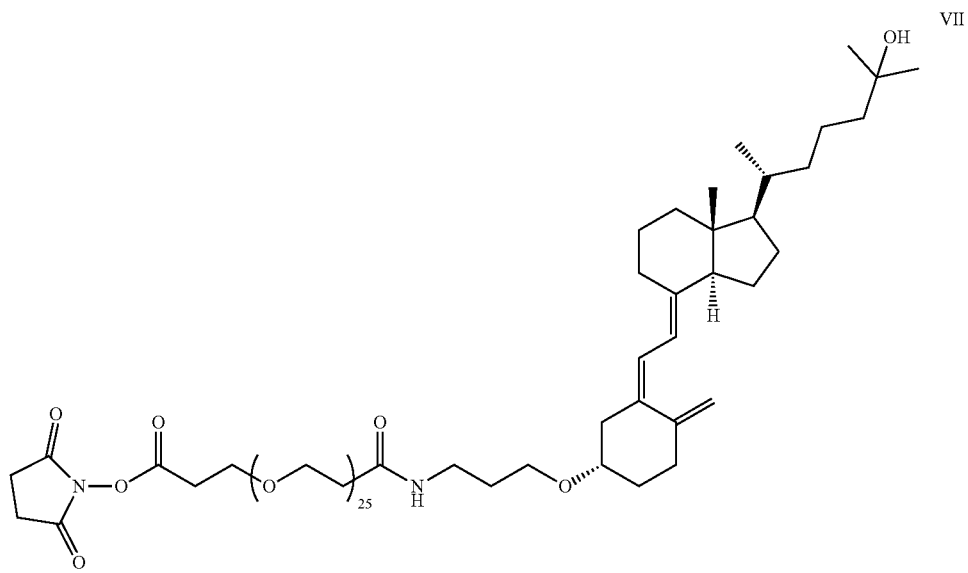

comprising the steps of reacting a compound of formula Vd:

with a compound of formula VIIa:

forming a compound of formula VIIb; and

Converting a carboxylic acid of formula VIIb to an active ester of formula VII;

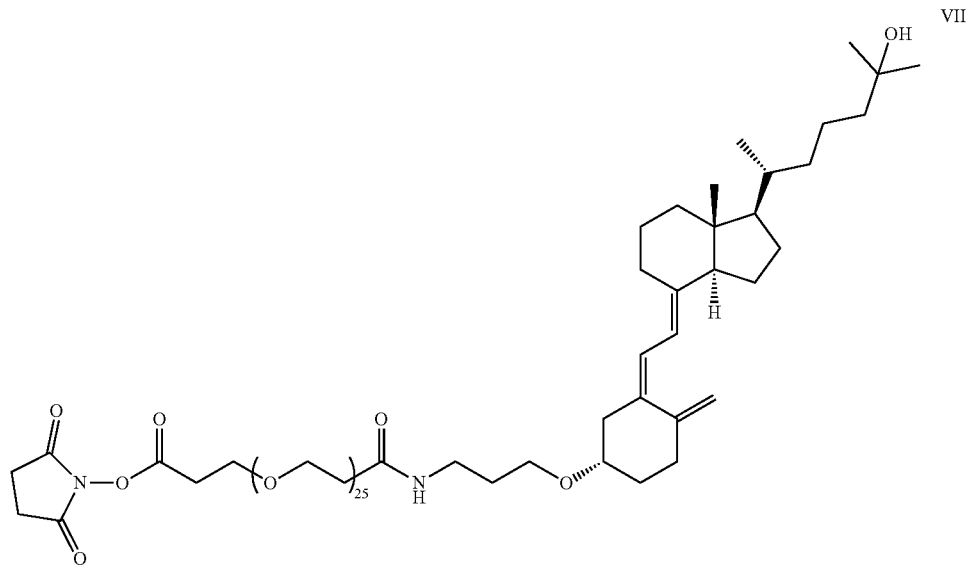

One skilled in the art will recognize that a compound of formula Vd can be used either as a free base or as a suitable salt form. Suitable salt forms include, but are not limited to TFA, HCl, HBr, MsOH, TfOH and AcOH.

In certain embodiments, a base such as triethylamine or diisopropylethylamine is used to promote coupling of the NHS-ester of formula VIIa with the amine of formula Va. One skilled in the art will recognize that bases other than triethylamine or diisopropylethylamine may be used.

NHS can be coupled with a carboxylic acid of formula VIIb in the presence of a suitable coupling reagent to form an active ester of formula VII. Suitable coupling reagents include, but are not limited to 2-chloromethylpyridinium iodide, BOP, PyBOP, HBTU, HATU, DCC, EDCI, TBTU, and T3P.

In some embodiments, an active ester of formula VII is formed from a carboxylic acid of formula VIIb using a combination of NHS and a coupling reagent.

In some embodiments, an active ester of formula VII is formed from a carboxylic acid of formula VIIb using a single reagent that produces a leaving group and also effects a coupling reaction. Such reagents include, but are not limited to, N,N'-disuccinimidyl carbonate. In some embodiments, the single reagent is used alone. In other embodiments the reagent is used with an acyl transfer catalyst. Such acyl transfer catalysts include, but are not limited to DMAP and pyridine. One skilled in the art will recognize that additional acyl transfer catalysts may be used.

One skilled in the art will recognize that there are other methods to conjugate a linker and scaffold to the C3 or C25 position of vitamin D derivatives and analogues. For example, the C3 hydroxy group may be acylated by various groups as practiced by N. Kobayashi, K. Ueda, J. Kitahori, and K. Shimada, *Steroids*, 57, 488-493 (1992); J. G. Haddad, et al., *Biochemistry*, 31, 7174-7181 (1992); A. Kutner, R. P. Link, H. K. Schnoes, H. F. DeLuca, *Bioorg. Chem.*, 14, 134-147 (1986); and R. Ray, S. A. Holick, N. Hanafin, and M. F. Holick, *Biochemistry*, 25, 4729-4733 (1986). The foregoing references are incorporated by reference in their entirety. One skilled in the art will recognize that these chemistries could be modified to synthesize compounds of the formula I:

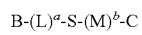

$$B-(L)^a-S-(M)^b-C \qquad \qquad I$$

wherein B, S, C, $(L)^a$, and $(M)^b$ are defined as above.

If desired, therapeutic compound carrier conjugates having different molecular weights can be isolated using gel filtration chromatography and/or ion exchange chromatography. Gel filtration chromatography may be used to fractionate different therapeutic compound carrier conjugates (e.g., 1-mer, 2-mer, 3-mer, and so forth, wherein "1-mer" indicates one targeting group molecule per therapeutic compound, "2-mer" indicates two targeting groups attached to therapeutic compound, and so on) on the basis of their differing molecular weights (where the difference corresponds essentially to the average molecular weight of the targeting group).

Gel filtration columns suitable for carrying out this type of separation include Superdex and Sephadex columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, and (iii) sodium dodecyl sulfate polyacrylamide gel electrophoresis (SDS PAGE).

Separation of therapeutic compound carrier conjugates can also be carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose ion exchange column available from Amersham Biosciences. The resulting purified compositions are preferably substantially free of the non-targeting group-conjugated therapeutic compound. In addition, the compositions preferably are substantially free of all other non-covalently attached targeting groups.

As described herein, the carriers of the invention may be non-hormonal 25-hydroxy vitamin D or analogs thereof having a coupling group on the 3' carbon. "25-hydroxy vitamin D analogs" as used herein includes both naturally-occurring vitamin D metabolite forms as well as other chemically-modified forms. The carriers of the invention do not include an active (i.e. hormonal) form of vitamin D (typically having a hydroxyl group at the 1 carbon). These compounds are based on the vitamin D structure and retain partial function of vitamin D (i.e. they interact with DBP), albeit at varying affinities. The following list exemplifies vitamin D analog forms known in the art. They may, however, be hormonal or have the C1 hydroxyl group. They are presented here solely for their chemical properties as vitamin D analogs, not for their functional hormonal properties: OCT, a chemically synthesized version of 1,25(OH)$_2$ D$_3$ with an oxygen atom at the 22 position in the side chain (Abe et. al., *FEBS Lett.* 226:58-62 (1987)); Gemini vitamin D analog, 1α,25-dihydroxy-20R-21(3-hydroxy-3-deuteromethyl-4,4,4-trideuterobutyl)-23-yne-26,27-hexafluoro-cholecalciferol (BXL0124) (So et al., *Mol Pharmacol.* 79(3): 360-7 (2011)); Paricalcitol, a vitamin D$_2$ derived sterol lacking the carbon-19 methylene group found in all natural vitamin D metabolites (Slatopolsky et al., *Am J. Kidney Dis.* 26: 852 (1995)); Doxercalciferol (la-hydroxyvitamin D$_2$), like alfacalcidol (1α-hydroxyvitamin D$_3$), is a prodrug which is hydroxylated in the liver to 1α,25(OH)$_2$D$_2$, however, unlike alfacalcidol, doxercalciferol is also 24-hydroxylated to produce 1α,24(S)—(OH)$_2$D$_2$ (Knutson et al., *Biochem Pharmacol* 53: 829 (1997)); Dihydrotachysterol$_2$ (DHT$_2$), hydroxylated in vivo to 25(OH)DHT$_2$, 1,25(OH)$_2$DHT$_2$ (McIntyre et al., *Kidney Int.* 55: 500 (1999)), ED-71, and eldecalcitol. See also Erben and Musculoskel, Neuron Interact. 2(1):59-69 (2001) and Steddon et al. *Nephrol. Dial. Transplant.* 16 (10): 1965-1967 (2001). The foregoing references are incorporated by reference in their entirety.

In another embodiment, the carrier further comprises a pharmaceutically acceptable scaffold moiety covalently attached to the targeting group and the therapeutic compound. The scaffold moiety of the carriers of the invention does not necessarily participate in but may contribute to the function or improve the pharmacokinetic properties of the therapeutic compound. The scaffolds of the invention do not substantially interfere with the binding of the targeting group to DBP. Likewise, the scaffolds of the invention do not substantially interfere with structure or function of the therapeutic compound. The length of the scaffold moiety is dependent upon the character of the targeting group and the therapeutic compound. One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977), incorporated herein by reference). Other scaffolds contemplated by the invention include peptide linkers, protein linkers such as human serum albumin or immunoglobulin family proteins or fragments thereof, nucleic acid linkers, small carbon chain linkers, carbon linkers with oxygen or nitrogen interspersed, or combinations thereof. In preferred embodiments, the linkers are non-releasable or stable.

PTH is a therapeutic peptide. The term "peptide," used interchangeably herein with the term "protein," is meant to include a string of amino acids. The amino acids in the peptides of the invention may be naturally-occurring or non-naturally-occurring. The peptides of the invention may be synthesized chemically or biologically, and can include cysteine-rich peptides, circular peptides, stapled peptides, peptides that include D- or L-amino acids and mixtures thereof, peptidomimetics, peptide-nucleic acids (PNAs), and combinations thereof. Also contemplated within the scope of embodiments described herein are therapeutic peptides that are branched or cyclic, with or without branching. Cyclic, branched and branched circular peptides result from post-translational natural processes and are also made by suitable synthetic methods. In some embodiments, any peptide product described herein comprises a peptide analog described above that is then covalently attached to an alkyl-glycoside surfactant moiety.

Other embodiments include therapeutic peptide chains that are comprised of natural and unnatural amino acids or analogs of natural amino acids. As used herein, peptide and/or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like.

Additional embodiments include therapeutic peptide chains having modified amino acids. Examples include acylated amino acids at the ε-position of Lysine, amino acids with fatty acids such as octanoic, decanoic, dodecanoic, tetradecanoic, hexadecanoic, octadecanoic, 3-phenylpropanoic acids and the like, or with saturated or unsaturated alkyl chains. (Zhang, L. and Bulaj, G. (2012) *Curr Med Chem* 19: 1602-1618, incorporated herein by reference in its entirety).

The invention further contemplates therapeutic peptide chains comprising natural and unnatural amino acids or analogs of natural amino acids. In some embodiments, peptide or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like. Examples of Tyr analogs include 2,4-dimethyl-tyrosine (Dmt), 2,4-diethyl-tyrosine, O-4-allyl-tyrosine, 4-propyl-tyrosine, Ca-methyl-tyrosine and the like. Examples of lysine analogs include ornithine (Orn), homo-lysine, Ca-methyl-lysine (CMeLys), and the like. Examples of phenylalanine analogs include, but are not limited to, meta-substituted phenylalanines, wherein the substituent comprises a methoxy group, a C1-C20 alkyl group, for example a methyl group, an allyl group, an acetyl group, or the like. Specific examples include, but are not limited to, 2,4,6-trimethyl-L-phenylalanine (Tmp), O-methyl-tyrosine, 3-(2-naphthyl)alanine (Nal(2)), 3-(1-naphthyl)alanine (Nal(1)), 3-methyl-phenylalanine, 1,2,3,4-tetrahydroisoquinoline-3-carboxylic acid (Tic), fluorinated phenylalanines, isopropyl-phenylalanine, p-azido-phenylalanine, p-acyl-phenylalanine, p-benzoyl-phenylalanine, p-iodo-phenylalanine, p-bromophenylalanine, p-amino-phenylalanine, and isopropyl-phenylalanine, and the like.

Also contemplated within the scope of embodiments are therapeutic peptide chains containing nonstandard or unnatural amino acids known to the art, for example, C-alpha-disubstituted amino acids such as Aib, Ca-diethylglycine (Deg), aminocyclopentane-1-carboxylic acid (Ac4c), aminocyclopentane-1-carboxylic acid (Ac5c), and the like. Such amino acids frequently lead to a restrained structure, often biased toward an alpha helical structure (Kaul, R. and Balaram, P. (1999) Bioorg Med Chem 7: 105-117, incorporated herein by reference in its entirety). Additional examples of such unnatural amino acids useful in analog design are homo-arginine (Har) and the like. Substitution of reduced amide bonds in certain instances leads to improved protection from enzymatic destruction or alters receptor binding. By way of example, incorporation of a Tic-Phe dipeptide unit with a reduced amide bond between the residues (designated as Tic-F[CH2-NH]^-Phe) reduces enzymatic degradation.

In some embodiments, modifications at the amino or carboxyl terminus may optionally be introduced into the present peptides or proteins (Nestor, J. J., Jr. (2009) Current Medicinal Chemistry 16: 4399-4418). For example, the present peptides or proteins can be truncated or acylated on the N-terminus (Gourlet, P., et al. (1998) Eur J Pharmacol 354: 105-1 1 1, Gozes, I. and Furman, S. (2003) Curr Pharm Des 9: 483-494), the contents of which is incorporated herein by reference in their entirety). Other modifications to the N-terminus of peptides or proteins, such as deletions or incorporation of D-amino acids such as D-Phe result in potent and long acting agonists or antagonists when substituted with the modifications described herein such as long chain alkyl glycosides.

Thus, the invention provides therapeutic compound analogs wherein the native therapeutic compound is modified by acetylation, acylation, PEGylation, ADP-ribosylation, amidation, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, (Nestor, J. J., Jr. (2007) Comprehensive Medicinal Chemistry II 2: 573-601, Nestor, J. J., Jr. (2009) Current Medicinal Chemistry 16: 4399-4418, Uy, R. and Wold, F. (1977) Science 198:890-6, Seifter, S. and Englard, S. (1990) Methods Enzymol 182: 626-646, Rattan, S. I., et al. (1992) Ann NY Acad Sci 663: 48-62). The foregoing references are incorporated by reference in their entirety.

Glycosylated therapeutic peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the therapeutic peptide polymer conjugates may be conjugated in vitro. The glycosylation may occur before deprotection. Preparation of amino acid glycosides is described in U.S. Pat. No. 5,767,254, WO 2005/097158, and Doores, K., et al., Chem. Commun., 1401-1403, 2006, which are incorporated herein by reference in their entirety. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated therapeutic peptide conjugate is made by stepwise solid phase peptide synthesis involving contacting a growing peptide chain with protected amino acids in a stepwise manner, wherein at least one of the protected amino acids is glycosylated, followed by water-soluble polymer conjugation. Such compositions may have a purity of at least 95%, at least 97%, or at least 98%, of a single species of the glycosylated and conjugated therapeutic peptide.

Monosaccharides that may be introduced at one or more amino acid residues of the therapeutic peptides defined and/or disclosed herein include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetylneuraminic acid, fucose, N-Acetylgalactosamine, and N-Acetylglucosamine, as well as others. Glycosides, such as mono-, di-, and trisaccharides for use in modifying a therapeutic peptide, one or more amino acid residues of the therapeutic peptides defined and/or disclosed herein include sucrose, lactose, maltose, trehalose, melibiose, and cellobiose, among others. Trisaccharides include acarbose, raffinose, and melezitose.

In further embodiments of the invention, the therapeutic compounds defined and/or disclosed herein may be chemically coupled to biotin. The biotin/therapeutic compound can then bind to avidin.

The presence or concentration of PTH may be measured using antibodies. The term antibody is meant to include monoclonal antibodies, polyclonal antibodies, antibody fragments (e.g., Fab fragments), single chain antibodies, bi- or multi-specific antibodies, Llama antibodies, nano-bodies, diabodies, affibodies, Fv, Fab, F(ab')2, Fab', scFv, scFv-Fc, and the like. Also included in the term are antibody-fusion proteins, such as Ig chimeras.

Antibodies that bind specifically to an antigen have a high affinity for that antigen. Antibody affinities may be measured by a dissociation constant (Kd). In certain embodiments, an antibody provided herein has a dissociation constant (Kd) of equal to or less than about 100 nM, 10 nM, 1 nM, 0.1 nM, 0.01 nM, or 0.001 nM (e.g. $10^{-7}$ M or less, from $10^{-7}$ M to $10^{-13}$ M, from $10^{-8}$ M to $10^{-13}$ M or from $10^{-9}$ M to $10^{-13}$ M).

Some aspects of the assembly of carriers utilizes chemical methods that are well-known in the art. For example, Vitamin E-PEG is manufactured by Eastman Chemical, Biotin-PEG is manufactured by many PEG manufacturers such as Enzon, Nektar and NOF Corporation. Methods of producing PEG molecules with some vitamins and other therapeutic compounds linked to them follow these and other chemical methods known in the art. The attachment of PEG to an oligonucleotide or related molecule occurs, for example, as the PEG2-N-hydroxysuccinimide ester coupled to the oligonucleotide through the 5' amine moiety. Several coupling methods are contemplated and include, for example, NHS coupling to amine groups such as a lysine residue on a peptide, maleimide coupling to sulfhydryl group such as on a cysteine residue, iodoacetyl coupling to a sulfhydryl group, pyridyldithiol coupling to a sulfhydryl group, hydrazide for coupling to a carbohydrate group, aldehyde for coupling to the N-terminus, or tetrafluorophenyl ester coupling that is known to react with primary or secondary amines. Other possible chemical coupling methods are known to those skilled in the art and can be substituted. By way of example, conjugation using the coupling groups of the invention may be carried out using the compositions and methods described in Int'l Pub. No. WO93/012145. See also U.S. Pat. No. 7,803,777. The foregoing are incorporated by reference herein in their entirety.

Exemplary drug formulations of the invention include aqueous solutions, organic solutions, powder formulations, solid formulations and a mixed phase formulations.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts retain the desired biological activity of the therapeutic composition without toxic side effects. Examples of such salts are (a) acid addition salts formed with inorganic acids, for example, hydrochloric acid, hydrobromic acid, sulfuric acid, phosphoric acid, nitric acid and the like/and salts formed with organic acids such as, for example, acetic acid, trifluoroacetic acid, tartaric acid, succinic acid, maleic acid, fumaric acid, gluconic acid, citric acid, malic acid, ascorbic acid, benzoic acid, tanic acid, pamoic acid, alginic acid, polyglutamic acid, naphthalenesulfonic acid, naphthalene disulfonic acid, polygalacturonic acid and the like; (b) base addition salts or complexes formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethlenediamine; or (c) combinations of (a) and (b), e.g. a zinc tannate salt and the like.

The pharmaceutical compositions of this invention may be administered by subcutaneous, transdermal, oral, parenteral, inhalation, ocular, topical, rectal, nasal, buccal (including sublingual), vaginal, or implanted reservoir modes. The pharmaceutical compositions of this invention may contain any conventional, non-toxic, pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional, and intracranial injection or infusion techniques.

Also contemplated, in some embodiments, are pharmaceutical compositions comprising as an active ingredient, therapeutic compounds described herein, or pharmaceutically acceptable salt thereof, in a mixture with a pharmaceutically acceptable, non-toxic component. As mentioned above, such compositions may be prepared for parenteral administration, particularly in the form of liquid solutions or suspensions; for oral or buccal administration, particularly in the form of tablets or capsules; for intranasal administration, particularly in the form of powders, nasal drops, evaporating solutions or aerosols; for inhalation, particularly in the form of liquid solutions or dry powders with excipients, defined broadly; for transdermal administration, particularly in the form of a skin patch or microneedle patch; and for rectal or vaginal administration, particularly in the form of a suppository.

The compositions may conveniently be administered in unit dosage form and may be prepared by any of the methods well-known in the pharmaceutical art, for example, as described in Remington's Pharmaceutical Sciences, 17th ed., Mack Publishing Co., Easton, PA (1985), incorporated herein by reference in its entirety. Formulations for parenteral administration may contain as excipients sterile water or saline alkylene glycols such as propylene glycol, polyalkylene glycols such as polyethylene glycol, saccharides, oils of vegetable origin, hydrogenated napthalenes, serum albumin or other nanoparticles (as used in Abraxane™, American Pharmaceutical Partners, Inc. Schaumburg, IL), and the like. For oral administration, the formulation can be enhanced by the addition of bile salts or acylcarnitines. Formulations for nasal administration may be solid or solutions in evaporating solvents such as hydrofluorocarbons, and may contain excipients for stabilization, for example, saccharides, surfactants, submicron anhydrous alpha-lactose or dextran, or may be aqueous or oily solutions for use in the form of nasal drops or metered spray. For buccal administration, typical excipients include sugars, calcium stearate, magnesium stearate, pregelatinated starch, and the like.

Delivery of modified therapeutic compounds described herein to a subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, polymeric hydrogels, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

In certain embodiments for transdermal administration, delivery across the barrier of the skin would be enhanced using electrodes (e.g. iontophoresis), electroporation, or the application of short, high-voltage electrical pulses to the skin, radiofrequencies, ultrasound (e.g. sonophoresis), microprojections (e.g. microneedles), jet injectors, thermal ablation, magnetophoresis, lasers, velocity, or photomechanical waves. The drug can be included in single-layer drug-in-adhesive, multi-layer drug-in-adhesive, reservoir, matrix, or vapor style patches, or could utilize patchless technology. Delivery across the barrier of the skin could also be enhanced using encapsulation, a skin lipid fluidizer, or a hollow or solid microstructured transdermal system (MTS, such as that manufactured by 3M), jet injectors. Additives to the formulation to aid in the passage of therapeutic compounds through the skin include prodrugs, chemicals, surfactants, cell penetrating peptides, permeation enhancers, encapsulation technologies, enzymes, enzyme inhibitors, gels, nanoparticles and peptide or protein chaperones.

One form of controlled-release formulation contains the therapeutic compound or its salt dispersed or encapsulated in a slowly degrading, non-toxic, non-antigenic polymer such as copoly(lactic/glycolic) acid, as described in the pioneering work of Kent et al., U.S. Pat. No. 4,675,189, incorporated by reference herein. The compounds, or their salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, J R Robinson ed., Marcel Dekker Inc., New York, 1978; and Controlled Release of Biologically Active Agents, R W Baker, John Wiley & Sons, New York, 1987. The foregoing are incorporated by reference in their entirety.

An additional form of controlled-release formulation comprises a solution of biodegradable polymer, such as copoly(lactic/glycolic acid) or block copolymers of lactic acid and PEG, is a bioacceptable solvent, which is injected subcutaneously or intramuscularly to achieve a depot formulation. Mixing of the therapeutic compounds described herein with such a polymeric formulation is suitable to achieve very long duration of action formulations.

When formulated for nasal administration, the absorption across the nasal mucous membrane may be further enhanced by surfactants, such as, for example, glycocholic acid, cholic acid, taurocholic acid, ethocholic acid, deoxycholic acid, chenodeoxycholic acid, dehdryocholic acid, glycodeoxycholic acid, cycledextrins and the like in an amount in the range of between about 0.1 and 15 weight percent, between about 0.5 and 4 weight percent, or about 2 weight percent. An additional class of absorption enhancers reported to exhibit greater efficacy with decreased irritation is the class of alkyl maltosides, such as tetradecylmaltoside (Arnold, J J et al., 2004, J Pharm Sci 93: 2205-13; Ahsan, F et al., 2001, Pharm Res 18:1742-46) and references therein, all of which are hereby incorporated by reference.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topical transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When formulated for delivery by inhalation, a number of formulations offer advantages. Adsorption of the therapeutic compound to readily dispersed solids such as diketopiperazines (for example, Technosphere particles (Pfutzner, A and Forst, T, 2005, *Expert Opin Drug Deliv* 2:1097-1106) or similar structures gives a formulation that results in rapid initial uptake of the therapeutic compound. Lyophilized powders, especially glassy particles, containing the therapeutic compound and an excipient are useful for delivery to the lung with good bioavailability, for example, see Exubera® (inhaled insulin, Pfizer, Inc. and Aventis Pharmaceuticals Inc.) and Afrezza® (inhaled insulin, Mannkind, Corp.).

Dosage levels of between about 0.1 and about 300 µg/kg body weight per day, preferably 0.5 and about 50 µg/kg body weight per day of the active ingredient compound are useful in the prevention and treatment of disease. Such administration can be used as a chronic or acute therapy. The amount of drug that may be combined with the carrier to produce a single dosage form will vary depending upon the host treated and the particular mode of administration. A typical preparation will contain from about 0.010% to about 1% active compound (w/w). Preferably, such preparations contain from about 0.02% to about 1% active compound (w/w).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, rate of excretion, drug combination, the severity and course of an infection, the patient's disposition to the infection and the judgment of the treating physician.

The carrier-drug conjugates described herein provide advantages to drug manufacturers and patients over unmodified drugs. Specifically, the carrier-drug conjugate or formulation will be a more potent, longer lasting, and require smaller and less frequent dosing. This translates into lowered healthcare costs and more convenient drug administration schedules for patients. The carrier-drug conjugates can also provide subcutaneous or transdermal routes of administration as alternatives to intravenous injection. These routes can be self-administered by patients and thus improve patient compliance.

In yet another aspect of the invention, the levels of DBP can be increased as part of the carrier-drug therapy. It has been reported that estrogen can increase DBP levels (Speeckaert et al., *Clinica Chimica Acta* 371:33). It is contemplated here that levels of DBP can be increased by administration of estrogen for more effective delivery of carrier-drug conjugates.

In yet another aspect of the invention, it is contemplated that the carrier can be used to deliver drugs transdermally. Since DBP normally transports UV activated vitamin D at locations close to the surface of the skin, the use of a transdermal delivery system with the carrier becomes feasible.

In order that the invention described herein may be more fully understood, the following examples are set forth. It should be understood that these examples are for illustrative purposes only and are not to be construed as limiting this invention in any manner. In particular, the compositions and methods disclosed herein function with all non-hormonal forms of vitamin D, including homologs, analogs, and metabolites thereof. This includes vitamin D as used in the examples below.

EXAMPLES

Example 1: Preparation of PTH Coupled to Non-Hormonal Vitamin D at the C3 Position A PTH(1-34) with a C-terminal cysteine residue and a discrete 1.6 kDa PEG was synthesized using a maleimide group resulting in a thioether bond (PTH-C-PEG$_{1.6K}$-(3)-VitD). See WO2016/065042, incorporated by reference herein in its entirety.

Modified PTH(1-34) compounds were made with the following structures (SEQ ID NOS 9, 6, and 7, respectively):

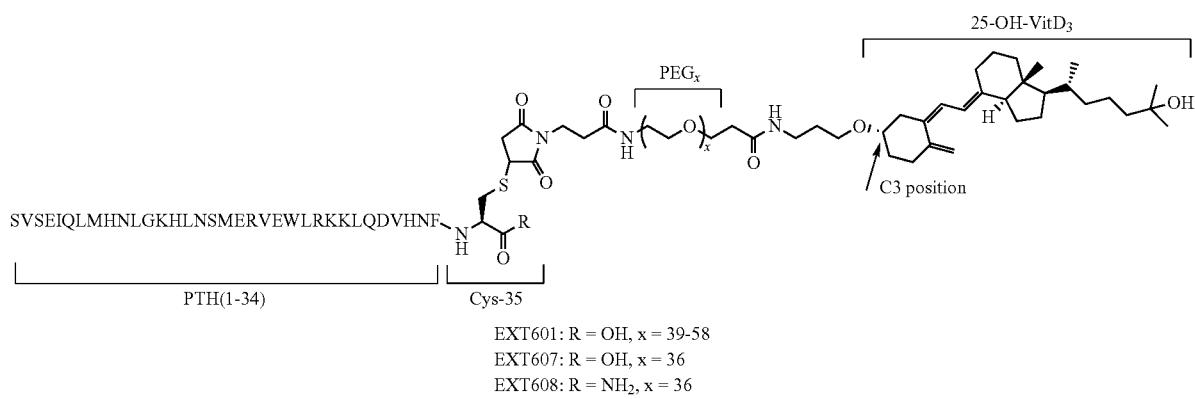

EXT601: R = OH, x = 39-58
EXT607: R = OH, x = 36
EXT608: R = NH$_2$, x = 36

EXT601 was made as described in WO2016/065042, incorporated herein by reference in its entirety. EXT607 was made using the same methods described below for EXT608 except that R on EXT607 is OH whereas R on EXT608 is NH$_2$. R=NH$_2$ is advantageous over R=OH in preventing impurity formation during solid phase synthesis of peptides where the C-terminal amino acid is cysteine.

Figure 1:
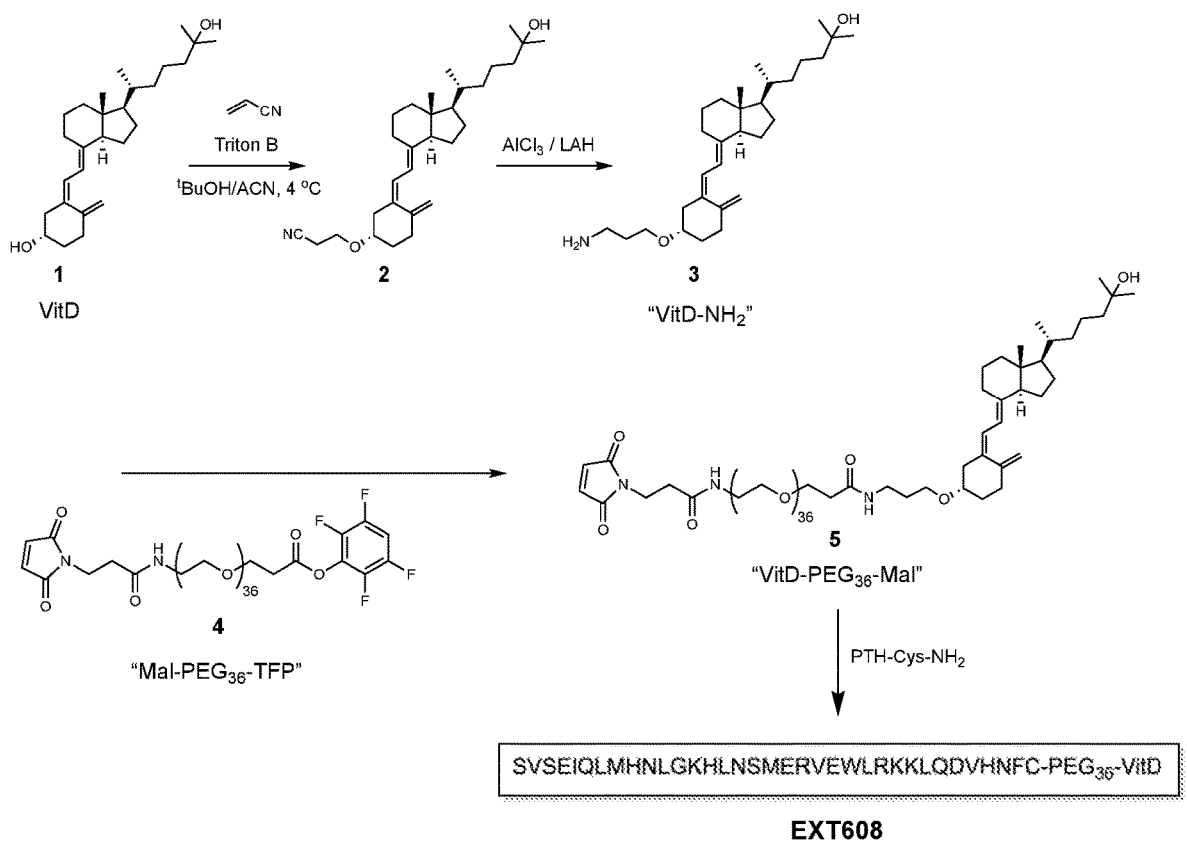
FIG. 1: Method for synthesis of EXT608. Figure discloses SEQ ID NO: 8.

The general method of EXT608 synthesis is shown in FIG. 1. The conversion of 25OH-vitamin D (25-hydroxycholecalciferol, compound 1) into "VitD-NH$_2$" (compound 3) occurred in two steps via functionalization of the 3'-hydroxyl group of vitamin D with acrylonitrile followed by reduction with lithium aluminum hydride (Ray, et al. 1991). The resulting amine (3) is then coupled to the tetrafluorophenyl (TFP) ester of a heterobifunctional TFP-PEG$_{36}$-maleimide linker (4) obtained from Quanta BioDesign, Ltd. (Plain City, OH, USA, CAT. #10555) resulting in VitD-PEG-maleimide (5). The PTH(1-34)-cys-NH$_2$ peptide was synthesized by solid phase peptide techniques. It was then fully deprotected and removed from the resin to generate the crude PTH(1-34)-cys-NH$_2$ peptide. The crude peptide was purified by preparative HPLC and the purified PTH(1-34)-cys-NH$_2$ was isolated by lyophilization. The final synthetic step, conjugation of the purified peptide and VitD-PEG-maleimide, was performed in a solution phase reaction. The fully assembled EXT608 was then purified using preparative reverse phase HPLC to remove unreacted PTH(1-34)-cys-NH$_2$, VitD-PEG-maleimide, and other impurities. This allowed for final isolation of EXT608 when dried by lyophilization. The detailed steps are as follows:

Synthesis of VitD-PEG$_{36}$-maleimide (Compound 5), Method 1. VitD-NH$_2$ (Compound 3) was made in and described as "Compound Vd" in WO2016/065042, incorporated herein by reference in its entirety.

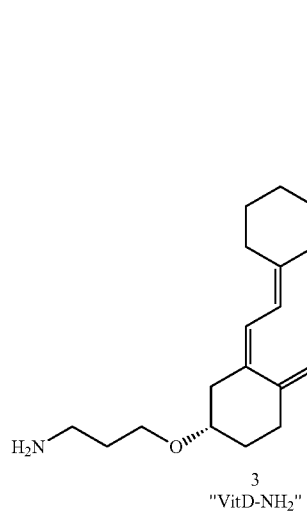

3
"VitD-NH₂"

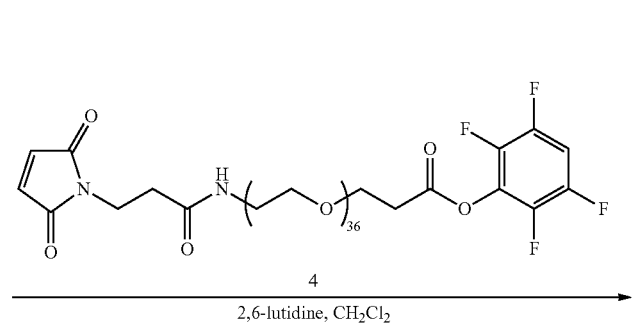

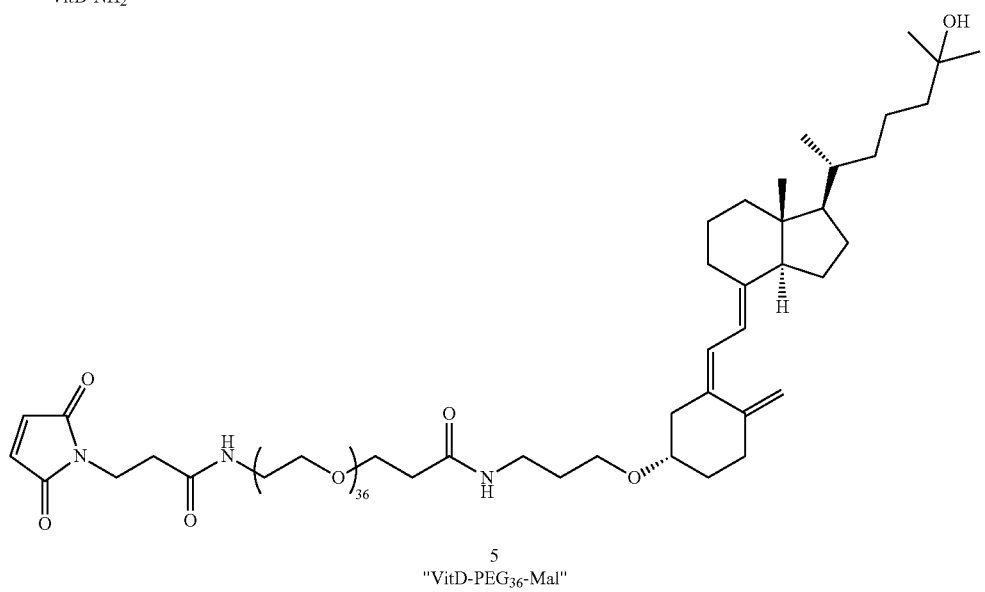

5
"VitD-PEG₃₆-Mal"

To a mixture of Compound 3 (1 eq) dissolved in anhydrous dichloromethane under nitrogen at 4° C. was added 2,6-lutidine (2.5 eq) dropwise and stirred for 15 min. Compound 4 (Quanta BioDesign, Plain City, OH USA, Cat. #10555, 0.8 eq) dissolved in 30 mL dichloromethane was added slowly to this mixture via syringe. The resultant reaction mixture was stirred at room temperature under inert atmosphere and monitored by thin layer chromatography (TLC). After 4 hr, the reaction mixture was diluted with dichloromethane, washed with 10% aqueous citric acid, saturated aqueous sodium bicarbonate, and brine. The organic layer was dried over anhydrous $Na_2SO_4$, filtered and concentrated at 30° C. to give crude product. The crude mixture was purified by silica gel Gold ISCO flash chromatography. The column was eluted with 1-10% MeOH/chloroform (1% ammonium hydroxide). Fractions containing the purified product were combined and evaporated under vacuo to yield compound 5 as a pale-yellow solid ($R_f$ 0.3 silica gel, 10% methanol in dichloromethane) at 62% yield and a purity of 68% by HPLC/TLC.

Synthesis of VitD-PEG₃₆-maleimide (Compound 5), Method 2. In efforts to improve the purity of Compound 5 (Mal-PEG₃₆-VitD) it was discovered that the VitD-PEG₃₆-maleimide produced by Method 1 contained impurities that were formed during lyophilization. While the exact structure of these impurities was not determined, NMR analyses indicated that the double bonds of maleimide and vitamin D were involved in the undesired reaction during lyophilization. Therefore, the crude reaction mixture of compounds 3 and 4 prepared by Method 1 was purified instead by preparative HPLC using a water/acetonitrile mobile phase. The pooled fractions were used directly in the conjugation reaction with PTH(1-34)-cys-NH₂. Since compound 5 was not isolated as a solid, quantitation of compound 5 was obtained by optical absorbance measurements using the extinction coefficient to calculate concentration. The purity of compound 5 using this method was 94.10%.

Peptide synthesis. PTH(1-34)-cys-NH₂ was manufactured using a Fmoc (9-Fluorenylmethoxycarbonyl) solid phase peptide synthesis (SPPS) strategy. Ramage resin (tricyclic amide linker) was used in the manufacturing process because it is particularly acid sensitive and is therefore well-suited for the preparation of fully protected peptide amides by Fmoc chemistry. With this resin, a C-terminal cysteine-amide (R=NH$_2$) was formed that is less prone to unwanted side reactions than the C-terminal cysteine-acid (R =OH). The peptide was detached from the resin with concomitant cleavage of the side chain protecting groups by treatment of the peptide resin with a strong acid, trifluoroacetic acid (TFA). Scavengers [1,2-ethanedithiol (EDT), triisopropylsilane (TIS), and water] were added to trap reactive cations during cleavage and to avoid alkylation of side chain functions, yielding a higher quality of crude peptide. Ammonium iodide (NH$_4$I) was added to the cleavage cocktail because the peptide sequence contains a thioether structure. Finally, ascorbic acid was used to neutralize the NH$_4$I. These reagents were used to assure complete reduction of methionine sulfoxide potentially present in the product. Following the cleavage operation, the crude peptide was precipitated using cooled isopropyl ether (IPE) and filtered using a fritted glass funnel. The resulting cake was washed with IPE and dried in a vacuum oven at room temperature.

Peptide Purification and Lyophilization: The crude product is purified by two-dimensional preparative HPLC on a reversed-phase column with an acetonitrile (ACN) gradient elution and UV detection at 230 nm. For the first preparative HPLC step, a phosphoric acid (H$_3$PO$_4$) buffer system is used as the mobile phase. A C8 reversed phase resin is the stationary phase. The individual collected fractions are analyzed by Ultra Performance Liquid Chromatography (UPLC, Waters Corporation, Milford, MA) and pooled according to the purity acceptance criteria. Fractions with purity≥90% are identified as main pool. The pooled main fractions are diluted with water to lower their ACN concentration and are further processed in the second preparative HPLC step. A trifluoracetic acid (TFA) buffer system is used for the second purification step by preparative HPLC. A C8 reversed phase resin is the stationary phase. The individual collected fractions are analyzed by UPLC and pooled according to the purity acceptance criteria. Fractions with purity≥95% are identified as the main pool. The main product pool from the TFA purification step was filtered through a 0.45 μm membrane filter and lyophilized.

EXT608 Conjugation Reaction to Produce the Carbonate Salt (Method A): The VitD-PEG-maleimide conjugation reagent (Compound 5) prepared using Method 1 was dissolved in dimethyl sulfoxide (DMSO) and diluted with a solution of Tris buffer containing ethylenediaminetetraacetic acid (EDTA). The lyophilized peptide from the above step was dissolved in a Tris buffer (pH 7.4). These solutions were mixed together and the reaction was monitored using analytical HPLC. The reaction was stopped with the addition of a 2% acetic acid solution and loaded onto a YMC C8 column equilibrated with 10 mM ammonium bicarbonate (NH$_4$HCO$_3$, pH 8) buffer in water. The product elution was achieved using a gradient of 10 mM NH$_4$HCO$_3$ buffer and acetonitrile and all fractions that met the establish criteria were collected and pooled together. The purified solution was filtered through a 0.45 μm membrane filtration system. Upon completion of the purification stage, the solution was lyophilized to obtain EXT608 as the carbonate salt. The final product was analyzed by UPLC and LC-MS and determined to have a purity of 80.05%. The major impurity (7.5%) had a molecular weight 18 mass units higher (M+18) than EXT608 and was hypothesized to be due to hydrolytic ring opening of the thiosuccinimide ring (formed from cysteine addition to maleimide). Thus, in some embodiments, performing the peptide/VitD-PEG-Mal coupling and purification at a lower pH prevents thiosuccinimide hydrolysis during the reaction, purification, and lyophilization (see sections below). Opening of the ring, however, does not change the activity of the compound.

EXT608 Conjugation Reaction to Produce the Acetate Salt (Method B): The VitD-PEG-maleimide conjugation reagent (Compound 5) was prepared using Method 2 and the resulting pooled HPLC purification fractions were added to PTH(1-34)-cys-amide dissolved in 0.5 M ammonium acetate buffer pH=6.0. The conjugated peptide solution is purified by preparative HPLC with a pH 5.5 NH$_4$OAc system on a reversed-phase column UV detection at 220 nm. After elution with an ACN gradient, the individual collected fractions are analyzed by UPLC and pooled according to the purity acceptance criterion (≥90%). The main pools are consolidated and diluted with purified water for lyophilization. The final product was analyzed by UPLC and determined to have a purity of 90.8% with undetectable levels of the M+18 impurity. Therefore, lowering reaction pH from 7.4 in Method A to 6.0 and the purification pH from 8.0 in Method A to 5.5 eliminated the major impurity hypothesized to result from thiosuccinimide hydrolysis.

Example 2: A Discrete PEG Linker is Advantageous Over a Polydisperse PEG Linker

It was important to use a discrete PEG chain length in order to provide uniformity for patient administration, maximize manufacturing yields, and increase the ability to monitor the vitamin D PTH conjugates and related impurities during the manufacturing and treatment processes using techniques such as UPLC, mass spectrometry, and LC-MS.

Analysis of EXT601 and EXT608 by UPLC. The following UPLC method was developed for the analysis of vitamin D modified PTH compounds. An ACQUITY UPLC Peptide CSH C18 column (2.1×150 mm, 1.7 μm, 130A; Waters Acquity, Milford, MA, Cat. No. 186006938) was used with a column temperature of 40° C., a flow rate of 0.4 ml/min, injection volumes of 3 μl, and a detection wavelength of 220 nm. Mobile Phase A consisted of 80% Water/20% ACN/0.10% TFA and Mobile Phase B consisted of 20% Water/80% ACN/0.085% TFA. The following gradient of Mobile Phase A (% A) and Mobile Phase B (% B) was used:

| Time (min) | % A | % B |
| --- | --- | --- |
| Initial | 70 | 30 |
| 15.0 | 70 | 30 |
| 25.0 | 58 | 42 |
| 30.0 | 50 | 50 |
| 36.0 | 20 | 80 |
| 40.0 | 20 | 80 |

Figure 2:
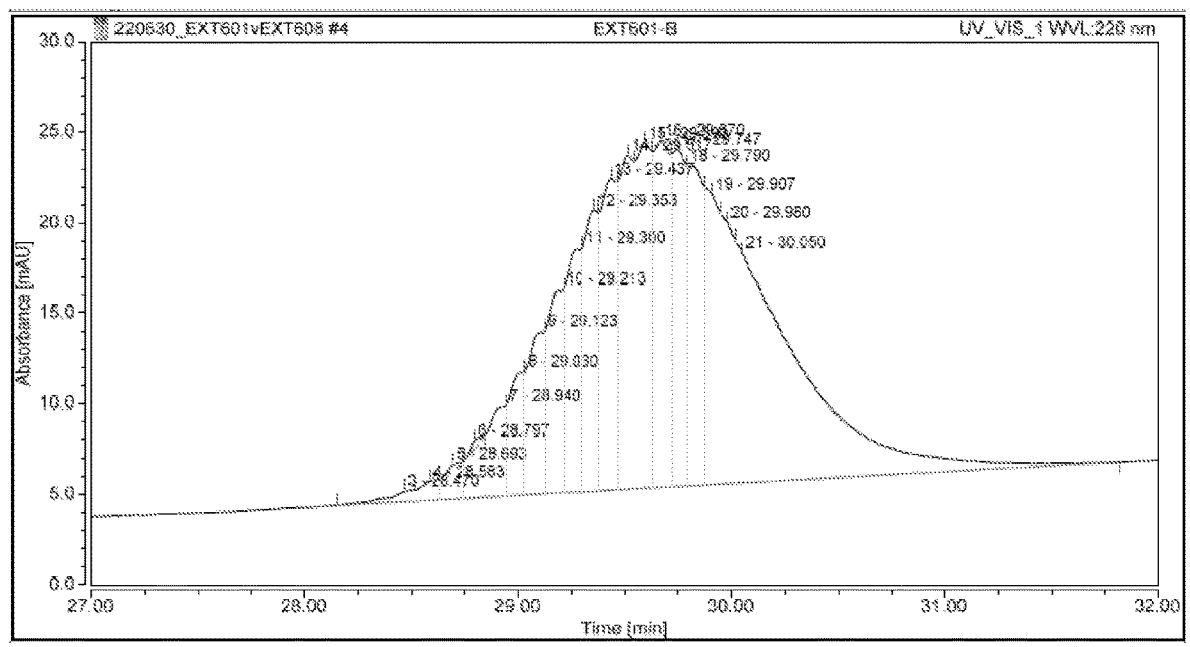
FIG. 2: UPLC analysis of EXT601.
Figure 3:
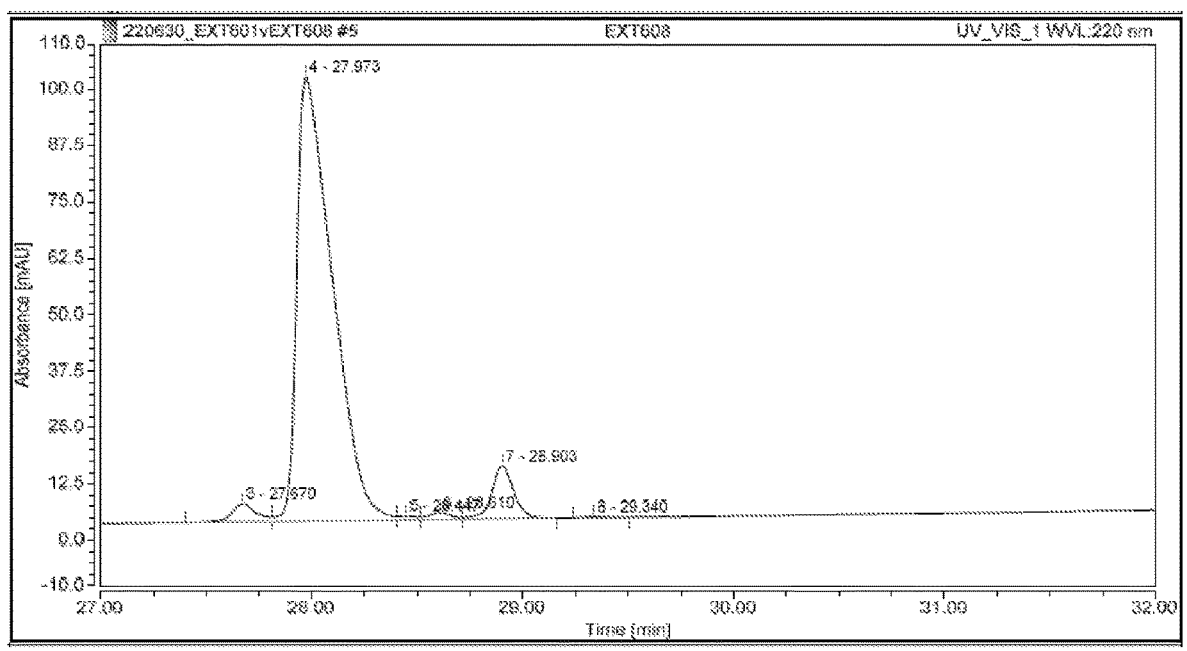
FIG. 3: UPLC analysis of EXT608.

The UPLC trace of EXT601 is shown in FIG. 2. The polydisperse length of the PEG linker resulted in a very broad UPLC peak with a width at baseline of approximately 3 minutes. Any impurities were obscured by the broad EXT601 peak and by the fact that any peptide- or vitamin D-related impurities would be present as multiple peaks for each PEG length variation. In contrast, the UPLC trace of EXT608 (FIG. 3), which contains a single length PEG linker (x=36), showed a narrow peak with a width at baseline of approximately 0.5 minutes. The impurities present were well-separated from the EXT608 peak. This facilitates further characterization, isolation, and identification of the impurities. Furthermore, a discreet yield of therapeutic VitD-PEG$_{36}$-PTH provides an important characteristic for more efficient purification, quantification, and monitoring of the molecule during manufacturing and treatment in patients.

Figure 4:
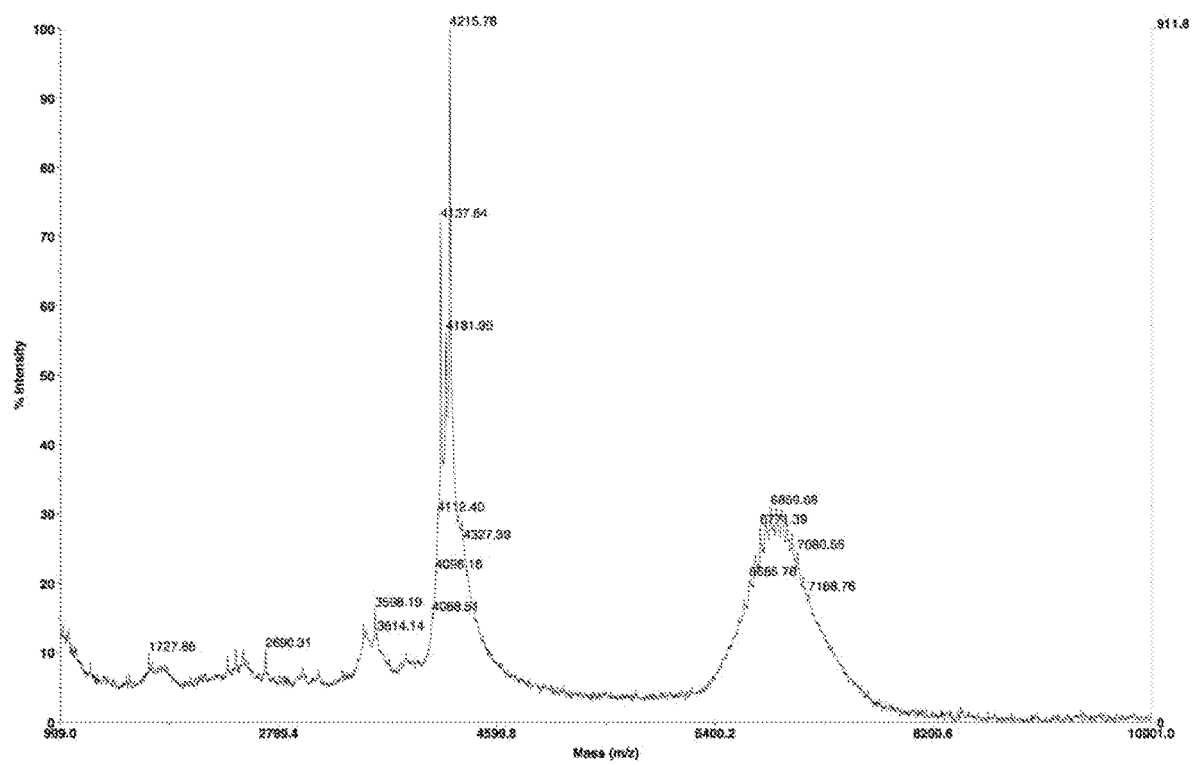
FIG. 4: MALDI-TOF mass spectrometric analysis of EXT601.
Figure 5:
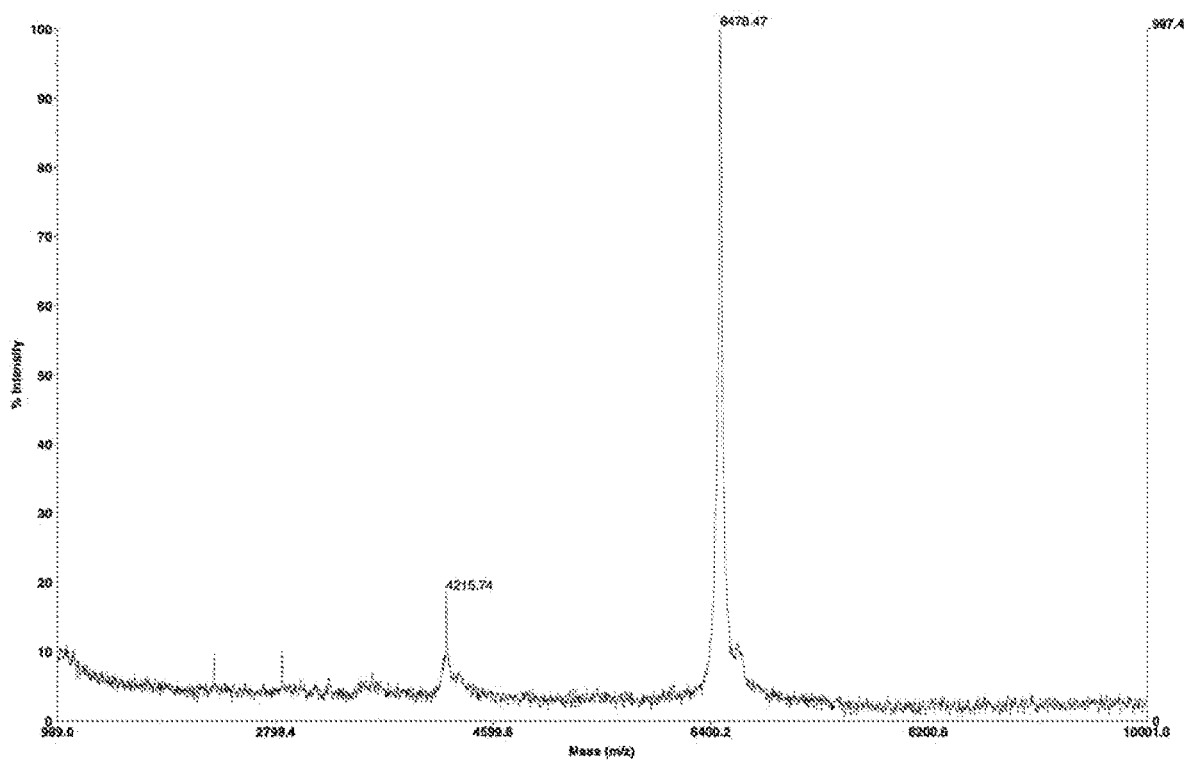
FIG. 5: MALDI-TOF mass spectrometric analysis of EXT608.

Analysis of EXT601 and EXT608 by MALDI-TOF Mass Spectrometry: EXT601 and EXT608 were analyzed by MALDI-TOF (matrix-assisted laser desorption/ionization-time of flight) mass spectrometry in the positive ion mode. The MALDI-TOF analysis of EXT601 is shown in FIG. 4. The polydisperse length of the PEG linker resulted in a very broad peak with a discernable signal above baseline between approximately 6400-7650 g/mol. This corresponded to $PEG_X$ linkers with x=34 to 62 repeating units. The average molecular weight was approximately 6880 g/mol, corresponding to a $PEG_{45}$ linker. The MALDI-TOF analysis of EXT608 is shown in FIG. 5. In contrast to EXT601, EXT608 had a single peak with a molecular weight of 6478 g/mol. For both compounds, the signals at approximately 4215 g/mol resulted from fragmentation of the intact parent compound upon ionization in the mass spectrometer (i.e., in-source fragmentation). Compared to EXT601, EXT608 had a higher signal/background ratio and a higher relative abundance compared to the in-source generated fragments.

Example 3: PTH(1-34), EXT601, EXT607, and EXT608 Activates the Parathyroid Hormone Receptor 1 (PTHR1) Equally The activity of EXT607 and EXT608 compared to PTH (1-34) on human parathyroid receptor 1 (PTHR1, also called PTH1R) was measured by a cell-based calcium flux assay in agonist mode using PathHunter® mammalian cell lines expressing Gq-coupled receptors (DiscoverX, Fremont, CA USA, now part of Eurofins Discovery, Catalog Number 86-0030P-2212AG). EXT607 and EXT608 were diluted to 100 µM in phosphate buffered saline. PTH(1-34) control article was provided by DiscoverX. Cells expressing human PTHR1 were treated with 10 concentrations of test article in duplicate at a highest concentration of 1 µM. Intracellular calcium release was measured on a FLIPR Tetra for 2 minutes following exposure using a calcium-sensitive dye loaded into the cells. Percent efficacy of activation was calculated as follows Percent efficacy=100%×(mean RFU of test sample–mean RFU of vehicle control)/(mean MAX RFU of control ligand–mean RFU of vehicle control)

Figure 6:
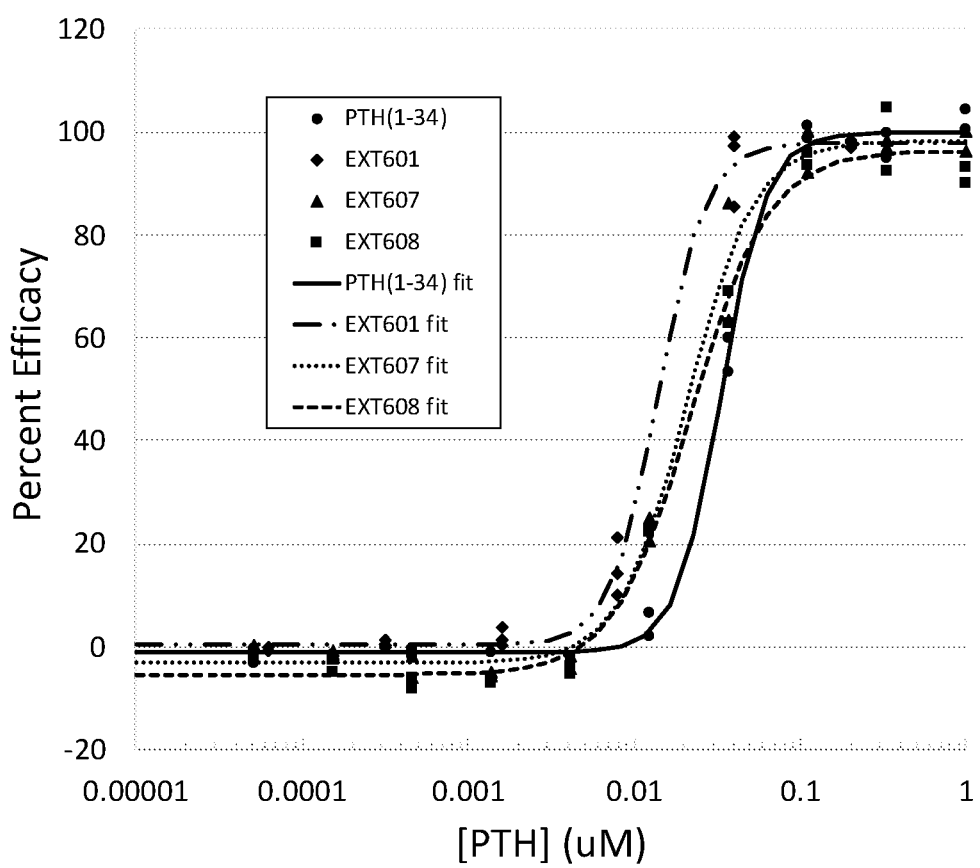
FIG. 6: Cell-based PTHR1 activity assay comparing PTH(1-34), EXT601, EXT607, and EXT608.

EC50 (half maximal effective concentration) values were determined from plots of percent efficacy vs concentration of agonist (FIG. 6). The EC50 values were 33 nM for PTH(1-34), 21 nM for EXT607, and 22 nM for EXT608. The EC50 value for EXT601 was 14 nM as determined in WO2016/065042, incorporated herein by reference in its entirety. The compounds were equipotent within the experimental error of the assay. Therefore, conjugation of the vitamin D moiety to PTH(1-34) does not interfere with PTHR1 activation. EXT601, EXT607, and EXT608 had approximately equal activity at the PTHR1.

Example 4: EXT607 and EXT608 Bind to the Vitamin D Binding Protein (DBP) with Equal Affinity EXT607 and EXT608 were biotinylated using the EZ-Link Sulfo-NHS Biotin No-Weigh kit (Thermo Fisher Scientific, Waltham, MA, Catalog No. PIA39256). One mmol of biotin was reacted with 1 mmol of conjugate for 1 hour at room temperature. Unbound biotin was separated from biotinylated conjugate with a PD-10 desalting column (GE Lifesciences/Cytiva, Marlborough, MA, Catalog No. 17085101). The biotinylation ratio was quantitated using the Pierce Biotin Quantitation Kit (Thermo Fisher Scientific, Waltham, MA, Catalog No. PI28005). DBP was purchased from Athens Research and Technology (Athens, GA, Catalog No. 16-16-070307).

Figure 7:
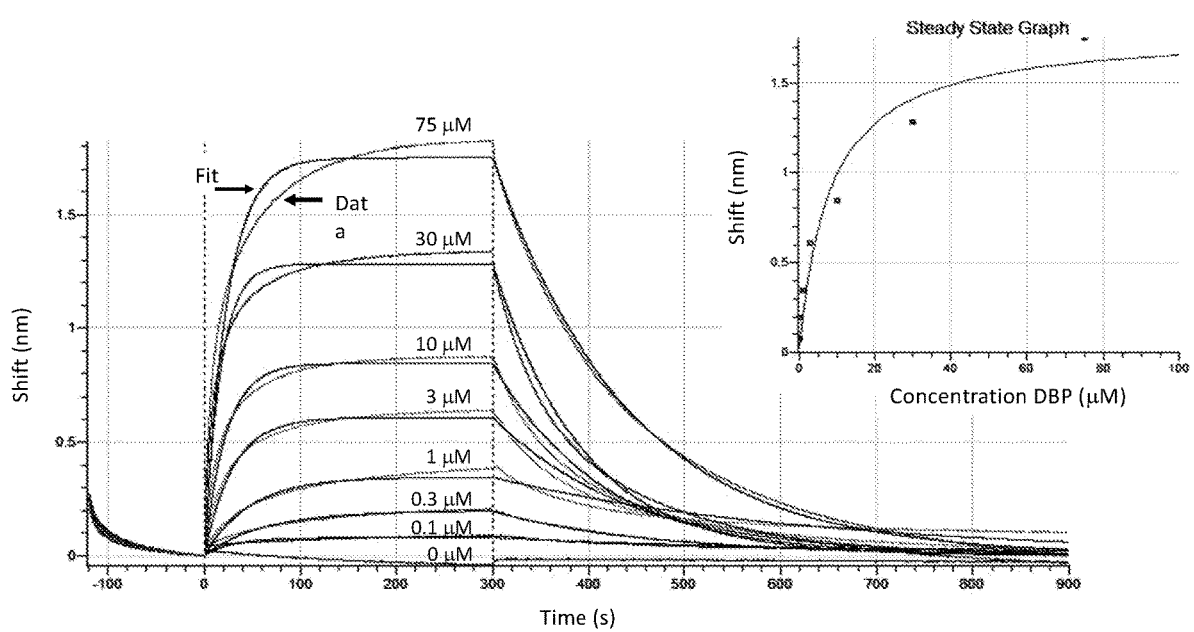
FIG. 7: Kinetic binding analysis of vitamin D binding protein (DBP) to immobilized EXT607 by bio-layer interferometry (BLI) as a function of DBP concentration (0-75 µM). For each concentration of DBP is shown both the binding association and disassociation data as well as the calculated fit generated using the ForteBio Octet Data Analysis Software. Inset: Plot of the steady state BLI shifts as a function of DBP concentration. A binding equilibrium constant ($K_D$) of 8.1 µM±2.5 µM was obtained from the calculated steady state curve fit.
Figure 8:
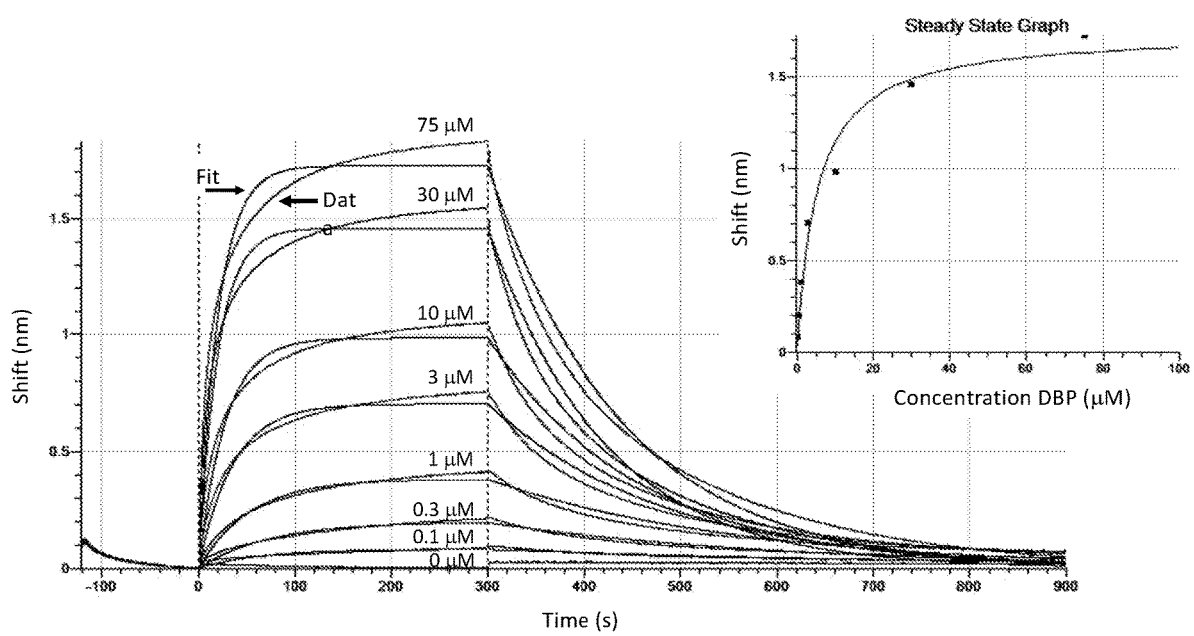
FIG. 8: Kinetic binding analysis of vitamin D binding protein (DBP) to immobilized EXT608 by bio-layer interferometry (BLI) as a function of DBP concentration (0-75 µM). For each concentration of DBP is shown both the binding association and disassociation data as well as the calculated fit generated using the ForteBio Octet Data Analysis Software. Inset: Plot of the steady state BLI shifts as a function of DBP concentration. A binding equilibrium constant ($K_D$) of 5.2 µM+1.1 µM was obtained from the calculated steady state curve fit.

Affinity measurements were collected on the Octet Red96 using prehydrated Dip and Read Streptavidin (SA) Biosensors (ForteBio, Fremont, CA, Catalog No. 18-5021). Reagents were diluted into phosphate buffered saline (PBS) with 0.02% Tween 20 in a black 96-well plate. Biotinylated EXT607 or EXT608 were prepared at a biotin concentration of 50 µg/mL and loaded onto the SA tips for 2 minutes. A buffer-only negative loading control was used to measure non-specific binding of DBP to the SA biosensors. A titration of DBP ranging from 0 to 75 µM was prepared. DBP was associated to the loaded tips for 5 minutes and dissociated with buffer solution for 10 minutes. Binding association and disassociation curves as well as steady-state curve fits were generated using the ForteBio Octet Data Analysis Software (FIGS. 7 and 8), and binding equilibrium constants (KD) were obtained from the steady state data. Both EXT607 and EXT608 had a maximum response of a 1.79 nm shift. The $K_D$ of EXT607 for DBP is 8.1 µM+2.5 µM. The $K_D$ of EXT608 is 5.2 µM+1.1 µM.

Example 5: PEG36 is the Optimum Chain Length

Optimization of PEG chain length is important for maximizing the solubility and PTHR1 receptor activity of the vitamin D-PTH conjugates.

EXT611 (PTH-cys-PEG12-VitD) and EXT606 (PTH-cys-PEG24-VitD) Synthesis: One molar equivalent of Mal-PEG12-NHS (Quanta BioDesign #10284) or Mal-PEG24-TFP (Quanta BioDesign #10554) was reacted with 1.1 equivalents of $VitD-NH_2$ (compound 3) in DMSO for 30 minutes at room temperature where NHS was an amine-reactive N-hydroxysuccinimide ester. The reaction was quenched by adding an equal volume of 0.1 M ammonium acetate pH=6.8. PTH(1-34)-cys-$NH_2$ (1.0 equivalents in water) was added along with 0.5 M MES pH=6.1 to a final concentration 50 mM, and the reaction was allowed to proceed for 30 minutes at room temperature. The reaction was purified by HPLC using an Xselect CSH Phenyl Hexyl column with mobile phases consisting of 0.1 M ammonium acetate pH=5 and acetonitrile. It was then lyophilized to yield the acetate salt form of the compounds. Alternately, compounds were purified using 0.1 M ammonium carbonate pH=8 as the aqueous component of the mobile phase to yield the carbonate salt form of the compounds.

EXT615 (PTH-PEG5 kDa-VitD), EXT616 (PTH-PEG10 kDa-VitD), and EXT617 (PTH-PEG20 kDa-VitD) Synthesis: One molar equivalent of Mal-PEG5 kDa-NHS (Nanosoft Biotechnology, Lewisville, NC, Catalog No. 2597-5000, "Mal-PEG5000-SCM"), Mal-PEG10 kDa-NHS (Nanosoft Biotechnology, Catalog No. 2597-10K, "Mal-PEG10K-SCM"), or Mal-PEG20 kDa-NHS (Advanced Bio-Chemicals, Lawrenceville, GA, Catalog No. HEPO405, "SC-PEG-MAL,20k") dissolved in DMF (5 kDa and 10 kDa) or MeCN (20 kDa) was reacted with 1.1 equivalents of $VitD-NH_2$ (Compound 5) in DMSO for 30 minutes at room temperature. The reaction was quenched by adding an equal volume of 0.1 M ammonium acetate pH=6.8. The Mal-PEG-VitD intermediates were purified by HPLC using an Xselect CSH Phenyl Hexyl column with mobile phases consisting of 0.1 M ammonium acetate pH=5 and acetonitrile, lyophilized, and dissolved in DMF (5 kDa) or MeCN(10 kDa and 20 kDa). PTH(1-34)-cys-NH$_2$ (1.0 equivalents in water) was added along with 0.5 M MES pH=6.1 to a final concentration 50 mM, and the reaction was allowed to proceed for 30 minutes at room temperature. The PTH-PEG-VitD products were purified by HPLC as above and lyophilized to yield either the acetate or carbonate salt forms of the compounds.

Figure 9:
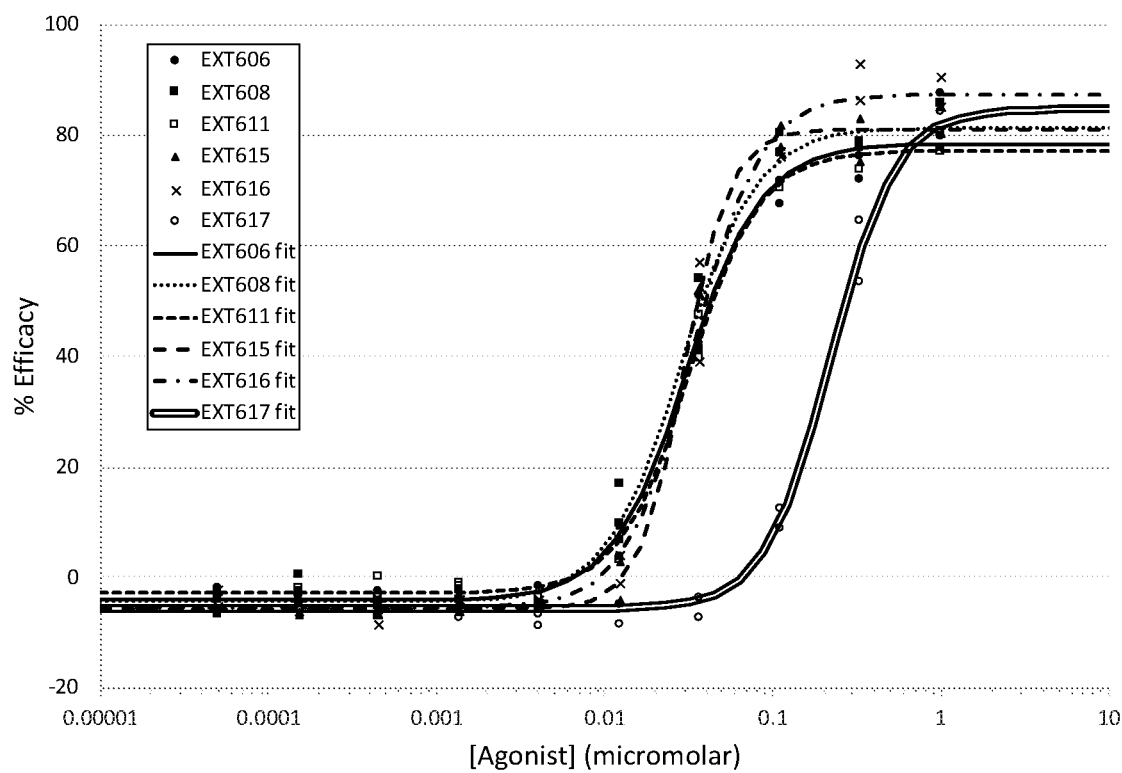
FIG. 9: Cell-based PTHR1 activity assay comparing EXT606, EXT608, EXT611, EXT615, EXT616, and EXT617.

PEG Length Effects on PTHR1 Receptor Activity: The above compounds, along with EXT608, (all acetate salts) were dissolved in PBS and the concentration was determined using an extinction coefficient at 280 nm of 18,600 M1 cm−1. The concentration of each compound was adjusted to 100 μM and submitted to DiscoverX (Fremont, CA, part of Eurofins Scientific) and tested in an assay with mammalian cells expressing the human PTH1 receptor (PTHR1) using a calcium mobilization assay in the agonist mode as described above in Example 3. Cells expressing PTHR1 were treated with 10 concentrations of test article in duplicate at a highest concentration of 1 μM and EC50 values were determined from plots of percent efficacy as a function of agonist concentration (FIG. 9) as shown in Table 1:

TABLE 1

PTHR1 EC50 values as a function of PEG length.

| Compound | # PEG$_x$ units (x) | PEG MW (Da.) | EC50 (nM) |
|---|---|---|---|
| EXT611 | 12 | 528 | 32.3 |
| EXT606 | 24 | 1056 | 30.5 |
| EXT608 | 36 | 1,584 | 28.6 |
| EXT615 | ~114 | ~5,000 | 29.9 |
| EXT616 | ~227 | ~10,000 | 33.6 |
| EXT617 | ~455 | ~20,000 | 221.3 |

EC50 values were independent of PEGx linker length through the range of x=12 to ~227 (528 to 10,000 Da.) The PEG20 kDa linker (EXT617), however, showed an EC50 value that was approximately 7-fold higher (221.3 nM). Without being bound by theory, this increase in agonist concentration required to achieve 50% maximal efficacy may have been due to the large size of the 20 kDa PEG linker blocking binding of the much smaller conjugated PTH peptide (~4 kDa) to the PTHR1.

PEG Length and Counterion Affects Solubility: The solubility of the acetate and carbonate salt form of each compound was determined as follows. For EXT611, EXT606, and EXT608, phosphate buffered saline (PBS) was added to each compound to form a saturated solution. Undissolved compound was removed by centrifugation. The concentration of dissolved compound was determined by measuring the absorbance at 280 nm using an extinction coefficient of 18,600 M$^{-1}$ cm$^{-1}$. For EXT615, EXT616, and EXT617, solubility was limited practically by the high viscosity imparted by the large PEG moieties. Highly viscous drug formulations are difficult to manipulate and require large needle bore sizes that cause increased injection site pain. PBS was added to EXT615, EXT616, and EXT617 incrementally until a solution was obtained that could be successfully pipetted through a pipet tip with a bore of approximately 1 mm diameter (enlarged by removing the end with a razor blade). The concentration of dissolved compound was determined by measuring the absorbance at 280 nm using an extinction coefficient of 18,600 M$^{-1}$ cm$^{-1}$. It was surprising that for each compound, the acetate salt had a higher solubility than the carbonate salt (Table 2). For EXT608, the acetate salt was 17.6-fold more soluble than the carbonate salt. Maximal solubility is achieved with EXT608 acetate (9.67 mM). Increasing the PEG length resulted in increased solubility, but this is ultimately limited by the highly viscous semi-solid gelatinous solutions obtained with PEG linkers≥5 kDa.

TABLE 2

PBS solubility as a function of PEG length and counterion

| Compound | # PEG$_x$ units (x) | PEG MW (Da.) | Solubility as Acetate (mM) | Solubility as Carbonate (mM) |
|---|---|---|---|---|
| EXT611 | 12 | 528 | 0.269 | 0.055 |
| EXT606 | 24 | 1056 | 0.907 | 0.200 |
| EXT608 | 36 | 1,584 | 9.67 | 0.550 |
| EXT615 | ~114 | ~5,000 | 7.89 | 5.16 |
| EXT616 | ~227 | ~10,000 | 5.40 | 4.16 |
| EXT617 | ~455 | ~20,000 | 4.11 | 1.88 |

Example 6: Single Dose Pharmacokinetics of EXT601 in Male Rats

Figure 10:
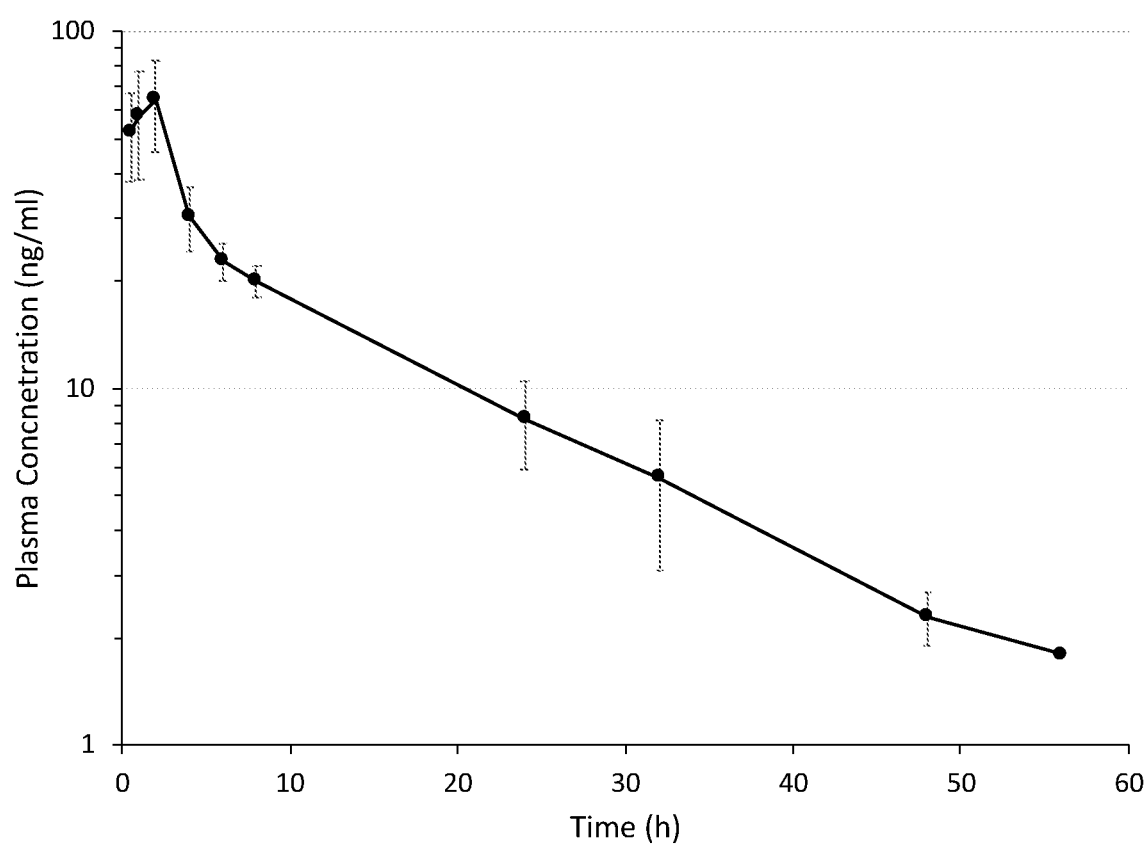
FIG. 10: Pharmacokinetics of subcutaneously dosed EXT601 (157 µg/kg) in rats. Error bars indicate the standard deviation (n=3).

In a single dose pharmacokinetic study, EXT601 was formulated in PBS and male rats (n=3) were dosed subcutaneously at a volume of 1 ml/kg and a dose of 157 μg/kg. Blood was collected via the jugular vein cannula at 0.5, 1, 2, 4, 6, 8, 24, 32, 48 and 56 hours, and processed into plasma. Plasma levels of EXT601 were determined using the Immutopics High-sensitivity Human Parathyroid Hormone PTH(1-34) ELISA kit (cat #: 60-3900, Quidel Corporation, San Diego, CA). Group-averaged EXT601 levels as a function of time are shown in FIG. 10.

Pharmacokinetic parameters were determined from the plasma concentration versus time data by a non-compartmental analysis using Kinetica software (Thermo Fisher Scientific, Waltham, MA). EXT601 reached a $C_{max}$ of 64.4 ng/ml at a $T_{max}$ of 2 hours as described in Table 3. EXT601 had an elimination half-life of 13.5 hours with a low clearance of 20.1 ml/h/kg.

TABLE 3

Pharmacokinetic Parameters of a Single Subcutaneous Dose of EXT601 in Rat

| PK Parameter (units) | Result |
|---|---|
| $t_{1/2}$ (h) | 13.5 |
| $T_{max}$ (h) | 2.0 |
| $C_{max}$ (ng/mL) | 64.4 |
| $AUC_{last}$ (h · ng/mL) | 665 |
| $AUC_{inf}$ (h · ng/mL) | 700 |
| Cl (mL/h/kg) | 20.1 |
| $V_Z$ (mL/kg) | 4,376 |
| MRT (h) | 16.5 |

$t_{1/2}$, terminal half-life; Tmax, time of maximum observed concentration; Cmax, maximum observed concentration; $AUC_{last}$, area under the concentration-time curve from time = 0 to the timepoint with the last measurable concentration; $AUC_{inf}$, area under the concentration-time curve from time = 0 to infinity; Cl, clearance; $V_Z$, apparent volume of distribution during the terminal phase; MRT, mean retention time.

Example 7: Single Dose Pharmacokinetics of EXT607 in Male Rats

Figure 11:
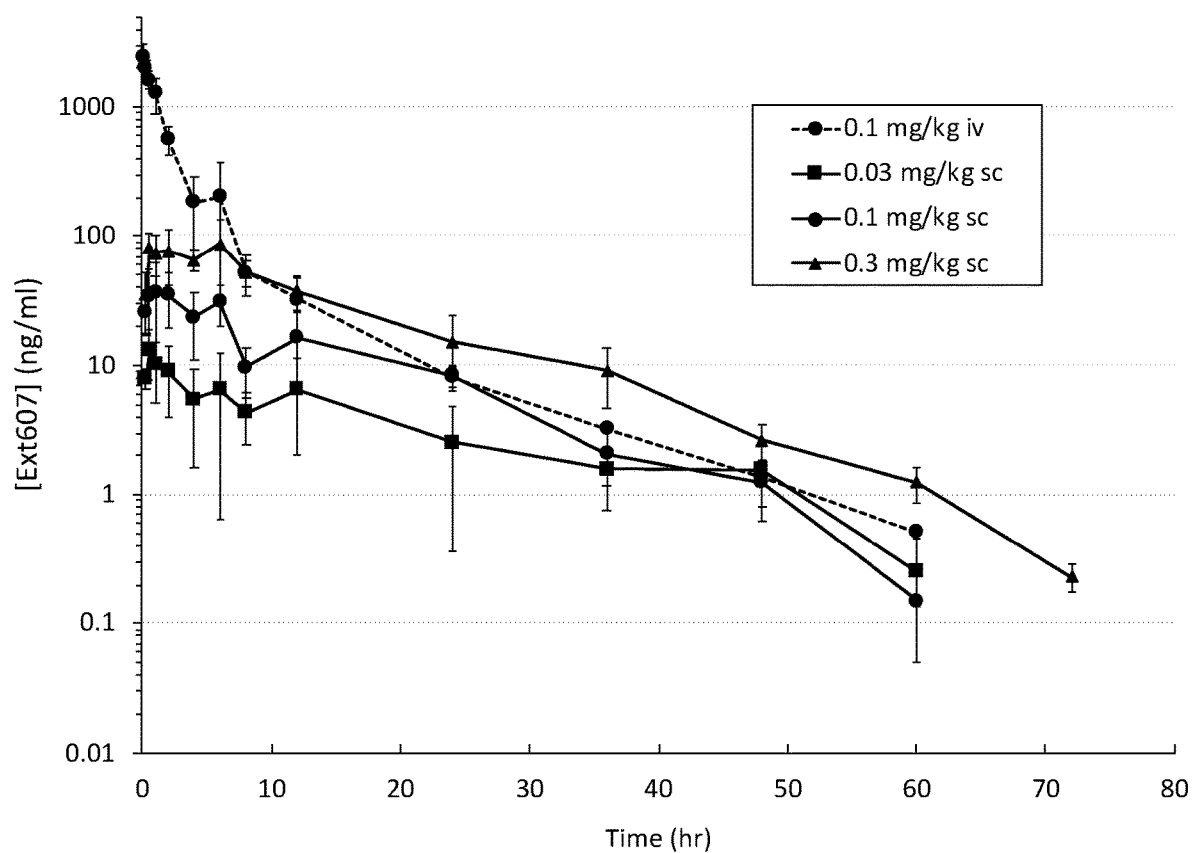
FIG. 11: Pharmacokinetics of intravenously (iv, dashed line) and subcutaneously (sc, solid lines) dosed EXT607 in rats. Error bars indicate the standard deviation (n=3).

In a single dose pharmacokinetic study, EXT607 was formulated in PBS and groups of male rats (n=3) were dosed at a volume of 1 ml/kg as follows: Group 1, 100 μg/kg intravenous; Group 2, 30 μg/kg subcutaneous; Group 3, 100

µg/kg subcutaneous; Group 4, 300 µg/kg subcutaneous. Blood (0.25 mL) was collected via the jugular vein cannula, transferred into tubes containing K₂EDTA, and kept on wet ice until processed for plasma. Blood samples were collected at 0 (predose), 0.083 (IV only), 0.25, 0.5, 1, 2, 4, 6, 8, 12, 24, 36, 48, 60 and 72 h postdose. Plasma levels of EXT607 were determined at Extend Biosciences using the Immutopics High-sensitivity Human Parathyroid Hormone PTH(1-34) ELISA kit (cat #: 60-3900, Quidel Corporation, San Diego, CA). Group-averaged EXT607 levels as a function of time are shown in FIG. 11.

Pharmacokinetic parameters were determined from the plasma concentration versus time data (Table 4) by a non-compartmental analysis with uniform weighting using Phoenix® WinNonlin® Version 6.3 (Certara L.P. (Pharsight), St. Louis, MO). The concentration versus time data were analyzed using the IV bolus or extravascular administration models. Best fit Lambda z ranges were used. EXT607 had a subcutaneous bioavailability (% F) of 10-13% in male rats based on AUC when compared to an intravenous injection. The $C_{max}$ was reached within 0.5 to 3 hours following SC administration of 30, 100 or 300 µg/kg, and then EXT607 was eliminated slowly with a clearance of 22.9 to 25.9 ml/h/kg, a half-life of 7 to 15 h, and a mean retention time of 13.6 to 15.9 h.

Pharmacokinetic parameters were determined from the plasma concentration versus time data (Table 5) by a non-compartmental analysis with uniform weighting using Phoenix® WinNonlin® Version 6.3 (Certara L.P. (Pharsight), St. Louis, MO). The concentration versus time data were analyzed using the IV bolus or extravascular administration models. Best fit Lambda z ranges were used. EXT607 has a $t_{1/2}$ of elimination of 24-32 hours. When delivered subcutaneously, bioavailability is 45-54%, and clearance is low (6.63-7.28 ml/h/kg).

Dose linearity was observed for AUC (dose-adjusted ratios of 0.95:0.85:1.00), but not for Cmax (0.28:0.55:1.00). This is because dose affects the rate of subcutaneous absorption and hence the Cmax. At low doses, the rate of subcutaneous absorption is slower than at high doses, leading to a lower Cmax and an overall flatter PK profile. The slower subcutaneous rate of absorption at low doses is also reflected in the higher mean retention time (MRT) with a MRT of 29.46 h at the low dose, 23.26 h at the middle dose, and 17.51 h at the high dose.

TABLE 4

Pharmacokinetic Parameters of a Single Dose of EXT607 in Rat

| PK Parameter (units) | Dose/Route | | | |
|---|---|---|---|---|
| | 100 µg/kg IV | 30 µg/kg SC | 100 µg/kg SC | 300 µg/kg SC |
| $t_{1/2}$ (h) | 8.43 | 15.4 | 7.36 | 9.21 |
| $T_{max}$ (h) | 0.139 | 0.420 | 1.330 | 3.000 |
| $C_0$ (ng/mL) | 2860 | N/A | N/A | N/A |
| $C_{max}$ (ng/mL) | 2560 | 13.9 | 43.7 | 109 |
| $AUC_{last}$ (h · ng/mL) | 4380 | 170 | 468 | 1270 |
| $AUC_{inf}$ (h · ng/mL) | 4390 | 186 | 472 | 1290 |
| Cl (mL/h/kg) | 24.1 | 24.1 | 25.9 | 22.9 |
| $V_Z$ (mL/kg) | 304 | 4630 | 2520 | 3160 |
| MRT (h) | 3.49 | 15.89 | 13.72 | 13.55 |
| Bioavailability (%) | N/A | 12.94 | 10.68 | 9.67 |

IV, intravenous; SC, subcutaneous; N/A, not applicable; $t_{1/2}$, terminal half-life; Tmax, time of maximum observed concentration; $C_0$, calculated initial concentration; Cmax, maximum observed concentration; $AUC_{last}$, area under the concentration-time curve from time = 0 to the timepoint with the last measurable concentration; $AUC_{inf}$, area under the concentration-time curve from time = 0 to infinity; Cl, clearance; $V_Z$, apparent volume of distribution during the terminal phase; MRT, mean retention time.

Example 8: Single Dose Pharmacokinetics of EXT607 in Male Monkeys

Figure 12:
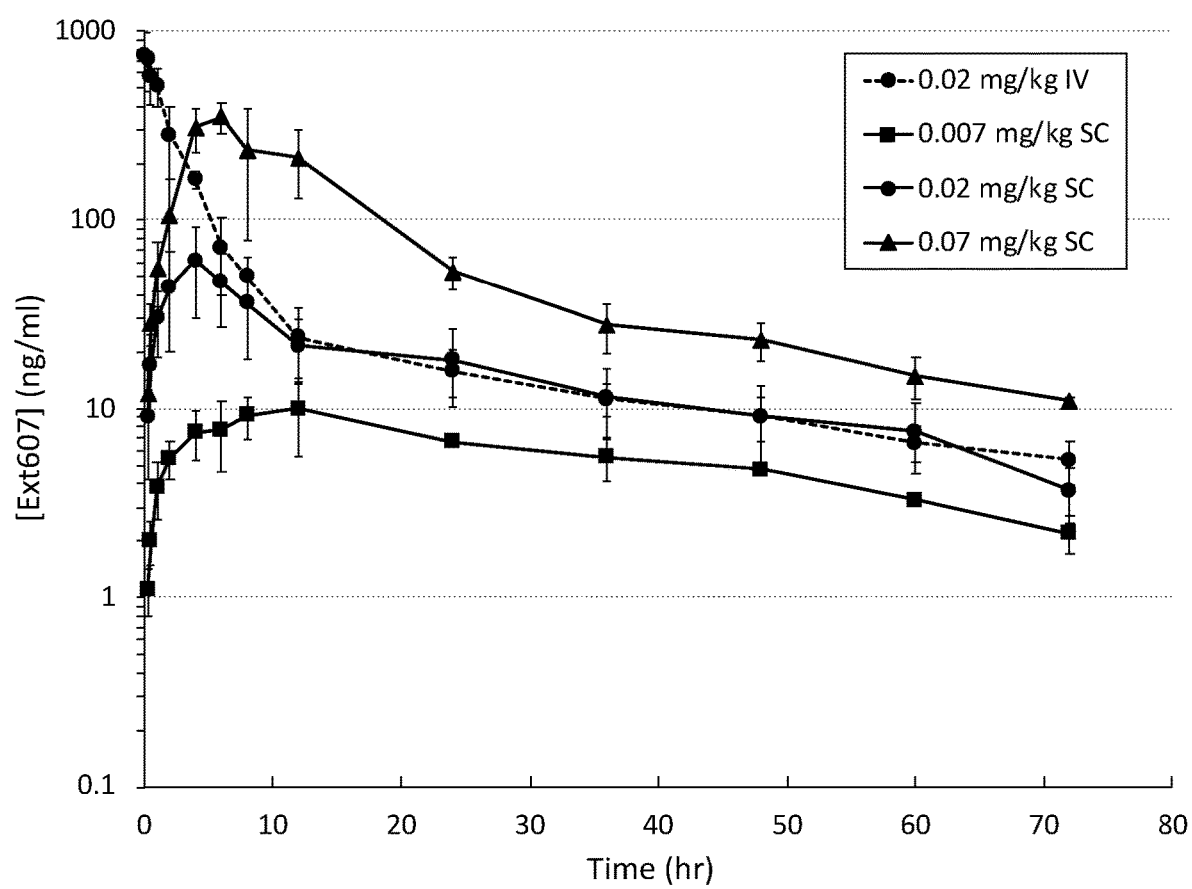
FIG. 12: Pharmacokinetics of intravenously (iv, dashed line) and subcutaneously (sc, solid lines) dosed EXT607 in cynomolgus monkeys. Error bars indicate the standard deviation (n=3).

In a single dose pharmacokinetic study, EXT607 was formulated in PBS and groups of male cynomolgus monkeys (n=3), weighing approximately 4 kg each, were dosed at a volume of 1 ml/kg as follows: Group 1, 20 µg/kg intravenous; Group 2, 7 µg/kg subcutaneous; Group 3, 20 µg/kg subcutaneous; Group 4, 70 µg/kg subcutaneous. Blood (1.0 mL) was collected via the jugular vein cannula, transferred into tubes containing K₂EDTA, and kept on wet ice until processed for plasma. Blood samples were collected at 0 (pre-dose), 0.083 (IV only), 0.25, 0.5, 1, 2, 4, 6, 8, 12, 24, 36, 48, 60 and 72 h post-dose. Plasma levels of EXT607 were determined using the Immutopics High-sensitivity Human Parathyroid Hormone PTH(1-34) ELISA kit (Quidel Corp., San Diego, CA Catalog No. 60-3900). Group-averaged EXT607 levels as a function of time are shown in FIG. 12.

TABLE 5

Pharmacokinetic Parameters of a Single Dose of EXT607 in Cynomolgus Monkeys

| PK Parameter (units) | Dose/Route | | | |
|---|---|---|---|---|
| | 20 µg/kg IV | 7 µg/kg SC | 20 µg/kg SC | 70 µg/kg SC |
| $t_{1/2}$ (h) | 32.29 | 24.02 | 24.31 | 27.72 |
| $T_{max}$ (h) | 0.19 | 10.67 | 4 | 6 |
| $C_0$ (ng/mL) | 782 | N/A | N/A | N/A |
| $C_{max}$ (ng/mL) | 789 | 10.8 | 61.1 | 389 |
| $AUC_{last}$ (h · ng/mL) | 2590 | 403 | 1160 | 4850 |
| $AUC_{inf}$ (h · ng/mL) | 2850 | 483 | 1290 | 5300 |
| Cl (mL/h/kg) | 7.34 | 6.63 | 8.02 | 7.28 |
| $V_Z$ (mL/kg) | 340 | 488 | 636 | 534 |
| MRT (h) | 11.20 | 29.46 | 23.26 | 17.51 |
| Bioavailability (%) | N/A | 44.46 | 44.79 | 53.50 |

Example 9: Repeat Dose Pharmacokinetics of EXT608 in Male and Female Rats

21-Day Experiment: EXT608 was formulated in 20 mM sodium acetate pH=5.5 buffer with 0.8% sodium chloride. In a repeat dose toxicokinetic study, groups of 18 rats (9 males+9 females) were subcutaneously dosed daily at a volume of 0.5 ml/kg with either 14.2 µg/kg or 70 µg/kg of EXT608. On Day 21, blood samples (~0.5 ml) were collected at t=0 (pre-dose), 0.5, 1, 3, 8, 24, 32, 48, and 72 h with each timepoint being collected from one of three cohorts of 3 male and 3 female animals. Each blood sample was collected from the jugular vein into tubes containing K₂EDTA and manually inverted several times. Blood samples were kept on wet ice pending centrifugation. Samples were centrifuged (~2700 g, ~10 min, ~5° C.) within 1 hour of collection. Plasma was recovered and divided evenly into duplicate aliquots and frozen.

90-Day Experiment: EXT608 was formulated in 20 mM sodium acetate pH=5.5 buffer with 0.8% sodium chloride and 0.1% Polysorbate 80. In a repeat dose toxicokinetic study, groups of 18 rats (9 males+9 females) were subcutaneously dosed daily at a volume of 0.5 ml/kg with either 1, 3, or 10 µg/kg of EXT608. On Day 90, blood samples (~0.5 ml) were collected at t=0 (pre-dose), 0.5, 1, 3, 8, 24, 32, 48, and 72 h with each timepoint being collected from one of three cohorts of 3 male and 3 female animals. Plasma was prepared as described above for the 21-Day experiment.

Figure 13:
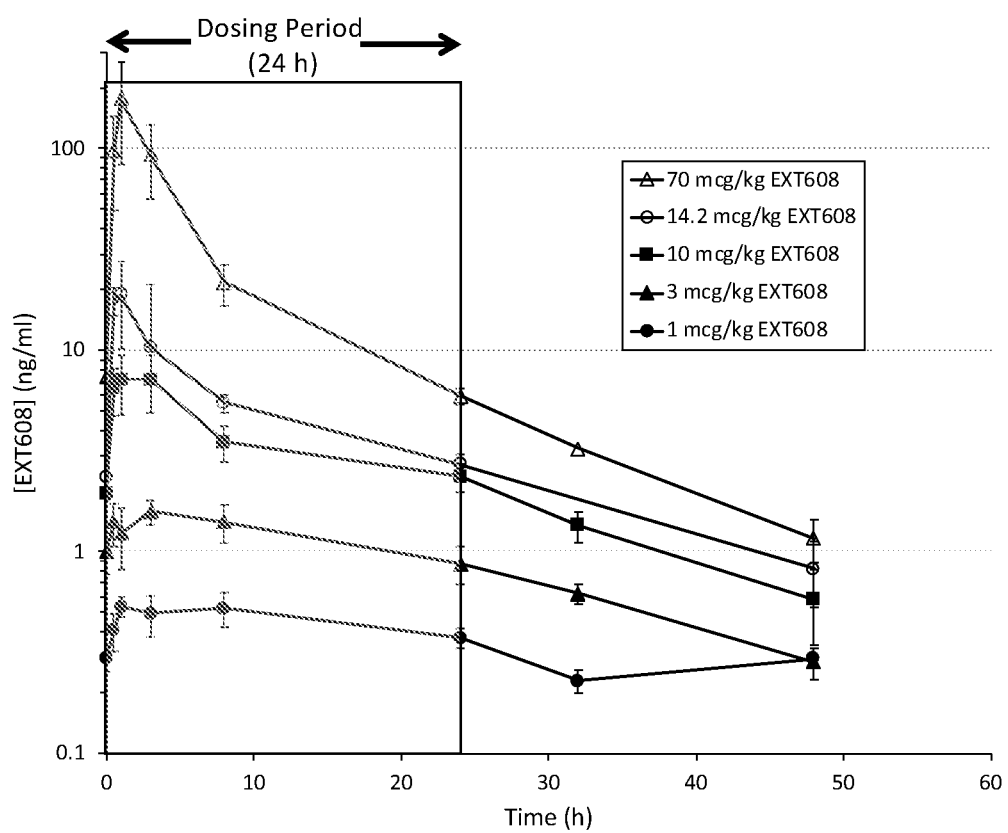
FIG. 13: Repeat-dose subcutaneous pharmacokinetics of EXT608 in rats as measured following the last dose administration after either 21 days of daily dosing (14.2 and 70 µg/kg) or 90 days of daily dosing (1, 3, and 10 µg/kg). Error bars indicate the standard deviation (n=3).

Pharmacokinetic Analysis: Plasma levels of EXT608 were determined using the Immutopics High-sensitivity Human Parathyroid Hormone PTH(1-34) ELISA kit (Quidel Corporation, San Diego, CA Catalog No. 60-3900). Group-averaged EXT608 levels as a function of time are shown in FIG. 13 for the last dose administration after either 21 days of daily dosing (14.2 and 70 μg/kg) or 90 days of daily dosing (1, 3, and 10 μg/kg). Surprising, the PK profiles changed as a function of dose level. The higher doses showed a more prominent peak while lower doses had a flatter profile and less pronounced peak.

Pharmacokinetic parameters were determined from the plasma concentration versus time data (Table 6) by a non-compartmental extravascular administration model with uniform weighting using Phoenix® WinNonlin® Version 6.4 (Certara L.P. (Pharsight), Princeton, NJ). Pharmacokinetic analysis was performed on data collected from t=0 to 72 h following the last administered dose. The $t_{1/2}$ of elimination values ranged from 10.4 to 13.8 h. In order to quantify the observed dose-dependent changes in PK profile, the $C_{max}$ and $C_{min}$ values were determined for the time period between 0-24 h, which was the normal dosing period. The $C_{max}/C_{min}$ ratio represents the peak-to-trough ratio of EXT608 concentration that was observed during the dosing period. This ratio decreased from 30 at the highest dose (70 μg/kg) to 8.0 at 14.2 μg/kg, 4.6 at 10 μg/kg, and 1.8 at 3 μg/kg and 1 μg/kg. Without being bound by theory, the low peak-to-trough ratios observed at low doses could be the result of a slower rate of absorption of EXT608 from the subcutaneous space into circulation. A low peak-to-trough ratio is desirable in many therapeutic applications, including parathyroid hormone replacement therapy. It allows dosing at levels close to the ideal efficacious dose without going too high where toxicity might be observed or too low where the efficacy is reduced.

TABLE 6

PK Parameters of EXT608 in Rats Following Repeated Daily SC Dosing

| PK Parameter (units) | Dose | | | | |
|---|---|---|---|---|---|
| | 70 μg/kg | 14.2 μg/kg | 10 μg/kg | 3 μg/kg | 1 μg/kg |
| Days of dosing | 21 | 21 | 90 | 90 | 90 |
| $t_{1/2}$ (h) | 11.7 | 13.8 | 10.4 | 12.5 | 11.1 |
| $T_{max}$ (h) | 1 | 0.75 | 3 | 3 | 1 |
| $AUC_{0-24\,h}$ (h · ng/mL) | 875 | 149 | 93.2 | 29.9 | 11.2 |
| $AUC_{last}$ (h · ng/mL) | 972 | 204 | 133 | 42.7 | 14.5 |
| $C_{max}$ (ng/mL) | 177 | 18.8 | 7.16 | 1.60 | 0.534 |
| $C_{min}$ (ng/mL) | 5.92 | 2.35 | 1.56 | 0.875 | 0.299 |
| $C_{max}/C_{min}$ (0-24 h) | 29.9 | 8.00 | 4.59 | 1.83 | 1.79 |

$t_{1/2}$, terminal half-life; $T_{max}$, time of maximum observed concentration; $AUC_{0-24\,h}$, area under the concentration-time curve from time = 0 to 24 h; $AUC_{last}$, area under the concentration-time curve from time = 0 to the timepoint with the last measurable concentration; $C_{max}$, maximum observed concentration; $C_{min}$, minimum observed concentration from time = 0 to 24 h; $C_{max}/C_{min}$ (0-24 h), ratio of $C_{max}/C_{min}$.

Example 10: Repeat Dose Pharmacokinetics of EXT608 in Male and Female Cynomolgus Monkeys 21-Day Experiment: EXT608 was formulated in 20 mM sodium acetate pH=5.5 buffer with 0.8% sodium chloride. In a repeat dose toxicokinetic study, groups of 4 cynomolgus monkeys (2 males+2 females weighing approximately 2.5 kg each) were subcutaneously dosed every other day at a volume of 0.05 ml/kg with either 1.4, 7 or 20 μg/kg of EXT608. On the last day of dosing, Day 21, blood samples (~1.0 ml) were collected at t=0 (pre-dose), 0.5, 1, 3, 6, 12, 24, 48, and 72 h. Each blood sample was collected from the saphenous vein into tubes containing $K_2$EDTA and centrifuged (~2700 g, ~10 min, ~5° C.) within 1 hour of collection. Plasma was recovered and divided evenly into duplicate aliquots and frozen.

90-Day Experiment: EXT608 was formulated in 10 mM sodium acetate pH=5.5 buffer with 0.8% sodium chloride and 0.1% Polysorbate 80. In a repeat dose toxicokinetic study, groups of 6 cynomolgus monkeys (3 males+3 females) were subcutaneously dosed every other day at a volume of 0.05 ml/kg with either 0.7 or 2 μg/kg of EXT608. On the last day of dosing, Day 89, blood samples (~1.0 ml) were collected at t=0 (pre-dose), 0.5, 1, 3, 6, 12, 24, 48, and 72 h. Plasma was prepared as described above for the 21-Day experiment.

Figure 14:
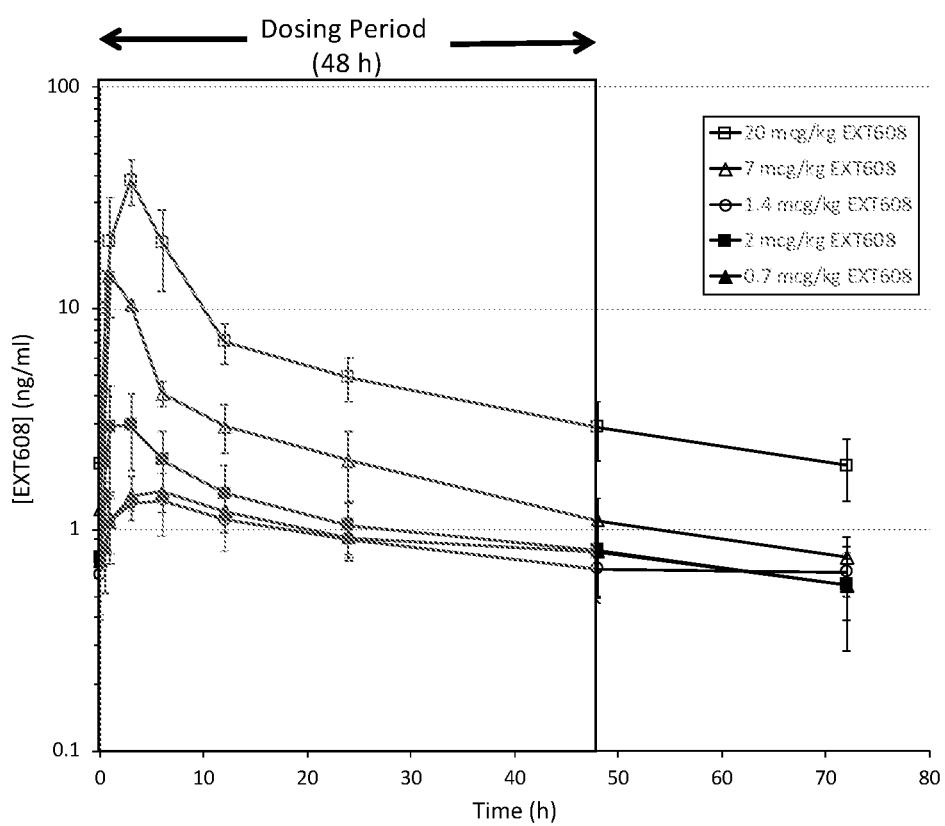
FIG. 14: Repeat-dose subcutaneous pharmacokinetics of EXT608 in cynomolgus monkeys as measured following the last dose administration after either 21 days of every other day dosing (1.4, 7, and 20 µg/kg) or 89 days of every other day dosing (0.7 and 2 µg/kg). Error bars indicate the standard deviation (n=3).

Pharmacokinetic Analysis: Plasma levels of EXT608 were determined using the Immutopics High-sensitivity Human Parathyroid Hormone PTH(1-34) ELISA kit (Quidel Corporation, San Diego, CA, Catalog No. 60-3900). Group-averaged EXT608 levels as a function of time are shown in FIG. 14 for the last dose administration after either 21 days of every other day dosing (20, 7, and 1.4 μg/kg) or 89 days of every other day dosing (2 and 0.7 μg/kg). Surprising, the PK profiles changed as a function of dose level. The higher doses showed a more prominent peak while lower doses had a flatter profile and less pronounced peak.

Pharmacokinetic parameters were determined from the plasma concentration versus time data (Table 7) by a non-compartmental extravascular administration model with uniform weighting using Phoenix® WinNonlin® Version 6.4 (Certara L.P. (Pharsight), Princeton, NJ). Pharmacokinetic analysis was performed on data for individual animals collected from t=0 to 72 h following the last administered dose. The $t_{1/2}$ of elimination values ranged from 34.7 to 51.0 h. It is noted that the $t_{1/2}$ values were calculated from less than three half-lives of data. In order to quantify the observed dose-dependent changes in PK profile, the $C_{max}$ and $C_{min}$ values were determined for the time period between 0-48 h, which was the normal dosing period. The $C_{max}/C_{min}$ ratio represents the peak-to-trough ratio of EXT608 concentration that is observed during a dosing period. This ratio decreased from 19.3 at the highest dose (20 μg/kg) to 14.2 at 7 μg/kg, 5.4 at 2 μg/kg, 3.4 at 1.4 μg/kg and 2.4 at 0.7 μg/kg. Without being bound by theory, the low peak-to-trough ratios observed at low doses could be the result of a slower rate of absorption of EXT608 from the subcutaneous space into circulation. A low peak-to-trough ratio is desirable in many therapeutic applications including parathyroid hormone replacement therapy. This is because it allows dosing at levels close to the ideal efficacious dose without going too high where toxicity is observed, or too low where the efficacy is reduced.

TABLE 7

PK Parameters of EXT608 in Monkeys Following
Repeated Every-other-day SC Dosing

| PK Parameter (units) | Dose | | | | |
|---|---|---|---|---|---|
| | 20 μg/kg | 7 μg/kg | 1.4 μg/kg | 2 μg/kg | 0.7 μg/kg |
| Duration of dosing (days) | 21 | 21 | 21 | 89 | 89 |
| $t_{1/2}$ (h) | 35.9 | 34.7 | NE | 51.0 | 45.0 |
| $T_{max}$ (h) | 3.0 | 1.0 | 1.8 | NE | 6 |
| $AUC_{0\text{-}48\,h}$ (h · ng/mL) | 401 | 147 | 41.5 | 63.1 | 45.4 |
| $AUC_{last}$ (h · ng/mL) | 460 | 170 | 48.0 | 79.5 | 61.6 |
| $C_{max}$ (ng/mL) | 38.1 | 14.1 | 1.63 | 3.41 | 1.43 |
| $C_{min}$ (ng/mL) | 1.97 | 0.991 | 0.485 | 0.635 | 0.600 |
| $C_{max}/C_{min}$ (0-48 h) | 19.3 | 14.2 | 3.36 | 5.37 | 2.38 |

$t_{1/2}$, terminal half-life; $T_{max}$, time of maximum observed concentration; $AUC_{0\text{-}48\,h}$, area under the concentration-time curve from time = 0 to 48 h; $AUC_{last}$, area under the concentration-time curve from time = 0 to the timepoint with the last measurable concentration; $C_{max}$, maximum observed concentration; $C_{min}$, minimum observed concentration from time = 0 to 48 h; $C_{max}/C_{min}$ (0-48 h), ratio of $C_{max}/C_{min}$. NE, not estimated.

Figure 15:
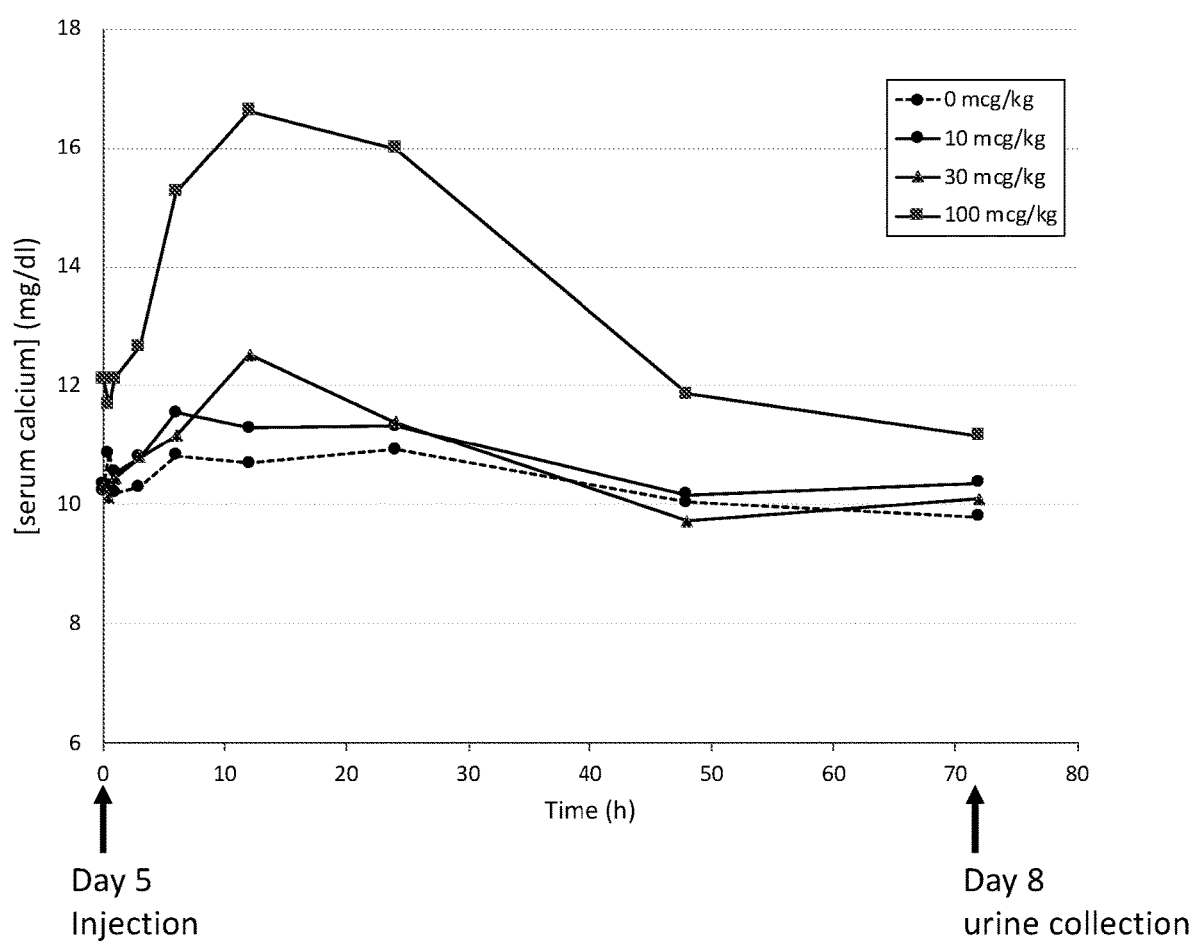
FIG. 15: Serum calcium levels in cynomolgus monkeys beginning on Day 5 after every other day subcutaneous dosing of EXT607 at 0, 10, 30, or 100 µg/kg. Animals were dosed at t=0 on Days 1, 3, and 5, with the administration on Day 5 indicated on the graph by a vertical arrow. Urine was collected beginning on Day 8 (72 h on the time axis) as indicated by the horizontal arrow.

Example 11: Effect of EXT607 and EXT608 on Serum Calcium, Serum Phosphate, and Urinary Calcium in Male and Female Cynomolgus Monkeys 5-Day/8-Day Experiment: EXT607 was formulated in phosphate buffered saline pH=7.4. In a repeat dose toxicokinetic study groups of 4 cynomolgus monkeys (2 males+2 females weighing 2.5-3.7 kg each) were subcutaneously dosed every other day on Days 1, 3, and 5 at a volume of 1 ml/kg with either 0, 10, 30 or 100 μg/kg of EXT607. On Day 5, blood samples (~1.0 ml) were collected at t=0 (pre-dose), 0.5, 1, 3, 6, 12, 24, 48, and 72 h. Each blood sample was collected from the cephalic or saphenous vein into serum separator tubes and centrifuged (~2700 g, ~10 min, ~5° C.) within 1 hour of collection. Serum was recovered and analyzed for calcium and phosphate by colorimetric assay. EXT607 induced a dose-dependent increase in serum calcium levels that persisted for up to 48 h at the highest dose (FIG. 15). Changes in serum calcium levels were calculated for each timepoint by subtracting the baseline calcium levels (the 0 μg/kg group average for the same timepoint). The maximum change in calcium for the 72 h period was determined for each animal, and group averages and standard deviations were calculated (Table 8A). No effect on serum phosphorous was observed.

TABLE 8A

Dose-dependent serum calcium level changes following
Day 5 injection of EXT607 in cynomolgus monkeys

| EXT607 Dose | Maximal Change in Serum Ca (mg/dl) |
|---|---|
| 10 mcg/kg | 1.2 ± 0.4 |
| 30 mcg/kg | 1.8 ± 1.0 |
| 100 mcg/kg | 6.1 ± 3.8 |

On Days −3 and 8, urine was collected at room temperature via a pan placed under the cage. "Day −3" refers to a pre-dose timepoint that is three days before the first dose on day 1. Urinary calcium levels were measured using an Advia 1800 Clinical Chemistry System (Siemens Medical Solutions USA, Malvern, PA). Urinary calcium levels remained the same or decreased with EXT607 treatment (Table 8B). The Day 8 urine collection corresponds with the serum samples collected 72 h after the Day 5 injection. Therefore, EXT607 raised serum calcium levels without increasing urinary calcium as reflected by the lower urinary:serum calcium ratios with EXT607 dosing. This is beneficial because high urinary calcium can lead to deposits in the kidneys and loss of kidney function.

TABLE 8B

Dose-dependent effects of EXT607 on serum and urinary calcium

| Day/Dose | Urinary Ca (mg/dl) | Serum Ca (mg/dl) | Ratio Urinary:Serum Ca |
|---|---|---|---|
| Day −3 (pre-dose) | 30.1 | 9.8 | 3.1 |
| Day 8 (0 mcg/kg) | 32.5 | 9.8 | 3.3 |
| Day 8 (10 mcg/kg) | 19.1 | 10.4 | 1.8 |
| Day 8 (30 mcg/kg) | 31.2 | 10.1 | 3.1 |
| Day 8 (100 mcg/kg) | 13.2 | 11.2 | 1.2 |

21-Day Experiment: EXT608 was formulated in 20 mM sodium acetate pH=5.5 buffer with 0.8% sodium chloride. In a repeat dose toxicokinetic study, groups of 4 cynomolgus monkeys (2 males+2 females weighing approximately 2.5 kg each) were subcutaneously dosed every other day beginning on Day 1 at a volume of 0.05 ml/kg with either 1.4, 7 or 20 μg/kg of EXT608. On Days 1, 11, and 21, blood samples (~0.5 ml) were collected at t=0 (pre-dose), 0.5, 1, 3, 6, 12, 24, 48, and 72 h (Day 21 only). Each blood sample was collected from the saphenous vein into serum separator tubes and centrifuged (~2700 g, ~10 min, ~5° C.) within 1 hour of collection. Serum was recovered and analyzed for calcium and phosphate using an Advia 1800 Clinical Chemistry System (Siemens Medical Solutions USA, Malvern, PA).

Figure 16:
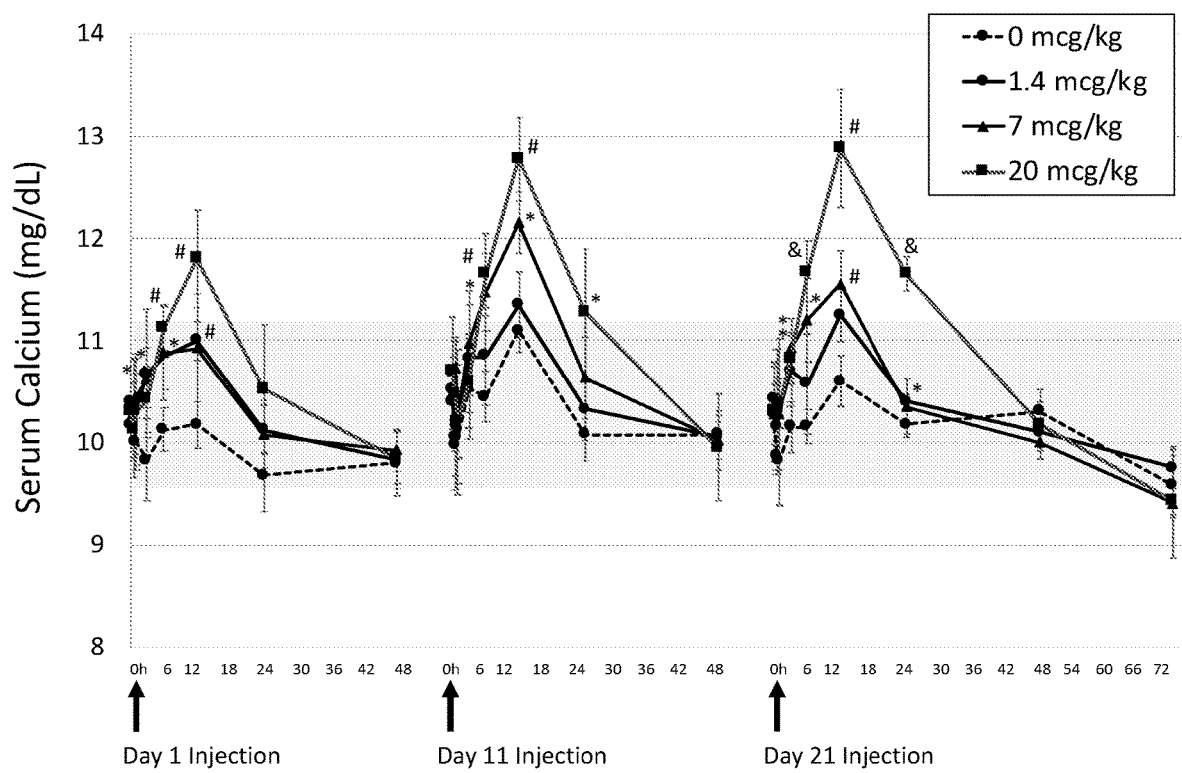
FIG. 16: Serum calcium levels in cynomolgus monkeys on Days 1, 11 and 21 after every other day subcutaneous dosing of EXT608 at 0, 1.4, 7, or 20 µg/kg. Error bars indicate the standard deviation (n=4). p-values vs the 0 µg/kg group (Vehicle) were calculated using the Student t-test (*<0.05, #<0.01, &<0.001).
Figure 17:
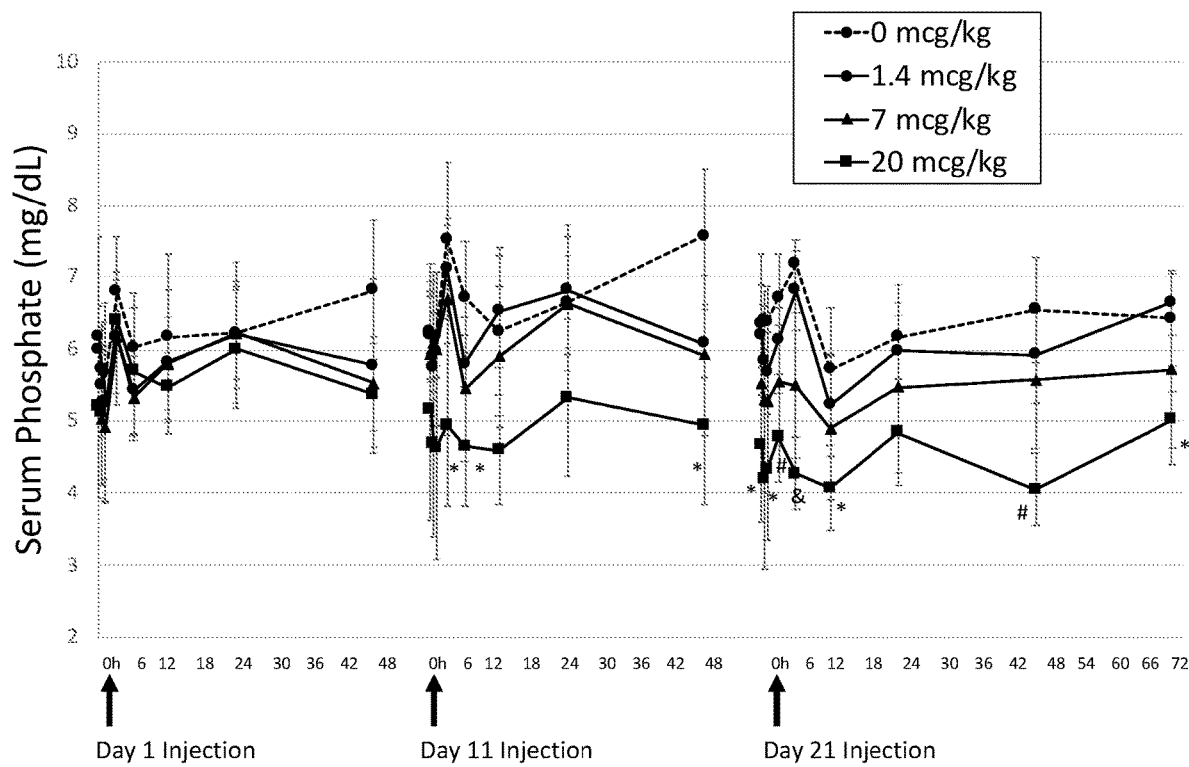
FIG. 17: Serum phosphate levels in cynomolgus monkeys on Days 1, 11 and 21 after every other day subcutaneous dosing of EXT608 at 0, 1.4, 7, or 20 µg/kg. Error bars indicate the standard deviation (n=4). p-values vs the 0 µg/kg group (Vehicle) were calculated using the Student t-test (*<0.05, #<0.01, &<0.001).

EXT608 induced a dose-dependent increase in serum calcium levels that persisted for up to 24 h (FIG. 16). Serum phosphate levels were not significantly changed on Day 1, but by Day 11, the high dose (20 μg/kg) caused a decrease in serum phosphate, and by Day 21 both the high and the middle dose (7 μg/kg) decreased serum phosphate with a duration of at least 72 h after dosing (FIG. 17). Changes in serum calcium values were calculated for each animal by subtracting the background level of the 0 μg/kg dosing group from each timepoint as described above. The maximal change observed for each animal was used to determine the group average and standard deviation (Table 8C). Changes in serum phosphate values were calculated for each group by subtracting the background level of the 0 μg/kg dosing group from each timepoint as described above. Because the reduction in phosphate levels persisted for the entire sampling period (48 or 72 h), group averages were determined by averaging the values from each timepoint within the sampling period (Table 8C). On Day −5 (pre-dose) and Day 24, urine was collected at room temperature via a pan placed under the cage. At these timepoints, neither serum nor urinary calcium levels were elevated.

TABLE 8C

Dose-dependent changes in serum calcium (Ca) and phosphate ($P_i$) for EXT608 following every-other-day dosing in cynomolgus monkeys for 21 days.

| EXT608 Dose | Change in Serum Ca (mg/dl) | | | Change in Serum $P_i$ (mg/dl) | | |
|---|---|---|---|---|---|---|
| | Day 1 | Day 11 | Day 21 | Day 1 | Day 11 | Day 21 |
| 1.4 mcg/kg | 1.2 ± 0.4 | 0.6 ± 0.5 | 0.8 ± 0.3 | −0.4 ± 0.4 | −0.4 ± 0.6 | −0.4 ± 0.3 |
| 7.0 mcg/kg | 1.0 ± 0.4 | 1.1 ± 0.4 | 1.2 ± 0.4 | −0.6 ± 0.4 | −0.6 ± 0.6 | −1.0 ± 0.3 |
| 20 mcg/kg | 1.6 ± 0.5 | 1.7 ± 0.5 | 2.3 ± 0.7 | −0.6 ± 0.4 | −1.8 ± 0.6 | −2.0 ± 0.5 |

Figure 18:
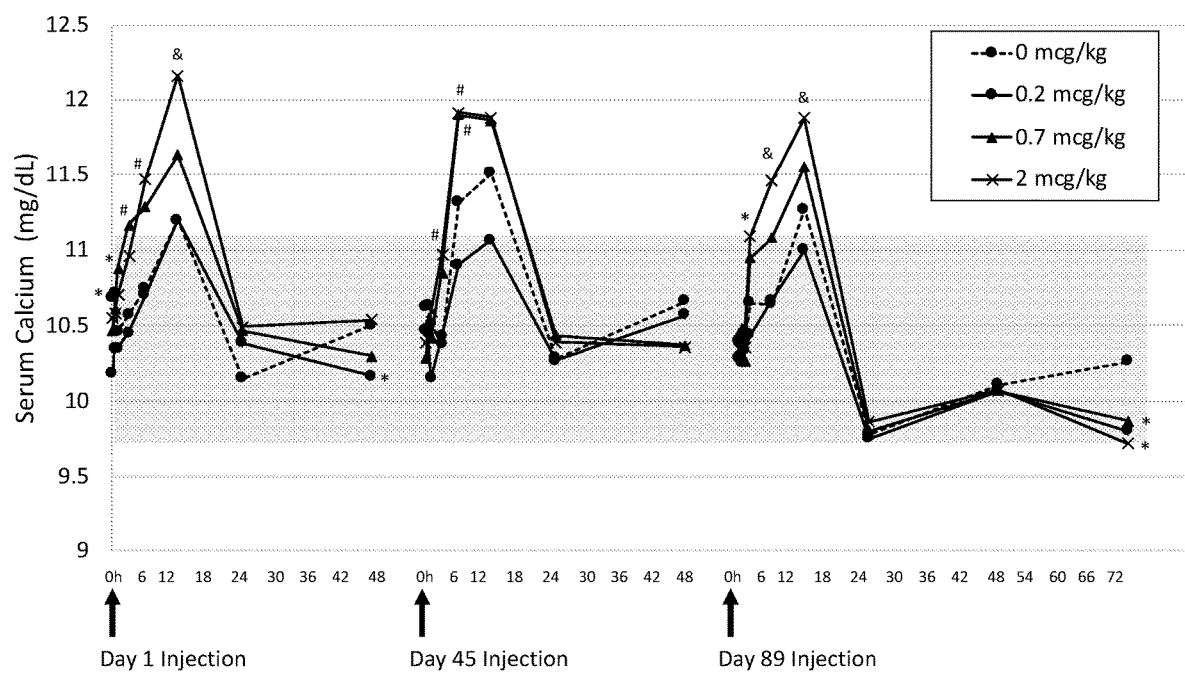
FIG. 18: Serum calcium levels in cynomolgus monkeys on Days 1, 45 and 89 after every other day subcutaneous dosing of EXT608 at 0, 0.2, 0.7, or 2 µg/kg. p-values vs the 0 µg/kg group (Vehicle) were calculated using the Student t-test (*<0.05, #<0.01, &<0.001).

90-Day Experiment: EXT608 was formulated in 10 mM sodium acetate pH=5.5 buffer with 0.8% sodium chloride and 0.1% Polysorbate 80. In a repeat dose toxicokinetic study, groups of 6 cynomolgus monkeys (3 males+3 females) were subcutaneously dosed every other day beginning on Day 1 at a volume of 0.05 ml/kg with either 0.7 or 2 μg/kg of EXT608. On Days 1, 45, and 89, blood samples (~0.5 ml) were collected at t=0 (pre-dose), 0.5, 1, 3, 6, 12, 24, 48, and 72 h (Day 89 only). Each blood sample was collected from the saphenous vein into serum separator tubes and centrifuged (~2700 g, ~10 min, ~5° C.) within 1 hour of collection. Serum was recovered and analyzed for calcium and phosphate using an Advia 1800 Clinical Chemistry System (Siemens Medical Solutions USA, Malvern, PA). EXT608 induced a dose-dependent increase in serum calcium levels that persisted for up to 12 h (FIG. 18). Changes in serum calcium values were calculated for each animal by subtracting the background level of the 0 μg/kg dosing group from each timepoint as described above. The maximal change observed for each animal was used to determine the group averages and standard deviations as reported in Table 8D. Serum phosphate levels were not significantly changed at these EXT608 doses. On Day −9 (pre-dose) and Day 90, urine was collected at room temperature via a pan placed under the cage. At these timepoints, neither serum nor urinary calcium levels were elevated.

TABLE 8D

Dose-dependent changes in serum calcium levels for EXT608 following every-other-day dosing in cynomolgus monkeys for 89 days.

| EXT608 Dose | Change in Serum Ca (mg/dl) | | |
|---|---|---|---|
| | Day 1 | Day 45 | Day 89 |
| 0.2 mcg/kg | 0.4 ± 0.3 | 0.2 ± 0.2 | 0.2 ± 0.2 |
| 0.7 mcg/kg | 0.9 ± 0.4 | 0.9 ± 0.1 | 0.6 ± 0.4 |
| 2 mcg/kg | 1.0 ± 0.6 | 0.9 ± 0.6 | 0.9 ± 0.4 |

Example 12: EXT607 is Efficacious in Thyroparathyroidectomized (TPTx) Rats 28-day Pharmacodynamic Study of EXT607 in TPTx Rats. Thyroparathyroidectomized (TPTx) rats are a model for hypoparathyroidism. To produce TPTx rats, the thyroid and parathyroid glands were surgically resected and the rats were given L-thyroxine to compensate for the loss of their thyroid. Due to the absence of PTH, TPTx rats had lower levels of serum calcium and higher levels of serum phosphate. Two weeks post-surgery, animals were dosed subcutaneously (SC) once daily (QD) for 28 days with wild-type PTH(1-34), PTH(1-84), or EXT607 as summarized in Table 9A:

TABLE 9A

Group Composition for TPTx 28-Day Study

| Group # | Surgical treatment | Test Compound | Dose Level (nmol/kg) | Dose Level (μg/kg) |
|---|---|---|---|---|
| 1 | Sham | Vehicle | 0 | 0 |
| 2 | TPTx | Vehicle | 0 | 0 |
| 3 | TPTx | EXT607 | 10 | 60 |
| 4 | TPTx | EXT607 | 3 | 20 |
| 5 | TPTx | EXT607 | 1 | 6 |
| 6 | TPTx | PTH(1-34) | 10 | 41 |
| 7 | TPTx | PTH(1-84) | 10 | 94 |

Each group consisted of 10 female rats split into two cohorts of 5 animals for blood sampling purposes. On days 1, 12, and 27, blood (~0.2 ml) was collected into serum separation tubes at t=0 (pre-dose), 2, 6, 10, and 24 h. The samples were processed into serum by standard methods and analyzed for serum total calcium and phosphate.

Figure 19:
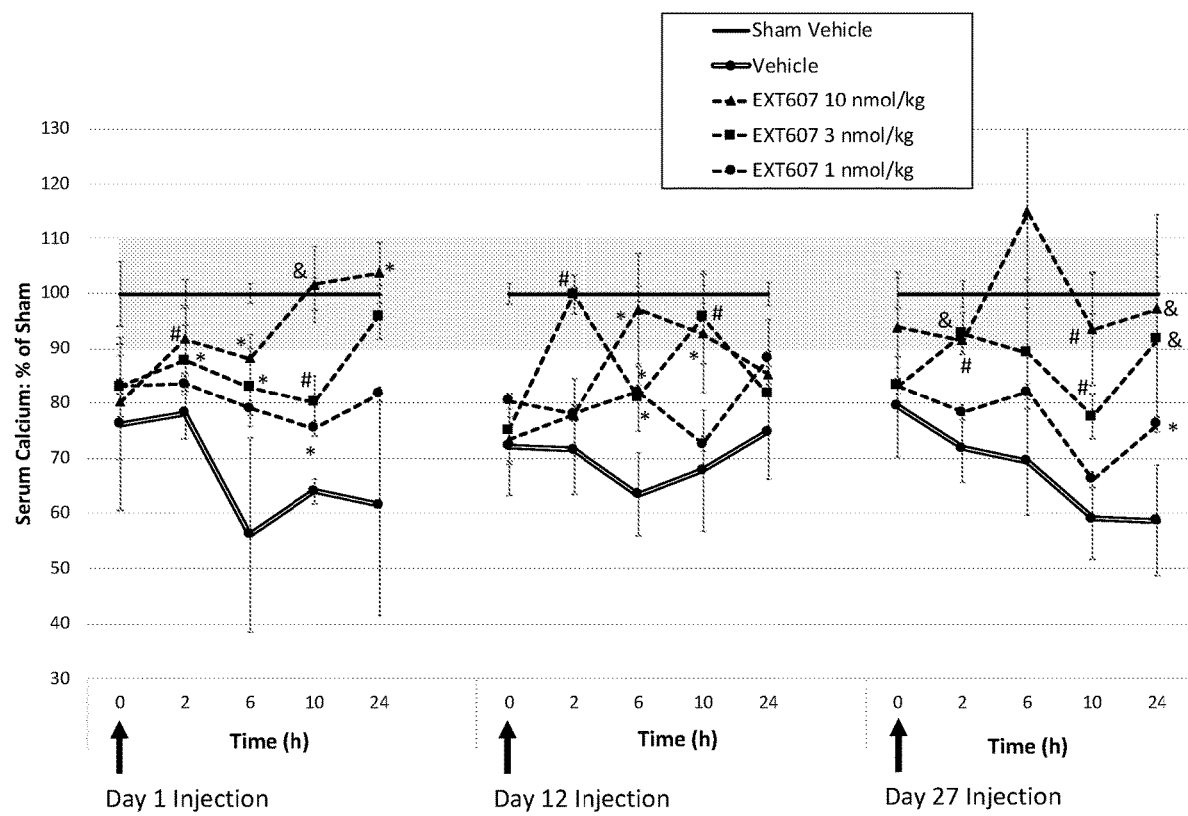
FIG. 19: Serum calcium levels in TPTx rats on Days 1, 12 and 27 after daily subcutaneous dosing of EXT607 at 0 (Vehicle), 1, 3, or 10 nmol/kg. Serum calcium values were normalized against the group which underwent a sham surgery and received vehicle (Sham Vehicle). Error bars indicate the standard deviation (n=5). p-values vs the 0 µg/kg group (Vehicle) were calculated using the Student t-test (*<0.05, #<0.01, &<0.001).
Figure 20:
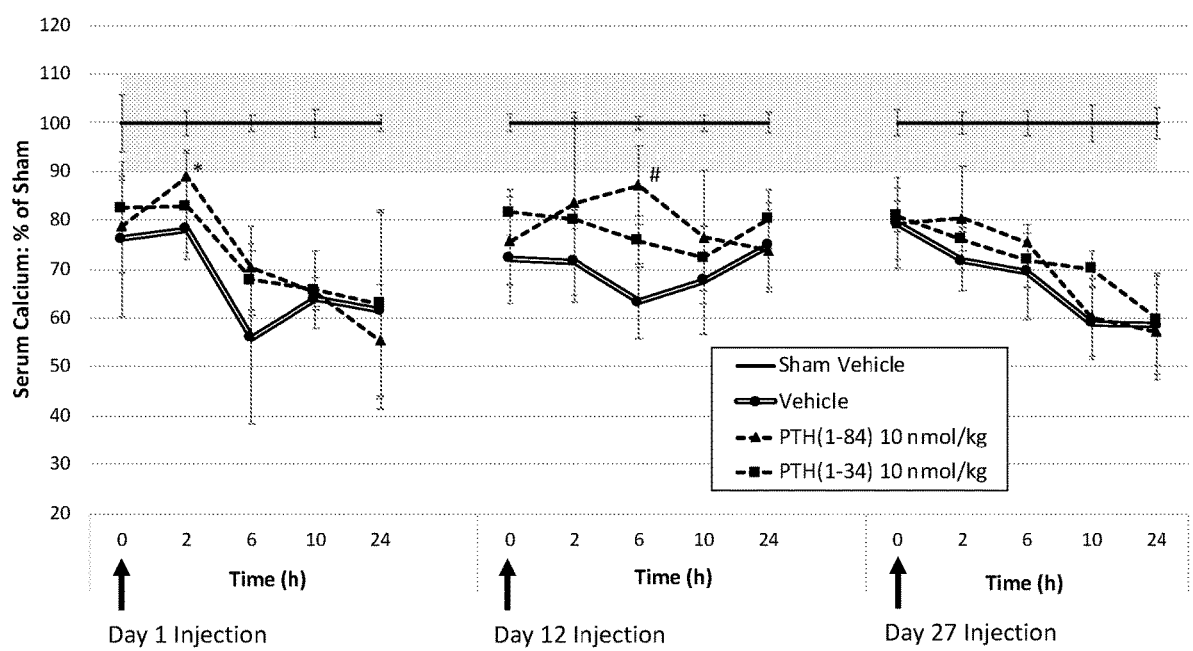
FIG. 20: Serum calcium levels in TPTx rats on Days 1, 12 and 27 after daily subcutaneous dosing of PTH(1-34) and PTH(1-84) at 10 nmol/kg as compared to the Vehicle and Sham Vehicle control groups from FIG. 19. Serum calcium values were normalized against the Sham Vehicle group.

EXT607 caused immediate dose-dependent increases in serum calcium compared to TPTx controls that lasted for the 24 h dosing period (FIG. 19). Calcium levels at 3 and 10 nmol/kg (20 and 60 μg/kg) were at or just below the normal range of calcium levels for healthy animals. At the 1 nmol/kg (6 μg/kg) dose, calcium levels were statistically increased compared to TPTx controls at various time points, but the calcium levels remained below the normal range for healthy animals. The increases in calcium observed with PTH(1-34) or PTH(1-84) administration were minimal and did not reach statistical significance with the exception of two isolated timepoints for PTH(1-84) (FIG. 20). For each timepoint, the percent increase in serum calcium relative to the TPTx vehicle control group (Group 2) was determined and daily averages were calculated (Table 9B). Over the three days sampled (Days 1, 12, and 27), EXT608 increased serum calcium an average of 17, 28, and 37% at 1, 3, and 10 nmol/kg, respectively. This is compared to an increase of 9% for 10 nmol/kg PTH(1-34) and PTH(1-84).

TABLE 9B

Percent increase in serum calcium relative to TPTx/vehicle.

| Group # | Test Compound | Dose Level (nmol/kg) | % Increase in Serum Calcium | | | |
|---|---|---|---|---|---|---|
| | | | Daily Average | | | Cumulative |
| | | | Day 1 | Day 12 | Day 27 | Days 1, 12, 27 |
| 3 | EXT607 | 10 | 42 | 23 | 47 | 37 |
| 4 | EXT607 | 3 | 30 | 24 | 30 | 28 |
| 5 | EXT607 | 1 | 22 | 15 | 15 | 17 |
| 6 | PTH(1-34) | 10 | 8.0 | 12 | 6.4 | 8.7 |
| 7 | PTH(1-84) | 10 | 7.0 | 14 | 4.1 | 8.5 |

Notable decreases in serum phosphate were observed with EXT607 at all dose levels starting on Day 12 and lasting for the remainder of the study (FIG. 21). Changes were observed in a dose-dependent manner with values generally comparable to sham controls at 3 and 10 nmol/kg. Slight decreases in phosphate levels were observed following treatment with PTH(1-84) at 10 nmol/kg starting on Day 12 after dosing and lasting for the remainder of the study (FIG. 22). Occasional decreases in serum phosphate were observed with PTH(1-34) at 10 nmol/kg. Reductions in serum phosphate with PTH(1-34) and PTH(1-84) were considerably less in magnitude than EXT607. At each timepoint, the percent decrease in serum phosphate relative to the TPTx vehicle control group (Group 2) was determined, and daily averages were calculated (Table 9C). Averaging all timepoints on Days 12 and 27, EXT608 decreased serum phosphate 15, 27, and 38% at 1, 3, and 10 nmol/kg, respectively compared to a decrease of 11 and 17% for 10 nmol/kg PTH(1-34) and PTH(1-84), respectively.

TABLE 9C

Percent decrease in serum phosphate relative to TPTx/vehicle.

| Group # | Test Compound | Dose Level (nmol/kg) | % Decrease in Serum Phosphate | | | |
|---|---|---|---|---|---|---|
| | | | Daily Average | | | Combined |
| | | | Day 1 | Day 12 | Day 27 | Days 12, 27 |
| 3 | EXT607 | 10 | 6.1 | 39 | 37 | 38 |
| 4 | EXT607 | 3 | 3.4 | 28 | 26 | 27 |
| 5 | EXT607 | 1 | −2.2 | 14 | 17 | 15 |
| 6 | PTH(1-34) | 10 | −1.7 | 9.1 | 13 | 11 |
| 7 | PTH(1-84) | 10 | 0.2 | 17 | 17 | 17 |

Example 13: Improved Formulation of EXT608

Stability as a Function of pH. The optimal pH maximizing the stability of EXT608 was determined as follows. EXT608 formulations at 1 mg/ml concentration were prepared in 50 mM sodium acetate buffer pH=4.5 and 5.5, and in phosphate buffer pH 6.5 and 8.0 containing 10 mg/mL of mannitol and incubated at −20° C., 2-8° C., and 25° C. Samples were analyzed after 10 weeks by reverse phase HPLC for concentration and purity (Table 10). The stability of EXT608 was highest at pH 4.5 and 5.5 and was reduced progressively as the pH was raised to 6.5 and 8.0.

TABLE 10

Concentration and % purity of EXT608 solutions after 10 weeks as a function of pH and incubation temperature.

| | Concentration (% of starting) | | | % Purity | | |
|---|---|---|---|---|---|---|
| pH | −20° C. | 2-8° C. | 25° C. | −20° C. | 2-8° C. | 25° C. |
| 4.5 | 100 | 101 | 8 | 88 | 88 | 48 |
| 5.5 | 99 | 72 | 0 | 87 | 84 | 52 |
| 6.5 | 86 | 43 | 0 | 81 | 69 | 38 |
| 8.0 | 50 | 18 | 0 | 39 | 37 | 24 |

To further investigate the effect of pH on the stability of EXT608, formulations at 0.4 mg/mL in 10 mM acetate buffer pH=4.0, pH=4.5, pH=5.0, pH=5.5 containing 0.9% saline were prepared by first dissolving the EXT608 API peptide in 10 mM acetic acid following pH adjustment with sodium hydroxide and tonicity adjustment with saline. The liquid formulations were filled into screw cap vials at 1 mL each. All formulations were incubated at −20° C., 2-8° C., 25° C. and tested at 6 months by reverse phase HPLC for concentration and % purity (Table 11). The stability of EXT608 was consistent across the pH range of between 4.0 and 5.5.

TABLE 11

Concentration and % purity of EXT608 solutions after 6 months as a function of pH and incubation temperature.

| | Concentration (% of starting) | | | % Purity | | |
|---|---|---|---|---|---|---|
| pH | −20° C. | 2-8° C. | 25° C. | −20° C. | 2-8° C. | 25° C. |
| 4.0 | 130 | 105 | 55 | 84 | 81 | 63 |
| 4.5 | 123 | 108 | 33 | 84 | 82 | 55 |

TABLE 11-continued

Concentration and % purity of EXT608 solutions after 6 months as a function of pH and incubation temperature.

| | Concentration (% of starting) | | | % Purity | | |
|---|---|---|---|---|---|---|
| pH | −20° C. | 2-8° C. | 25° C. | −20° C. | 2-8° C. | 25° C. |
| 5.0 | 115 | 110 | 28 | 85 | 81 | 53 |
| 5.5 | 118 | 108 | 25 | 85 | 82 | 53 |

Stability as a function of excipients. During the process of preparing formulations of EXT608 in 10 mM sodium acetate pH=5.5 with the excipient 0.8% saline added as an isotonic agent, it was discovered that EXT608 had a tendency to precipitate. Further investigation determined that the precipitation could be triggered by agitation, such as occurs during the routine mixing, pumping, and filtration steps during formulation and filling into sterile vials. Polysorbate 80 was investigated as an additional excipient to reduce precipitation. Polysorbate 80 concentrations of between 0.03% and 0.4% were tested and found to reduce precipitation caused by agitation of EXT608 solutions in a 96-well plate using a rotary shaking platform.

Further testing was done to substitute the ionic isotonic agent (saline) with a nonionic isotonic agent. EXT608 solutions formulated with 4.5% mannitol instead of 0.8% saline were less prone to precipitation caused by agitation or losses caused by non-specific absorption to surfaces. Therefore, formulations with mannitol brought the osmolality of the formulations to the desired range of between 275-295 mOsm/kg to match the osmolality of human plasma and fluids. This will reduce injection site pain while avoiding increased precipitation in saline.

EXT608 formulations were prepared at a concentration of 0.4 mg/ml in 10 mM sodium acetate buffer, pH=5.5, 4.5% mannitol, and 0.25% Polysorbate 80 then filled into sterile vials.

Example 14: Single Dose Pharmacokinetics and Pharmacodynamics of EXT608 in Humans EXT608 vastly improves the serum half-life in humans in a dose-dependent manner. Sterile EXT608 formulations were prepared at a concentration of 0.4 mg/ml in 10 mM sodium acetate buffer pH=5.5, 4.5% mannitol, and 0.25% Polysorbate 80 and filled into sterile vials. Healthy human participants were administered EXT608 by subcutaneous injection in the abdomen at doses of 0, 36, 108, 216, or 324 micrograms (n=3).

Pharmacokinetics: 4 ml Blood samples were collected at −24, −1, 0.5, 1, 2, 4, 8, 12, 18, 24, 36, 48, and 72 hours relative to dosing as well as on Days 5, 7, 14, 21, and 28 after dosing. They were processed to $K_2$EDTA plasma. Plasma levels of EXT608 were determined using the Immutopics High-sensitivity Human Parathyroid Hormone PTH(1-34) ELISA kit (cat #: 60-3900, Quidel Corporation, San Diego, CA) with the following modifications to the manufacturer's protocol: 1) before analysis, native PTH(1-84) was depleted from plasma samples (100 µl) using a goat anti-PTH(39-84) antibody (cat #: 21-3010, Quidel Corporation, San Diego, CA), 2) depleted plasma (75 µl) was added to the ELISA plate along with 75 µl of 1:1 PBS+0.05% Tween 20:Low-Cross Buffer (cat #: 100500, Boca Scientific, Dedham, MA), and 3) the calibration curve was established using an EXT608 reference sample. Group-averaged EXT608 levels as a function of time are shown in FIG. 23A. Pharmacokinetic parameters were calculated for each individual using Kinetica software (ThermoFisher Scientific, Waltham, MA), and the parameter means and standard deviations are given in Table 12. For the lower doses (36, 108, and 216 µg), an accurate elimination half-life ($t_{1/2}$) could not be determined because of limited timepoints with EXT608 concentrations above the lower limit of quantitation. For the high dose (324 µg), the $t_{1/2}$ was calculated to be 90±13 h; this and other parameters are given in Table 13.

TABLE 12

PK Parameters of EXT608 in Humans Following a Single SC Dose

| µg Dose | ng/ml Cmax | h Tmax | (ng/ml)*h $AUC_{last}$ | h $t_{last}$ |
|---|---|---|---|---|
| 36 | 0.49 ± 0.27 | 3.3 ± 1.2 | 5.9 ± 2.7 | 24 |
| 108 | 1.2 ± 0.3 | 5.3 ± 2.3 | 29.2 ± 8.4 | 48/72[a] |
| 216 | 1.3 ± 0.5 | 4.0 ± 0 | 41.7 ± 17.4 | 48/72/120 |
| 324 | 5.0 ± 2.0 | 2.7 ± 1.2 | 118 ± 11 | 168 |

[a]$t_{last}$ = 48 h (n = 1) or 72 h (n = 2). SC, subcutaneous; Cmax, maximum observed concentration; Tmax, time of maximum observed concentration; $AUC_{last}$, area under the concentration-time curve from time = 0 to the timepoint with the last measurable concentration ($t_{last}$).

TABLE 13

PK Parameters of EXT608 in Humans Following a Single 324 µg SC Dose

| h $t_{1/2}$ | (ng/ml)*h $AUC_{inf}$ | L/h Cl/F | L $V_Z/F$ | h MRT |
|---|---|---|---|---|
| 90 ± 13 | 151 ± 16 | 2.2 ± 0.2 | 280 ± 42 | 105 ± 18 |

$t_{1/2}$, terminal half-life; $AUC_{inf}$, area under the concentration-time curve from time = 0 to infinity; Cl/F, clearance (Cl) divided by bioavailability (F); $V_Z/F$, apparent volume of distribution during the terminal phase ($V_Z$) divided by bioavailability (F); MRT, mean retention time.

Pharmacodynamics: Blood samples were collected at −24, −1, 0.5, 1, 2, 4, 8, 12, 18, 24, 36, 48, and 72 hours relative to dosing as well as on Days 5, 7, 14, 21, and 28 after dosing. They were processed to serum and submitted to Quest Diagnostics for standard blood chemistry analysis including total calcium and albumin. Albumin-adjusted total serum calcium levels are shown in FIG. 23B. EXT608 raised serum calcium levels in a dose-dependent fashion and was able to maintain elevated calcium levels for 24 h. Blood samples (1.5 ml) were collected at −1, 4, 24, 48, and 72 hours relative to dosing as well as on Days 5, 7, 14, 21, and 28 after dosing. They were processed to EDTA plasma and submitted to Quest Diagnostics for intact PTH(1-84) analysis (Test Code #35202). In healthy humans, under conditions of elevated serum calcium, the body will attempt to restore normal calcium levels by a variety of mechanisms including suppression of endogenous PTH(1-84). EXT608 lowered endogenous PTH(1-84) levels in a dose-dependent fashion and was able to maintain lowered PTH(1-84) levels for approximately 3-4 days (FIG. 23C).

EXT608 did not cause a significant increase in urinary calcium at any dose level tested when measured at about 36 hours post-administration (data not shown).

Example 15: Additional Improved Formulation of EXT608

Effects of buffer composition and pH on propensity of EXT608 to precipitate. In Example 13, it was shown that EXT608 was prone to precipitation which could be triggered by agitation, such as occurs during the routine mixing, pumping, and filtration steps during formulation and filling into sterile vials. It was also shown that the propensity to precipitate was reduced by substitution of the ionic isotonic agent (saline) with a nonionic isotonic agent (mannitol) and by inclusion of polysorbate 80 (PS80) in the formulation. In this example, further improvements towards reducing the propensity to precipitate are made by altering the buffer composition and pH.

Analysis 1: Solutions of EXT608 (1 mg/ml) were made in 10 mM buffer with 4.5% mannitol. Acetate, citrate, and histidine buffers at pH values of between 4.0 and 5.5 were analyzed as indicated in Table 14A. Solutions were added to a sealed 96-well plate and shaken at 800 rpm on a rotary shaking platform. Absorbance measurements at 600 nm (OD600) were taken after 24 and 120 h as a measurement of light scattering caused by precipitation. After 24 h of shaking, the buffers containing citrate showed extensive precipitation, while the buffers containing acetate and histidine showed minimal precipitation.

TABLE 14A

OD600 absorption values of EXT608 solutions as a function of buffer composition after shaking for 24 and 120 h. All formulations contained 10 mM of the indicated buffer and 4.5% mannitol.

| Buffer | pH | 24 h | 120 h |
|---|---|---|---|
| Acetate | 5.5 | 0.078 | 0.198 |
| Citrate | 4.0 | 0.943 | 0.680 |
| Citrate | 4.5 | 1.599 | 1.240 |
| Citrate | 5.0 | 0.816 | 0.689 |
| Citrate | 5.5 | 0.910 | 0.702 |
| Histidine | 4.0 | 0.030 | 1.492 |
| Histidine | 4.5 | 0.050 | 1.406 |
| Histidine | 5.0 | 0.035 | 0.588 |
| Histidine | 5.5 | 0.082 | 0.340 |

Analysis 2: Solutions of EXT608 (1 mg/ml) were made in 10 mM buffer with 4.5% mannitol. Acetate pH=4.0, acetate pH=5.5, and histidine pH=4.0 buffers were tested as indicated in Table 14B. PS80 (Super Refined Polysorbate 80-LQ-(MH) SR48833, Croda, Inc., Plainsboro, NJ) was added to formulations at 0, 0.05, 0.1, or 0.25% (v/v). OD600 measurements were taken as in Experiment 1 over the course of 308 h. EXT608 solutions with acetate pH=4 buffer did not show any precipitation regardless of PS80 concentration for the 308 h duration of the analysis. In contrast, solutions with acetate pH=5.5 buffer in the absence of PS80 had precipitated by 20 h. Inclusion of 0.05, 0.10, or 0.25% PS80 delayed onset of precipitation to 140 h with some minimal precipitation (OD<0.1) observed for the 0.10% PS80 sample by 52 h. Solutions with histidine pH=4.0 buffer in the absence of PS80 had precipitated by 28 h. Inclusion of PS80 delayed onset of precipitation to 140 h with a high degree of precipitation observed for the 0.05 and 0.10% PS80 samples and minimal precipitation for the 0.25% PS80 sample. Therefore, acetate pH=4.0 is the preferable buffer for prevention of precipitation caused by agitation.

TABLE 14B

OD600 values of EXT608 solutions of varying buffer composition, pH, and PS80 concentration as a function of shaking time. All formulations contained 10 mM of the indicated buffer and 4.5% mannitol.

| Buffer | pH | % PS80 | 20 | 28 | 44 | 52 | 140 | 188 | 308 |
|---|---|---|---|---|---|---|---|---|---|
| Acetate | 4.0 | 0 | −0.001 | 0.000 | 0.001 | 0.005 | 0.006 | 0.009 | 0.015 |
| Acetate | 5.5 | 0 | 0.616 | 0.541 | 0.293 | 0.293 | 0.249 | 0.263 | 0.242 |
| Histidine | 4.0 | 0 | −0.019 | 0.560 | 0.483 | 0.444 | 0.398 | 0.463 | 0.431 |
| Acetate | 4.0 | 0.05 | −0.002 | −0.001 | 0.001 | 0.000 | 0.001 | 0.001 | 0.007 |
| Acetate | 5.5 | 0.05 | 0.002 | 0.000 | 0.002 | 0.002 | 0.362 | 0.704 | 0.662 |
| Histidine | 4.0 | 0.05 | 0.001 | 0.000 | 0.003 | 0.003 | 0.618 | 0.574 | 0.423 |
| Acetate | 4.0 | 0.10 | 0.003 | 0.008 | 0.001 | 0.010 | 0.002 | 0.003 | 0.006 |
| Acetate | 5.5 | 0.10 | −0.001 | 0.003 | 0.029 | 0.094 | 0.359 | 0.517 | 0.523 |
| Histidine | 4.0 | 0.10 | 0.001 | 0.001 | 0.005 | 0.017 | 0.463 | 0.540 | 0.483 |
| Acetate | 4.0 | 0.25 | 0.000 | 0.003 | 0.000 | 0.003 | 0.004 | 0.006 | 0.006 |
| Acetate | 5.5 | 0.25 | 0.000 | 0.001 | 0.004 | 0.004 | 0.235 | 0.375 | 0.411 |
| Histidine | 4.0 | 0.25 | 0.000 | 0.000 | 0.001 | 0.006 | 0.061 | 0.069 | 0.093 |

Analysis 3: Solutions of EXT608 (1 mg/ml) were made in 10 mM acetate buffer pH=4.0, 4.5, 5.0, or 5.5, with 4.5% mannitol. PS80 (Super Refined Polysorbate 80-LQ-(MH) SR48833, Croda, Inc., Plainsboro, NJ) was added to formulations at 0, 0.05, 0.1, or 0.25% (v/v). OD600 measurements were taken as in Analysis 1 over the course of 162 h Table 14C. EXT608 solutions with acetate pH=4 buffer did not show any precipitation regardless of PS80 concentration for the 162 h duration of the experiment. Solutions with acetate pH=4.5 buffer showed minimal precipitation (OD<0.1) by 42 h in the absence of PS80, minimal precipitation by 90 h with 0.05% or 0.10% PS80, and little or no precipitation by 162 h with 0.25% PS80. Solutions with acetate pH=5.0 buffer showed extensive precipitation by 42 h with 0 or 0.05% PS80, by 66 h with 0.1% PS80, and by 90 h with 0.25% PS80. Solutions with acetate pH=5.5 buffer showed extensive precipitation by 18 h with 0% PS80, by 42 h with 0.05 or 0.1% PS80, and by 66 h with 0.25% PS80. Therefore, the propensity of EXT608 to precipitate in acetate buffer was decreased with decreasing pH across the range of 5.5, 5.0, 4.5, and 4.0, with pH 4.0 being optimal for prevention of precipitation caused by agitation.

TABLE 14C

OD600 values of EXT608 solutions as a function of acetate buffer pH and PS80 concentration. All formulations contained 10 mM of acetate buffer and 4.5% mannitol.

| pH | % PS80 | 18 | 42 | 66 | 90 | 162 |
|---|---|---|---|---|---|---|
| 4.0 | 0 | 0.001 | 0.006 | 0.004 | 0.004 | 0.006 |
| 4.5 | 0 | 0.001 | 0.038 | 0.068 | 0.083 | 0.086 |

TABLE 14C-continued

OD600 values of EXT608 solutions as a function of acetate buffer pH and PS80 concentration. All formulations contained 10 mM of acetate buffer and 4.5% mannitol.

| pH | % PS80 | Time (h) | | | | |
|---|---|---|---|---|---|---|
| | | 18 | 42 | 66 | 90 | 162 |
| 5.0 | 0 | 0.000 | 0.504 | 0.338 | 0.237 | 0.222 |
| 5.5 | 0 | 0.607 | 0.551 | 0.359 | 0.388 | 0.316 |
| 4.0 | 0.05 | 0.004 | 0.000 | 0.000 | 0.004 | 0.003 |
| 4.5 | 0.05 | 0.001 | 0.001 | 0.001 | 0.067 | 0.043 |
| 5.0 | 0.05 | 0.004 | 0.208 | 0.362 | 0.513 | 0.570 |
| 5.5 | 0.05 | 0.000 | 0.314 | 0.572 | 0.388 | 0.324 |
| 4.0 | 0.10 | −0.002 | −0.001 | 0.002 | −0.001 | −0.001 |
| 4.5 | 0.10 | 0.001 | 0.001 | 0.001 | 0.028 | 0.067 |
| 5.0 | 0.10 | 0.001 | 0.002 | 0.383 | 0.649 | 0.678 |
| 5.5 | 0.10 | 0.003 | 0.331 | 0.657 | 0.712 | 0.718 |
| 4.0 | 0.25 | 0.001 | 0.006 | 0.004 | 0.006 | 0.001 |
| 4.5 | 0.25 | 0.000 | 0.001 | 0.004 | 0.001 | 0.013 |
| 5.0 | 0.25 | 0.001 | 0.007 | 0.006 | 0.132 | 0.210 |
| 5.5 | 0.25 | 0.000 | 0.004 | 0.136 | 0.247 | 0.309 |

Effects of formulation composition and pH on long-term storage stability of EXT608 solutions. An improved UPLC method was developed that was better able to separate impurities from the main EXT608 peak than previous methods, for example the UPLC method used to generate the data in Tables 10 and 11 (Example 13). By providing superior resolution and quantitation of the impurities, this improved method was better able to determine the ideal formulation composition and pH for minimizing the rate of EXT608 degradation and thereby increasing the shelf-life. An example of impurities now resolved by the improved UPLC method included those resulting from oxidation of the Methionine 8 and/or Methionine 18 residue(s) of the PTH1-34 component of EXT608. Oxidation of methionine is known to be catalyzed by peroxides such as hydrogen peroxide or peroxide impurities that can be present in polysorbate 80.

The improved UPLC method uses a Waters Acquity Peptide CSH C18 column (2.1×150 mm, 1.7 μm, 130 Å, part #: 186006938) with a flow rate of between 0.35-0.40 ml/min, a column temperature of 40° C., and a detection wavelength of 220 nm. Mobile Phase A consisted of 80% water, 20% acetonitrile, and 0.10% trifluoroacetic acid. Mobile Phase B consisted of 20% water, 80% acetonitrile, and 0.1% trifluoroacetic acid. The gradient conditions are given in Table 15A.

TABLE 15A

UPLC Gradient Conditions.

| Time (min) | % A | % B |
|---|---|---|
| Initial | 70 | 30 |
| 15.0 | 70 | 30 |
| 25.0 | 58 | 42 |
| 30.0 | 50 | 50 |
| 36.0 | 20 | 80 |
| 40.0 | 20 | 80 |
| 40.1 | 70 | 30 |
| 48.0 | 70 | 30 |

To determine whether free methionine added to the formulation reduced the rate of EXT608 degradation, EXT608 was prepared at 0.4 mg/ml in 10 mM sodium acetate pH 5.5 buffer with 4.5% mannitol and 0.25% PS80 with either 0, 5, 10, 20, or 40 mM methionine. Samples were placed in Eppendorf tubes and stored at 4° C. Free methionine was added to scavenge peroxides and any other oxidative species that could otherwise oxidize methionine residues of EXT608. In this analysis, an aged solution of PS80 was used that would have more peroxide impurities. Aliquots of EXT608 formulation were removed periodically over the course of 41 days, and the purity of EXT608 was determined by UPLC (Table 15B). Addition of methionine to the formulation at concentrations between 5 and 40 mM helped maintain the purity of EXT608.

TABLE 15B

Purity (%) of EXT608 as a Function of Methionine Concentration with Incubation at 4° C.

| | Methionine Concentration (mM) | | | | |
|---|---|---|---|---|---|
| Time (Day) | 0 | 5 | 10 | 20 | 40 |
| 0 | 89.7 | 89.7 | 89.7 | 89.7 | 89.7 |
| 5 | 81.2 | 82.9 | 83.3 | 85.0 | 85.4 |
| 11 | 75.4 | 79.7 | 80.4 | 81.6 | 83.1 |
| 21 | 71.6 | 75.8 | 77.6 | 78.6 | 80.2 |
| 41 | 65.3 | 70.2 | 71.9 | 73.3 | 76.6 |

To determine how histidine buffer compares to acetate in influencing the rate of EXT608 degradation, EXT608 was prepared at 0.4 mg/ml in 10 mM sodium acetate pH 5.5 buffer or 10 mM histidine pH 5.5 buffer. To each formulation was added 4.5% mannitol, and as indicated in Table 15C, either 0 or 0.25% PS80 and either 0 or 40 mM methionine. Samples were placed in Eppendorf tubes and stored at room temperature with aliquots removed for UPLC determination of EXT608 purity on Days 0, 5 and 11. Acetate buffer showed slower rates of EXT608 degradation than histidine buffer for each condition. Addition of 40 mM methionine slowed the rate of EXT608 degradation in acetate buffer but not in histidine buffer.

TABLE 15C

Purity (%) of EXT608 in pH 5.5 acetate vs histidine buffer with Incubation at Room Temperature.

| | Buffer: | | | | | |
|---|---|---|---|---|---|---|
| | Acetate | | | Histidine | | |
| | PS80 (%): | | | | | |
| | 0 | 0.25 | 0.25 | 0 | 0.25 | 0.25 |
| | Methionine (mM): | | | | | |
| | 0 | 0 | 40 | 0 | 0 | 40 |
| Day 0 | 89.7 | 89.7 | 89.7 | 89.4 | 89.4 | 89.4 |
| Day 5 | 84.6 | 82.5 | 84.4 | 80.5 | 79.3 | 79.1 |
| Day 11 | 81.7 | 69.5 | 81.5 | 71.7 | 69.2 | 50.0 |

To show how citrate buffer compares to acetate in influencing the rate of EXT608 degradation, EXT608 was prepared at 0.4 mg/ml in 10 mM sodium acetate pH 5.5 buffer or 10 mM sodium citrate pH 5.5 buffer. To each formulation was added 4.5% mannitol, and as indicated in Table 15D, either 0 or 0.25% PS80 and either 0, 2.5, 10 or 40 mM methionine. Samples were placed in Eppendorf tubes and stored at 4C with aliquots removed for UPLC determination of EXT608 purity over the course of 134 days. EXT608 shows similar rates of degradation in acetate vs citrate buffers, with citrate being slightly favorable with 0 or 2.5 mM methionine and acetate being slightly favorable with 10 or 40 mM methionine. The formulation with the lowest rate of EXT608 degradation was 10 mM acetate pH 5.5, 4.5% mannitol, 5.25% PS80, and 40 mM methionine.

TABLE 15D

Purity (%) of EXT608 in pH 5.5 acetate vs citrate buffer with Incubation at 4° C.

| | Buffer: | | | | | | | | | |
|---|---|---|---|---|---|---|---|---|---|---|
| | Acetate | | | | | Citrate | | | | |
| | PS80 (%): | | | | | | | | | |
| | 0 | 0.25 | 0.25 | 0.25 | 0.25 | 0 | 0.25 | 0.25 | 0.25 | 0.25 |
| | Methionine (mM): | | | | | | | | | |
| | 0 | 0 | 2.5 | 10 | 40 | 0 | 0 | 2.5 | 10 | 40 |
| Day 0 | 90.0 | 90.0 | 90.0 | 90.0 | 90.0 | 89.8 | 89.8 | 89.8 | 89.8 | 89.8 |
| Day 3 | 90.0 | 89.5 | 89.6 | 89.7 | 89.5 | 89.0 | 88.5 | 88.8 | 88.7 | 88.9 |
| Day 27 | 88.7 | 86.7 | 87.2 | 88.0 | 88.3 | 88.8 | 87.2 | 87.7 | 88.0 | 88.3 |
| Day 42 | 87.5 | 85.8 | 86.5 | 87.2 | 87.4 | 88.9 | 87.0 | 87.4 | 87.9 | 88.1 |
| Day 63 | 86.6 | 84.1 | 85.3 | 86.0 | 86.2 | 88.2 | 85.0 | 86.7 | 85.8 | 86.3 |
| Day 100 | 84.8 | 82.8 | 83.4 | 84.8 | 85.4 | 85.8 | 81.2 | 86.1 | 83.5 | 84.0 |
| Day 134 | 82.0 | 80.5 | 80.1 | 82.4 | 84.7 | 82.0 | 77.5 | 83.9 | 80.8 | 80.2 |

To determine how buffer pH influences the rate of EXT608 degradation, EXT608 was prepared at 1 mg/ml in either 10 mM sodium acetate pH 4.0 buffer, 10 mM sodium acetate pH 5.5 buffer, or 10 mM histidine pH 4.0 buffer. As indicated in Table 15E, to each formulation was added either 0 or 0.25% PS80, either 0, 10 or 40 mM methionine, and either 4.5, 4.1, or 3.0% mannitol (so as to keep the osmolality of the formulations constant). Samples were placed in 2 ml screw top glass vials and stored at 4° C. with aliquots removed for UPLC determination of EXT608 purity over the course of 69 days. Acetate pH 4.0 buffer was superior to acetate pH 5.5 buffer for each tested formulation. The rate of EXT608 degradation with acetate pH 4.0 buffer was similar to that with histidine pH 4.0 buffer in the formulation with no PS80. However, acetate pH 4.0 was superior to histidine pH 4.0 in formulations containing 0.25% PS80 and either 0, 10, or 40 mM methionine. The formulation with the lowest rate of EXT608 degradation was 10 mM sodium acetate pH 4.0 and 4.5% mannitol. The formulation with the next lowest rate of EXT608 degradation was 10 mM sodium acetate pH 4.0, 3.0% mannitol, 0.25% PS80, and 40 mM methionine.

To further determine how buffer pH influences the rate of EXT608 degradation, EXT608 was prepared at 1 mg/ml in either 10 mM sodium acetate pH 4.0, 4.5, 5.0, or 5.5 buffer. As indicated in Table 15F, to each formulation was added either 0 or 0.25% PS80, either 0 or 40 mM methionine, and either 4.5 or 3.0% mannitol (so as to keep the osmolality of the formulations constant). Samples were placed in 2 ml screw top glass vials and stored at room temperature with aliquots removed for UPLC determination of EXT608 purity over the course of 13 days. Without methionine, the rate of EXT608 degradation was faster with 0.25% PS80 vs 0% PS80 at all tested pH's; with addition of 40 mM methionine, the rate of EXT608 degradation with 0.25% PS80 was similar to or slower than that with 0% PS80. For each condition, the general trend is the rate of EXT608 degradation at pH 4.0</~pH 4.5<pH 5.0<pH 5.5.

TABLE 15E

Purity (%) of EXT608 in acetate pH 4.0 vs acetate pH 5.5 vs histidine pH 4.0 buffers with Incubation at 4° C.

| | Buffer: | | | | | | | | | | |
|---|---|---|---|---|---|---|---|---|---|---|---|
| | Acetate pH 4.0 | | | | Acetate pH 5.5 | | | | Histidine pH 4.0 | | |
| | PS80 (%): | | | | | | | | | | |
| | 0 | 0.25 | 0.25 | 0.25 | 0.25 | 0.25 | 0.25 | 0.25 | 0 | 0.25 | 0.25 | 0.25 |
| | Mannitol (%) | | | | | | | | | | |
| | 4.5 | 4.5 | 4.1 | 3.0 | 4.5 | 4.5 | 4.1 | 3.0 | 4.5 | 4.5 | 4.1 | 3.0 |
| | Methionine (mM): | | | | | | | | | | |
| | 0 | 0 | 10 | 40 | 0 | 0 | 10 | 40 | 0 | 0 | 10 | 40 |
| Day 0 | 90.8 | 90.5 | 90.4 | 90.3 | 90.5 | 90.0 | 90.2 | 90.0 | 90.2 | 89.8 | 89.7 | 90.3 |
| Day 2 | 90.0 | 89.3 | 89.7 | 89.8 | 89.8 | 88.6 | 89.2 | 89.2 | 90.0 | 88.8 | 89.4 | 89.5 |
| Day 13 | 89.8 | 88.5 | 89.3 | 89.2 | 89.4 | 87.1 | 88.1 | 88.5 | 89.6 | 87.7 | 88.7 | 88.9 |
| Day 38 | 88.8 | 87.2 | 88.3 | 88.7 | 88.3 | 84.5 | 86.5 | 86.8 | 88.9 | 86.0 | 87.6 | 87.9 |
| Day 69 | 88.4 | 85.6 | 87.2 | 87.7 | 87.5 | 82.3 | 85.0 | 85.3 | 88.5 | 84.6 | 86.4 | 86.8 |

TABLE 15F

Purity (%) of EXT608 in acetate pH 4.0, 4.5, 5.0, or 5.5 buffer with incubation at room temperature.

| | Buffer: | | | | | | | | | | |
|---|---|---|---|---|---|---|---|---|---|---|---|
| | Acetate pH 4.0 | | | Acetate pH 4.5 | | | Acetate pH 5.0 | | | Acetate pH 5.5 | | |
| | PS80 (%): | | | | | | | | | | | |
| | 0 | 0.25 | 0.25 | 0 | 0.25 | 0.25 | 0 | 0.25 | 0.25 | 0 | 0.25 | 0.25 |
| | Mannitol (%): | | | | | | | | | | | |
| | 4.5 | 4.5 | 3.0 | 4.5 | 4.5 | 3.0 | 4.5 | 4.5 | 3.0 | 4.5 | 4.5 | 3.0 |
| | Methionine (mM): | | | | | | | | | | | |
| | 0 | 0 | 40 | 0 | 0 | 40 | 0 | 0 | 40 | 0 | 0 | 40 |
| Day 0 | 90.6 | 90.3 | 90.2 | 90.2 | 90.0 | 90.1 | 90.4 | 89.8 | 90.2 | 90.1 | 89.1 | 90.0 |
| Day 5 | 87.2 | 83.5 | 86.9 | 85.8 | 83.6 | 86.7 | 82.6 | 80.2 | 85.8 | 85.9 | 79.3 | 81.1 |
| Day 13 | 85.2 | 81.4 | 85.2 | 86.0 | 80.4 | 85.2 | 85.7 | 77.7 | 83.6 | 83.9 | 74.2 | 79.2 |

EXEMPLARY SEQUENCES
(PTH (1-34))
                                                  SEQ ID NO: 1
SVSEIQLMHNLGKHLNSMERVEWLRKKLQDVHNF (PTH (1-84))
                                                  SEQ ID NO: 2
SVSEIQLMHNLGKHLNSMERVEWLRKKLQDVHNFVALGAPLAPRD

AGSQRPRKKEDNVLVESHEKSLGEADKADVNVLTKAKSQ (PTH-C)
                                                  SEQ ID NO: 3
SVSEIQLMHNLGKHLNSMERVEWLRKKLQDVHNFC (Vitamin D Binding Protein (DBP))
                                                  SEQ ID NO: 4
MKRVLVLLLAVAFGHALERGRDYEKNKVCKEFSHLGKEDFTSLSL

VLYSRKFPSGTFEQ VSQFVKEVVSFTEACCAEGADPDCYDTRTS

AFSAKSCESNSPFPVHPGTAECCTKEGFERKLCMAALKHQPQEFP

TYVEPTNDEICEAFRKDPKEYANQFMWEYSTNYGQAPLSLLVSYT

KSYLSMVGSCCTSASPTVCFLKERLQLKHLSLLTTLSNRVCSQYA

AYGEKKSRLSNLIKLAQKVPTADLEDVLPLAEDITNILSKCCESA

SEDCMAKELPEHTVKLCDNLSTKNSKFEDCCQEKTAMDVFVCTYF

MPAAQLPELPDVELPTNKDVCDPGNTKVMDKYTFELSRRTHLPEV

FLSKVLEPTLKSLGECCDVEDSTTCFNAKGPLLKKELSSFIDKGQ

ELCADYSENTFTEYKKKLAERLKAKLPDATPTELAKLVNKHSDFA

SNCCSINSPPLYCDSEIDAELKNIL (Vitamin D Binding Protein (DBP))
                                                  SEQ ID NO: 5
TTTAATAATAATTCTGTGTTGCTTCTGAGATTAATAATTGATTAA

TTCATAGTCAGGAATCTTTGTAAAAAGGAAACCAATTACTTTTGG

CTACCACTTTTACATGGTCACCTACAGGAGAGAGGAGGTGCTGCA

AGACTCTCTGGTAGAAAAATGAAGAGGGTCCTGGTACTACTGCTT

GCTGTGGCATTTGGACATGCTTTAGAGAGAGGCCGGGATTATGAA

AAGAATAAAGTCTGCAAGGAATTCTCCCATCTGGGAAAGGAGGAC

TTCACATCTCTGTCACTAGTCCTGTACAGTAGAAAATTTCCCAGT

GGCACGTTTGAACAGGTCAGCCAACTTGTGAAGGAAGTTGTCTCC

TTGACCGAAGCCTGCTGTGCGGAAGGGGCTGACCCTGACTGCTAT

GACACCAGGACCTCAGCACTGTCTGCCAAGTCCTGTGAAAGTAAT

TCTCCATTCCCCGTTCACCCAGGCACTGCTGAGTGCTGCACCAAA

GAGGGCCTGGAACGAAAGCTCTGCATGGCTGCTCTGAAACACCAG

CCACAGGAATTCCCTACCTACGTGGAACCCACAAATGATGAAATC

TGTGAGGCGTTCAGGAAAGATCCAAAGGAATATGCTAATCAATTT

ATGTGGGAATATTCCACTAATTACGGACAAGCTCCTCTGTCACTT

TTAGTCAGTTACACCAAGAGTTATCTTTCTATGGTAGGGTCCTGC

TGTACCTCTGCAAGCCCAACTGTATGCTTTTTGAAAGAGACTC

CAGCTTAAACATTTATCACTTCTCACCACTCTGTCAAATAGAGTC

TGCTCACAATATGCTGCTTATGGGGAGAAGAAATCAAGGCTCAGC

AATCTCATAAAGTTAGCCCAAAAAGTGCCTACTGCTGATCTGGAG

GATGTTTTGCCACTAGCTGAAGATATTACTAACATCCTCTCCAAA

TGCTGTGAGTCTGCCTCTGAAGATTGCATGGCCAAAGAGCTGCCT

GAACACACAGTAAAACTCTGTGACAATTTATCCACAAAGAATTCT

AAGTTTGAAGACTGTTGTCAAGAAAAAACAGCCATGGACGTTTTT

GTGTGCACTTACTTCATGCCAGCTGCCCAACTCCCCGAGCTTCCA

GATGTAGAGTTGCCCACAAACAAAGATGTGTGTGATCCAGGAAAC

ACCAAAGTCATGGATAAGTATACATTTGAACTAAGCAGAAGGACT

CATCTTCCGGAAGTATTCCTCAGTAAGGTACTTGAGCCAACCCTA

AAAAGCCTTGGTGAATGCTGTGATGTTGAAGACTCAACTACCTGT

TTTAATGCTAAGGGCCCTCTACTAAAGAAGGAACTATCTTCTTTC

ATTGACAAGGGACAAGAACTATGTGCAGATTATTCAGAAAATACA

TTTACTGAGTACAAGAAAAAACTGGCAGAGCGACTAAAAGCAAAA

TTGCCTGATGCCACACCCACGGAACTGGCAAAGCTGGTTAACAAG

CACTCAGACTTTGCCTCCAACTGCTGTTCCATAAACTCACCTCCT

```
CTTTACTGTGATTCAGAGATTGATGCTGAATTGAAGAATATCCTG

TAGTCCTGAAGCATGTTTATTAACTTTGACCAGAGTTGGAGCCAC

CCAGGGGAATGATCTCTGATGACCTAACCTAAGCAAAACCACTGA

GCTTCTGGGAAGACAACTAGGATACTTTCTACTTTTTCTAGCTAC

AATATCTTCATACAATGACAAGTATGATGATTTGCTATCAAAATA

AATTGAAATATAATGCAAACCATAAAAAAAAAAAAAAAAAAAAA

A
```

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A pharmaceutical composition comprising one or more parathyroid hormone 1-34 (PTH(1-34)) peptide(s) conjugated via a poly(ethylene glycol) (PEG) scaffold to a non-hormonal vitamin D moiety at the carbon 3 position (PTH conjugate); wherein the scaffold is not conjugated to an amine group of the PTH(1-34); wherein the PEG scaffold consist of 36 subunits at a molecular weight of 1,584 Daltons; wherein the PTH conjugate consists of the acetate salt of

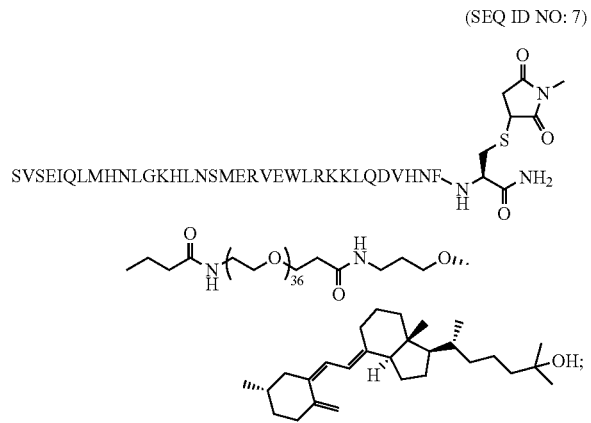

(SEQ ID NO: 7)

and wherein the composition comprises a pharmaceutically acceptable excipient.

2. The pharmaceutical composition of claim 1, wherein said pharmaceutical composition further comprises mannitol.

3. The pharmaceutical composition of claim 1, wherein said pharmaceutical composition further comprises Polysorbate 80 (PS80).

4. The pharmaceutical composition of claim 1, wherein said pharmaceutical composition further comprises methionine at a concentration of between about 0 and 40 mM+/−5 mM.

5. The pharmaceutical composition of claim 1 comprising 10 mM sodium acetate buffer (+/−10%); 3.0% to 4.5% mannitol; 0% to 0.25% Polysorbate 80; and 0 mM to 40 mM methionine.

6. The pharmaceutical composition of claim 1, wherein said pharmaceutical composition has a pH of about 5.5, and wherein said pharmaceutical composition comprises mannitol and PS80.

7. The pharmaceutical composition of claim 6, wherein said PTH conjugate is at a concentration of 0.4 mg/ml in about 10 mM sodium acetate buffer (+/−10%), pH about 5.5, about 4.5% mannitol (+/−1.5%), and about 0.25% Polysorbate 80 (+/−0.25%).

8. The pharmaceutical composition of claim 7, further comprising 0 mM to 40 mM methionine (+/−5 mM).

9. The pharmaceutical composition of claim 7, further comprising 40 mM methionine (+/−5 mM).

10. The pharmaceutical composition of claim 1, wherein said pharmaceutical composition has a pH of about 4.0 to about 5.5.

11. The pharmaceutical composition of claim 1, wherein said pharmaceutical composition has a pH of about 4.0.

12. The pharmaceutical composition of claim 10, wherein said pharmaceutical composition has a pH of about 5.5.

* * * * *

SEQUENCE LISTING

```
Sequence total quantity: 9
SEQ ID NO: 1           moltype = AA  length = 34
FEATURE                Location/Qualifiers
source                 1..34
                       mol_type = protein
                       organism = unidentified
SEQUENCE: 1
SVSEIQLMHN LGKHLNSMER VEWLRKKLQD VHNF                           34

SEQ ID NO: 2           moltype = AA  length = 84
FEATURE                Location/Qualifiers
source                 1..84
                       mol_type = protein
                       organism = unidentified
SEQUENCE: 2
SVSEIQLMHN LGKHLNSMER VEWLRKKLQD VHNFVALGAP LAPRDAGSQR PRKKEDNVLV 60
ESHEKSLGEA DKADVNVLTK AKSQ                                      84

SEQ ID NO: 3           moltype = AA  length = 35
FEATURE                Location/Qualifiers
source                 1..35
                       mol_type = protein
                       organism = unidentified
SEQUENCE: 3
SVSEIQLMHN LGKHLNSMER VEWLRKKLQD VHNFC                          35

SEQ ID NO: 4           moltype = AA  length = 474
FEATURE                Location/Qualifiers
source                 1..474
                       mol_type = protein
                       organism = unidentified
SEQUENCE: 4
MKRVLVLLLA VAFGHALERG RDYEKNKVCK EFSHLGKEDF TSLSLVLYSR KFPSGTFEQV 60
SQFVKEVVSF TEACCAEGAD PDCYDTRTSA FSAKSCESNS PFPVHPGTAE CCTKEGFERK 120
LCMAALKHQP QEFPPTYVEPT NDEICEAFRK DPKEYANQFM WEYSTNYGQA PLSLLVSYTK 180
SYLSMVGSCC TSASPTVCFL KERLQLKHLS LLTTLSNRVC SQYAAYGEKK SRLSNLIKLA 240
QKVPTADLED VLPLAEDITN ILSKCCESAS EDCMAKELPE HTVKLCDNLS TKNSKFEDCC 300
QEKTAMDVFV CTYFMPAAQL PELPDVELPT NKDVCDPGNT KVMDKYTFEL SRRTHLPEVF 360
LSKVLEPTLK SLGECCDVED STTCFNAKGP LLKKELSSFI DKGQELCADY SENTFTEYKK 420
KLAERLKAKL PDATPTELAK LVNKHSDFAS NCCSINSPPL YCDSEIDAEL KNIL       474

SEQ ID NO: 5           moltype = DNA  length = 1801
FEATURE                Location/Qualifiers
source                 1..1801
                       mol_type = unassigned DNA
                       organism = unidentified
SEQUENCE: 5
tttaataata attctgtgtt gcttctgaga ttaataattg attaattcat agtcaggaat 60
ctttgtaaaa aggaaaccaa ttacttttgg ctaccacttt tacatggtca cctacaggag 120
agaggaggtg ctgcaagact ctctggtaga aaaatgaaga gggtcctggt actactgctt 180
gctgtggcat ttggacatgc tttagagaga ggccgggatt atgaaaagaa taaagtctgc 240
aaggaattct cccatctggg aaaggaggac ttcacatctc tgtcactagt cctgtacagt 300
agaaaatttc ccagtggcac gtttgaacag gtcagccaac ttgtgaagga agttgtctcc 360
ttgaccgaag cctgctgtgc ggaaggggct gaccctgact gctatgacac caggacctca 420
gcactgtctg ccaagtcctg tgaaagtaat tctccattcc ccgttcaccc aggcactgct 480
gagtgctgca ccaaagaggg cctggaacga aagctctgca tggctgctct gaaacaccag 540
ccacaggaat tccctaccta cgtggaaccc acaaatgatg aaatctgtga ggcgttcagg 600
aaagatccaa aggaatatgc taatcaattt atgtgggaat attccactaa ttacggacaa 660
gctcctctgt cacttttagt cagttacacc aagagttatc tttctatggt agggtcctgc 720
tgtacctctg caagcccaac tgtatgcttt ttgaaagaga gactccagct taaacattta 780
tcacttctca ccactctgtc aaatagagtc tgctcacaat atgctgctta ggggagaag 840
aaatcaaggc tcagcaatct cataaagtta gcccaaaaag tgcctactgc tgatctggag 900
```

-continued

```
gatgttttgc cactagctga agatattact aacatcctct ccaaatgctg tgagtctgcc   960
tctgaagatt gcatggccaa agagctgcct gaacacacag taaaactctg tgacaattta  1020
tccacaaaga attctaagtt tgaagactgt tgtcaagaaa aaacagccat ggacgttttt  1080
gtgtgcactt acttcatgcc agctgcccaa ctccccgagc ttccagatgt agagttgccc  1140
acaaacaaag atgtgtgtga tccaggaaac accaaagtca tggataagta tacatttgaa  1200
ctaagcagaa ggactcatct tccggaagta ttcctcagta aggtacttga gccaacccta  1260
aaaagccttg tgaatgctg tgatgttgaa gactcaacta cctgttttaa tgctaagggc  1320
cctctactaa agaaggaact atcttctttc attgacaagg gacaagaact atgtgcagat  1380
tattcagaaa atacatttac tgagtacaag aaaaaactg cagagcgact aaaagcaaaa  1440
ttgcctgatg ccacacccac ggaactggca aagctggtta acaagcactc agactttgcc  1500
tccaactgct gttccataaa ctcacctcct ctttactgtg attcagagat tgatgctgaa  1560
ttgaagaata tcctgtagtc ctgaagcatg tttattaact ttgaccagag ttggagccac  1620
ccagggaat gatctctgat gacctaacct aagcaaaacc actgagcttc tgggaagaca  1680
actaggatac tttctacttt ttctagctac aatatcttca tacaatgaca agtatgatga  1740
tttgctatca aataaattg aaatataatg caaaccataa aaaaaaaaaa aaaaaaaaa  1800
a                                                                 1801

SEQ ID NO: 6             moltype = AA  length = 35
FEATURE                  Location/Qualifiers
source                   1..35
                         mol_type = protein
                         organism = synthetic construct
SITE                     1
                         note = Residue attached to hydrogen
SITE                     35
                         note = Hydroxylated and
                          succinimido-propionylamino-polyethylene glycol
                          36-Propionyl-aminoPropyl-25-hydroxy-Vitamin D modified
                          residue
SEQUENCE: 6
SVSEIQLMHN LGKHLNSMER VEWLRKKLQD VHNFC                              35

SEQ ID NO: 7             moltype = AA  length = 35
FEATURE                  Location/Qualifiers
source                   1..35
                         mol_type = protein
                         organism = synthetic construct
SITE                     1
                         note = Residue attached to hydrogen
SITE                     35
                         note = Amidated and succinimido-Propionylamino-polyethylene
                          glycol 36-Propionyl-aminoPropyl-25-hydroxy-Vitamin D
                          modified residue
SEQUENCE: 7
SVSEIQLMHN LGKHLNSMER VEWLRKKLQD VHNFC                              35

SEQ ID NO: 8             moltype = AA  length = 35
FEATURE                  Location/Qualifiers
source                   1..35
                         mol_type = protein
                         organism = synthetic construct
SITE                     35
                         note = Polyethylene glycol moiety (polyethylene glycol 36)
                          and Vitamin D modified residue
SEQUENCE: 8
SVSEIQLMHN LGKHLNSMER VEWLRKKLQD VHNFC                              35

SEQ ID NO: 9             moltype = AA  length = 35
FEATURE                  Location/Qualifiers
source                   1..35
                         mol_type = protein
                         organism = synthetic construct
VARIANT                  35
                         note = Hydroxylated and
                          succinimido-Propionylamino-polyethylene glycol
                          (39-58)-Propionyl-aminoPropyl-25-hydroxy-Vitamin D
                          modified residue
SEQUENCE: 9
SVSEIQLMHN LGKHLNSMER VEWLRKKLQD VHNFC                              35
```